US011932912B2

(12) United States Patent
Izumida et al.

(10) Patent No.: US 11,932,912 B2
(45) Date of Patent: Mar. 19, 2024

(54) METHOD FOR DETECTING OFF-TYPE OF *BRASSICA OLERACEA* PLANT

(71) Applicant: SAKATA SEED CORPORATION, Yokohama (JP)

(72) Inventors: Atsushi Izumida, Kanagawa (JP); Takao Suzuki, Kanagawa (JP); Tetsuya Hiramoto, Kanagawa (JP)

(73) Assignee: SAKATA SEED CORPORATION (JP)

( * ) Notice: Subject to any disclaimer, the term of this patent is extended or adjusted under 35 U.S.C. 154(b) by 612 days.

(21) Appl. No.: 16/639,324

(22) PCT Filed: Aug. 17, 2018

(86) PCT No.: PCT/JP2018/030486
§ 371 (c)(1),
(2) Date: Feb. 14, 2020

(87) PCT Pub. No.: WO2019/035480
PCT Pub. Date: Feb. 21, 2019

(65) Prior Publication Data
US 2021/0164057 A1 Jun. 3, 2021

(30) Foreign Application Priority Data
Aug. 17, 2017 (JP) .................................. 2017-157384

(51) Int. Cl.
C12Q 1/68 (2018.01)
C12Q 1/6895 (2018.01)

(52) U.S. Cl.
CPC ....... *C12Q 1/6895* (2013.01); *C12Q 2600/13* (2013.01); *C12Q 2600/156* (2013.01)

(58) Field of Classification Search
CPC .................... C12Q 1/6895; C12Q 2600/13
See application file for complete search history.

(56) References Cited

U.S. PATENT DOCUMENTS

2005/0262583 A1* 11/2005 Linders ..................... A01H 6/20
800/306
2011/0145944 A1* 6/2011 Laga ......................... A01H 6/20
536/23.6
2021/0164057 A1* 6/2021 Izumida .................. A01H 6/203

OTHER PUBLICATIONS

Ayele et al., 2005. Whole genome shotgun sequencing of *Brassica oleracea* and its application to gene discovery and annotation in *Arabidopsis*. Genome research, 15(4), pp. 487-495. (Year: 2005).*
Chiang, B.Y., Grant, W.F. and Chiang, M.S., 1979. The somatic karyotype of cabbage (*Brassica oleracea* ssp. *capitata*). Euphytica, 28(1), pp. 41-45. (Year: 1979).*
Dong et al., 2000. Development and applications of a set of chromosome-specific cytogenetic DNA markers in potato. Theoretical and Applied Genetics, 101(7), pp. 1001-1007. (Year: 2000).*
Henry, I.M., Dilkes, B.P. and Comai, L., 2006. Molecular karyotyping and aneuploidy detection in *Arabidopsis thaliana* using quantitative fluorescent polymerase chain reaction. The Plant Journal, 48(2), pp. 307-319. (Year: 2006).*
Ji, X., 2014. Dissertation. Numerical and structural chromosome aberrations in cauliflower (*Brassica oleracea* var. *botrytis*) and *Arabidopsis thaliana*. Wageningen University and Research. p. 1-138 (Year: 2014).*
Snowdon, R.J., 2007. Cytogenetics and genome analysis in *Brassica* crops. Chromosome Research, 15(1), pp. 85-95. (Year: 2007).*
Tonosaki et al., 2014. Supplementary. Molecular breeding, 34(3), pp. 1301-1311. (Year: 2014).*
Tonosaki et al., 2014. The use of species-specific DNA markers for assessing alien chromosome transfer in *Brassica rapa* and *Brassica oleracea*-monosomic additions of Raphanus sativus. Molecular breeding, 34(3), pp. 1301-1311. (Year: 2014).*
Geleta et al., 2012. Assigning *Brassica* microsatellite markers to the nine C-genome chromosomes using *Brassica rapa* var. *trilocularis-B. oleracea* var. *alboglabra* monosomic alien addition lines. Theoretical and Applied Genetics, 125(3), pp. 455-466. (Year : 2012).*
Koh et al., Jun. 15, 2017. A multiplex PCR for rapid identification of *Brassica* species in the triangle of U. Plant Methods, 13(1), pp. 1-8. (Year: 2017).*
Mason et al. High-throughput genotyping for species identification and diversity assessment in germplasm collections. Mol Ecol Resour. 2015; 15:1091-101. (Year: 2015).*
Quiros et al., 1991. Development and chromosomal localization of genome-specific markers by polymerase chain reaction in *Brassica*. Theoretical and Applied genetics, 82(5), pp. 627-632. (Year: 1991).*
Liu et al., 2014. The *Brassica oleracea* genome reveals the asymmetrical evolution of polyploid genomes. Nature communications, 5(1), pp. 1-11. (Year: 2014).*
Chable et al., 2008. "Aberrant" plants in cauliflower: 1. Phenotype and heredity. Euphytica, 164(2), pp. 325-337. (Year: 2008).*
Bubner et al., 2004. Use of real-time PCR for determining copy number and zygosity in transgenic plants. Plant cell reports, 23(5), pp. 263-271. (Year: 2004).*

(Continued)

*Primary Examiner* — Teresa E Strzelecka
*Assistant Examiner* — Olayinka A Oyeyemi
(74) *Attorney, Agent, or Firm* — Harness, Dickey & Pierce, P.L.C.

(57) ABSTRACT

The present specification discloses a method for detecting an aneuploid of a *Brassica oleracea* plant, including: performing real-time PCR using DNA extracted from a sample derived from a *Brassica oleracea* plant to be tested as a template and DNA markers specific to each of two or more chromosomes of *Brassica oleracea* plant; and detecting chromosomal aneuploidy from a relative difference in amplification amount between the obtained DNA markers. According to one embodiment of the present invention, it is possible to simply, accurately, and rapidly detect an off-type (chromosomal aneuploid) that may occur in *Brassica oleracea* varieties, in a laboratory equipped with a general molecular biological equipment in the course of seed quality control and breeding research.

9 Claims, 7 Drawing Sheets

Specification includes a Sequence Listing.

(56) References Cited

OTHER PUBLICATIONS

Ginzinger, D.G., 2002. Gene quantification using real-time quantitative PCR: an emerging technology hits the mainstream. Experimental hematology, 30(6), pp. 503-512. (Year: 2002).*
Idrees et al., 2014. Molecular markers in plants for analysis of genetic diversity: a review. European academic research, 2(1), pp. 1513-1540. (Year: 2014).*
Ingham et al., 2001. Quantitative real-time PCR assay for determining transgene copy number in transformed plants. Biotechniques, 31(1), pp. 132-140. (Year: 2001).*
Kordrostami, M. and Rahimi, M., 2015. Molecular markers in plants: concepts and applications. Genet. 3rd Millenn, 13, pp. 4024-4031. (Year: 2015).*
Moftah et al. Nov. 2014. Comparison of the Performance of QF-PCR with QPCR as A Rapid Molecular-Based Method for Sex Chromosome Aneuploidies Detection. JMSCR 2(11): pp. 2894-2902. (Year: 2014).*
Zimmermann, B.G. and Dudarewicz, L., 2008. Real-time quantitative PCR for the detection of fetal aneuploidies. In Prenatal Diagnosis (pp. 95-109). Humana Press. (Year: 2008).*
European Patent Office Extended Search Report issued for corresponding European Application No. 18846636.1, dated May 3, 2021 (9 pages).
Henry, Isabelle M., et al., "Molecular karyotyping and aneuploidy detection in *Arabidopsis thaliana* using quantitative fluorescent polymerase chain reaction", The Plant Journal, vol. 48, No. 2, Oct. 1, 2006 (Oct. 1 2006) 13 pgs.
Bubner, Ben, et al., "Use of real-time PCR for determining copy number and zygosity in transgenic plants", Plant Cell Reports, Springer, Berlin/Heidelberg, vol. 23, No. 5, Nov. 1, 2004 (Nov. 1, 2004) 9 pgs.
Chable, V. et al., ""Aberrant" plants in cauliflower: 2. Aneuploidy and global DNA methylation, Euphytica", 2009, vol. 170; pp. 275-287; published on Jun. 27, 2009 (13 pages).
Bernhard Zimmermann, et al., "Novel Real-Time Quantitative PCR Test for Trisomy 21 ", Clinical Chemistry 2002, vol. 48, No. 2, pp. 362-363 (2 pages).
Lech Dudarewicz et al., "Molecular methods for rapid detection of aneuploidy", J. Appl. Genet., 2007, vol. 46, No. 2, pp. 207-215 (9 pages).
Nathan R. Treff, Ph.D et al., "Development and validation of an accurate quantitative real-time polymerase chain reaction-based assay for human blastocyst comprehensive chromosomal aneuploidy screening", Fertility and Sterility, vol. 97, No. 4, pp. 819-824; Published Apr. 2012 by Elsevier Inc. (8 pages).
Mehrdad Hashemi, et al., "A Novel Multiplex Real-Time PCR Assay Using TaqMan MGB Probes for Rapid Detection of Trisomy 21", Middle-East Journal of Scientific Research., 2010, vol. 6, No. 4, pp. 398-402; Published in 2010 by IDOSI Publications (5 pages).
International Search Report issued for corresponding International Application No. PCT/JP2018/030486, dated Nov. 13, 2018 (4 pages).

* cited by examiner

FIG. 7

BROCCOLI

| KIND OF ANEUPLOID | CHARACTERISTICS |
|---|---|
| aneuploid (+C1) | LEAF SHAPE IS SLIGHTLY LONG AND THIN AND LEAF COLOR IS LIGHT. LATE MATURITY. |
| aneuploid (+C2) | LEAF MARGIN BECOMES CURLED SHAPE. FRESH PRODUCE WITH COMMODITY VALUE CAN BE HARVESTED IN MANY CASES. |
| aneuploid (+C3) | ALTHOUGH LEAF SHAPE SLIGHTLY RESEMBLES +C1, EACH LEAF IS SHORTER THAN THAT. LEAF COLOR IS CLOSE TO THAT OF NORMAL TYPE. |
| aneuploid (+C4) | LEAF SHAPE IS ROUND AND WIDE. WIDESPREAD PLANT HABIT. LEAF COLOR IS PALE. EARLY MATURITY. |
| aneuploid (+C5) | LEAF SHAPE IS SLIGHTLY ROUND AND THE LEAF SURFACE IS SMOOTH. LEAF COLOR IS SLIGHTLY PALE. |
| aneuploid (+C6) | EACH LEAF IS SMALL AND HAS DEEP COLOR, AND HAS SLIGHTLY WAXY BLOOM (SURFACE WAXINESS). EARLY MATURITY. |
| aneuploid (+C7) | FRINGE OF EACH LEAF IS STRONG. LATE MATURITY. |
| aneuploid (+C8) | LONG LEAF PETIOLE AND SMALL NUMBER OF LEAVES. LATE MATURITY. FRESH PRODUCE WITH COMMODITY VALUE CANNOT BE HARVESTED IN MANY CASES. |
| aneuploid (+C9) | EACH LEAF IS OBLONG AND HAS DEEP COLOR. SMALL NUMBER OF LEAVES AND SLOW GROWTH. FRESH PRODUCE CANNOT BE HARVESTED. |

CABBAGE

| KIND OF ANEUPLOID | CHARACTERISTICS |
|---|---|
| aneuploid (+C1) | LEAF COLOR IS PALE. SLIGHTLY LATE MATURITY. HEADING IS SLIGHTLY WEAK. |
| aneuploid (+C2) | LEAF COLOR IS DEEP AND ANTHOCYAN COLOR IS ALSO STRONG. HEADING IS WEAK. |
| aneuploid (+C4) | LEAF SHAPE IS ROUND. HEADING IS SLIGHTLY WEAK. |
| aneuploid (+C5) | LEAF SURFACE IS SMOOTH. HEADING IS SLIGHTLY WEAK. |
| aneuploid (+C6) | EACH LEAF IS SMALL AND DENSITY OF LEAF VEIN IS HIGH. SMALL SIZE. HEADING CAN BE SEEN. |
| aneuploid (+C7) | RESEMBLES +C1, BUT HAS SLIGHTLY DEEPER COLOR, AND IS LATER MATURITY. HEADING IS SLIGHTLY WEAK. |
| aneuploid (+C8) | LEAF COLOR IS DEEP AND ANTHOCYAN COLOR IS ALSO STRONG. RESEMBLES +C2 BUT HAS SMALLER SIZE AND HEADING IS DIFFICULT. |
| aneuploid (+C9) | SMALL, SLOW GROWTH AND SMALL NUMBER OF LEAVES. NOT HEADING AT ALL. |
| aneuploid (others) | IN CASE WHERE ANEUPLOIDY OCCURS IN PLURALITY OF CHROMOSOMES, ABNORMAL MORPHOLOGY BECOMES SEVERE AND FRESH PRODUCE CANNOT BE HARVESTED. |

CAULIFLOWER

| KIND OF ANEUPLOID | CHARACTERISTICS |
|---|---|
| aneuploid (+C1) | VIGOROUS BUT BUDS APPEAR LATE. LEAF COLOR IS SLIGHTLY PALE. |
| aneuploid (+C2) | CLOSE TO NORMAL TYPE, BUT LEAF COLOR IS SLIGHTLY DEEP. |
| aneuploid (+C4) | LEAF SHAPE IS ROUND AND LEAF COLOR IS LIGHT. VIGORLESS. |
| aneuploid (+C6) | THIN LEAVES AND VIGORLESS. EARLY MATURITY. |
| aneuploid (+C7) | THICK LEAF AND LEAF MARGIN HAS FRINGE SHAPE. VIGOROUS BUT SLOW GROWTH. |
| aneuploid (+C9) | SLOW GROWTH AND VIGORLESS. FRESH PRODUCE CANNOT BE HARVESTED. |

METHOD FOR DETECTING OFF-TYPE OF *BRASSICA OLERACEA* PLANT

CROSS-REFERENCE TO RELATED APPLICATIONS

The present application is based upon and claims the benefit of the priority from prior Japanese Patent Application No. 2017-157384, filed on Aug. 17, 2017; the entire contents of which are incorporated herein by reference.

BACKGROUND OF THE INVENTION

Technical Field

The present invention relates to a method for detecting an off-type (chromosomal aneuploid) of a *Brassica oleracea* crop. More specifically, the present invention relates to a method which is able to accurately and rapidly classify and detect individuals exhibiting various abnormal morphologies due to aneuploids, in *Brassica oleracea* (hereinafter, may be abbreviated as "*B. oleracea*"), at any growth stage by the molecular biological method.

Related Art

Brassicaceae plants are plant species which originated in the Middle East and the Mediterranean coast. This family includes plants of the genus *Brassica* extremely important agricultural crops. The *Brassica oleracea* plant species are very important and these include but are not limited to *B. oleracea* var. *capitata* (cabbage), *B. oleracea* var. *italica* (broccoli), *B. oleracea* var. *botrytis* (cauliflower), *B. oleracea* var. *gemmifera* (brussels sprouts), *B. oleracea* var. *gongyloides* (kohlrabi), *B. oleracea* var. *acephara* (ornamental cabbage, kale), and *B. oleracea* var. *albograbra* (Chinese kale).

In *Brassica oleracea* crops, commercial breeding is most often directed toward first-filial generation hybrid (F1) plants utilizing the properties of self incompatibility (SI) or cytoplasmic male sterility (CMS). Compared to native varieties or OP (open pollinated) varieties, F1 varieties show an excellent ability to adapt to the environment and present high uniformity. Consequently these varieties have a high commercial value and used in many countries.

It has been reported that individuals exhibiting a morphology different from the ordinary morphology appear at a certain frequency, even though they are F1 varieties inheriting parental genes (see the article of V. Ruffio-Chable et al., ISHS Acta Horticulturae 539 (2000) p. 89, Developmentally "Aberrant" plants in F1 hybrids of *Brassica oleracea* (Non-Patent Document 1)). Usually such off-type individuals are extremely low in value as agricultural products and cannot normally be shipped as fresh produce. If large amounts of individuals exhibiting an off-type phenotype involve certain seeds or varieties, this may lead to a big commercial problem. Accordingly, seed companies may need to discard such seeds.

The cause of the occurrence of such off-types was not known for a long time, but scientists speculated that there were environmental influences during seed production or crop cultivation or there were influences such as mutation or epigenetic changes.

The above-mentioned problem of off-types is also very troublesome to the quality control function of agricultural seed production companies. Seed companies that produce and sell F1 hybrid seeds conduct testing using polymorphic DNA markers or isozymes to test the varietal purity of seeds prior to commercializing said products. However, these off-type individuals have the same F1 genotype as the variety and cannot be detected by such laboratory tests. For this reason, development of a fast testing method for off-types has been desired for a long time.

Furthermore, in breeding research it is necessary to improve varietal characteristics so that such off-type individuals do not occur frequently. However, it is difficult to identify the off-types by their appearance at the seedling stage. For this reason, in order to accurately count the rate of occurrence of off-types, it has been necessary to cultivate the plants on a large scale in the field and have the characteristics of the individuals carefully evaluated by a skilled breeder. However, such a grow-out test tends to rely on subjectivity, and there has been concern that the result may vary depending on the person who performs the evaluation. Further, it is difficult for even a skilled breeder to make an accurate judgement and results may differ depending on the growth stage and cultivation environment. In light of this, a simple test method for seedlings has been desired by seed companies for a long time.

For example, the article of V. Chable et al., Euphytica 170 (2009) p. 275, "Aberrant" plants in cauliflower: 2. Aneuploidy and global DNA methylation (Non-Patent Document 2) states the possibility that an abnormal morphology appearing in the F1 variety of cauliflower is originated from an aneuploid. Several experimental studies have reported utilizing a flow cytometer as a general method for detecting aneuploidy.

However, it is not easy to accurately detect a difference of one chromosome in the method using the flow cytometer, and even if an endogenous control is added in the sample, it may be difficult to make a judgment as shown in the data described in the article of N. Roux et al., Plant Cell Report 21 (2003) p. 483, Rapid detection of aneuploidy in Musa using flow cytometry (Non-Patent Document 3). There is also a difference in the size of chromosomes, and the genomic ratio of the largest chromosome to the smallest chromosome may reach close to 2:1. In the case where a relatively small chromosome is added, it is difficult to judge because a difference between peaks of normal individuals and aneuploids is extremely small, and the detection sensitivity has a large influence on the accuracy of the results.

For this reason, the method which utilizes the flow cytometer creates problems such as not being able to perform a large-scale test in an ordinary laboratory.

Further, in the method using the flow cytometer, even if a highly reliable experiment system is assembled, in the case of plants that have aneuploidy in a plurality of chromosomes, for example, in the case of an aneuploid in which the chromosome 1 trisomy and the chromosome 2 monosomy are combined, 18 chromosomes are consequently contained in the nucleus, and thus it is determined to be a normal individual.

Further, it is difficult to identify which chromosome has caused aneuploidy in a simple test using a flow cytometer. Depending on the trisomic chromosome, there are also types in which fresh produce can be harvested without quality concerns; although the plant maturity changes somewhat. For example, in case involving trisomies of chromosomes 2 and 7 of broccoli and trisomies of chromosomes 1, 2, and 7 of cauliflower, thus in some cases, being an aneuploid is not immediately associated with a reduction of the commodity value. For this reason, it is important to be able to discriminate the type of trisomy individually in the field. From the viewpoint of advancing breeding, the fact that any chromosome tends to become a trisomy provides important information. Due to this, there has been a demand for the development of a simple test method that can analyze the detailed aneuploidy for each chromosome.

So far, in plants, methods for discriminating genotypes using DNA markers which utilizes PCR have been reported. For example, JP 3836451 B2 (Patent Document 1) discloses a method for determining the genotype involved in the production of pungent ingredients of *Capsicum* plants. However, as far as the present inventors know, the method for testing an off-type in a Brassicaceae plant has not been reported so far.

PRIOR ART LIST

Patent Document

Patent Document 1: Japanese Patent Publication No. 3836451 (JP 3836451 B2)

Non Patent Document

Non-Patent Document 1: V. Ruffio-Chable et al., ISHS Acta Horticulturae 539 (2000) p 89, Developmentally "Aberrant" plants in F1 hybrids of *Brassica oleracea*.
Non-Patent Document 2: V. Chable et al., Euphytica 170 (2009) p 275, "Aberrant" plants in cauliflower: 2. Aneuploidy and global DNA methylation.
Non-Patent Document 3: N. Roux et al., Plant Cell Report 21 (2003) p 483, Rapid detection of aneuploidy in Musa using flow cytometry.
Non-Patent Document 4: I. Parkin et al., Genetics 171 (2005) p 765, Segmental structure of the *Brassica napus* genome based on comparative analysis with *Arabidopsis thaliana*.
Non-Patent Document 5: X. Cheng et al., Theoretical Applied Genetics 118 (2009) p 1121, Development and genetic mapping of microsatellite markers from genome survey sequences in *Brassica napus*.

SUMMARY OF THE INVENTION

Problems to be Solved by the Invention

An object of the present invention is to provide a method for accurately and rapidly detecting an off-type (chromosomal aneuploid) that may occur in *Brassica oleracea* species, to solve the problem described above, affecting the course of seed quality control and breeding research. Further, the method can be performed in a laboratory equipped for general molecular biological methods.

Means for Solving Problems

As a result of extensive studies, conducted in order to respond to demands from seed quality control and breeding scientists, the present inventors have succeeded in accurately and rapidly identifying aneuploids of all chromosomes in *Brassica oleracea* species using real-time PCR. This method makes it possible to easily perform the method in a laboratory equipped for real-time PCR, and it has been possible to simply detect off-type plants. In addition, this method has been able to accurately and rapidly classify and detect individuals exhibiting various abnormal morphologies caused by aneuploid at any growth stage using the molecular biological method.

That is, according to the present invention, the following inventions are provided:

<1> A method for detecting an aneuploid of a *Brassica oleracea* plant, comprising:
performing real-time PCR using DNA extracted from a sample derived from the *Brassica oleracea* plant to be tested as a template and DNA markers specific to each of two or more chromosomes of the *Brassica oleracea* plant; and detecting chromosomal aneuploidy from a relative difference between the amplification values obtained by DNA markers.
<2> The method according to <1>, comprising determining whether a plant to be tested is an aneuploid for a chromosome of all chromosomes using DNA markers specific to each of chromosomes 1 to 9 of *Brassica oleracea* plant.
<3> The method according to <1> or <2>, wherein the method uses, as the DNA marker, a primer which is specific only to any one of chromosomal DNAs of the *Brassica oleracea* plant and can produce an amplification product by a PCR reaction when the chromosomal DNA is present.
<4> The method according to any one of <1> to <3>, wherein the method uses, as the DNA markers, (i) a primer which is specific only to any one of chromosomal DNAs of the *Brassica oleracea* plant and can produce an amplification product by a PCR reaction when the chromosomal DNA is present; and (ii) a probe which is specific to the chromosomal DNA identical to any one of chromosomal DNAs described in (i) and can detect an amplification product by PCR reaction based on the primer described in (i).
<5> The method according to <3> or <4>, wherein the method uses an intercalator that binds to a double-stranded DNA synthesized by a PCR reaction and emits fluorescence, or uses a probe modified with a fluorescent dye so as to emit fluorescence by a PCR elongation reaction.
<6> The method according to any one of <1> to <5>, wherein the method uses an increase in fluorescence signal obtained by real-time PCR as an index for detecting the aneuploid of chromosome.
<7> The method according to any one of <1> to <6>, wherein the method uses, as the DNA marker, one or more primers having nucleotide sequences shown in SEQ ID NOs: 1 to 18.
<8> The method according to any one of <1> to <7>, wherein the method uses, as the DNA marker, one or more primers having the nucleotide sequences shown in SEQ ID NOs: 1 to 18 and one or more probes having the nucleotide sequences shown in SEQ ID NOs: 19 to 27.
<9> A primer set for detecting an aneuploid of a *Brassica oleracea* plant, comprising: at least one or more primers having the nucleotide sequences shown in SEQ ID NOs: 1 to 18.
<10> A primer and probe set for detecting an aneuploid of a *Brassica oleracea* plant, comprising: at least one or more primers having the nucleotide sequences shown in SEQ ID NOs: 1 to 18; and at least one or more fluorescent dye-modified probes having the nucleotide sequences shown in SEQ ID NOs: 19 to 27.
<11> A method for breeding a *Brassica oleracea* crop, comprising evaluating a frequency of occurrence of aneuploids of chromosomes for each genetic line of the *Brassica oleracea* plant using the method according to any one of <1> to <8> in order to select a line with a low rate of occurrence of aneuploids.
<12> A method for controlling a quality of *Brassica oleracea* seeds, comprising testing to determine the contamination rate of aneuploids contained in seeds of a *Brassica oleracea* seed lot using the method according to any one of <1> to <8>.

<13> A method for controlling a quality of *Brassica oleracea* plants, comprising testing to determine the contamination rate of aneuploids contained in the *Brassica oleracea* plants using the method according to any one of <1> to <8>.

Effects of the Invention

According to the test method of the present invention, it becomes possible to simply and accurately estimate the rate of occurrence of off-types and the future morphology of each of the detected aneuploids, thereby enabling one to test the varietal purity of commercial seed lots and the frequency of occurrence of off-types from breeding lines. As a result, it becomes possible to efficiently, rapidly, and promptly provide a means to stably supply high-quality commercial seeds and breeding lines with good traits.

BRIEF DESCRIPTION OF DRAWINGS

FIG. 7 shows the phenotypic characteristics of aneuploids obtained from varieties of broccoli, cauliflower, and cabbage; these characteristics relate only to some of the phenotypic characteristics observed in the test of this example and it is not necessarily possible to generalize and characterize the characteristics for respective plant species and aneuploids.

EMBODIMENTS FOR CARRYING OUT THE INVENTION

Figure 1:
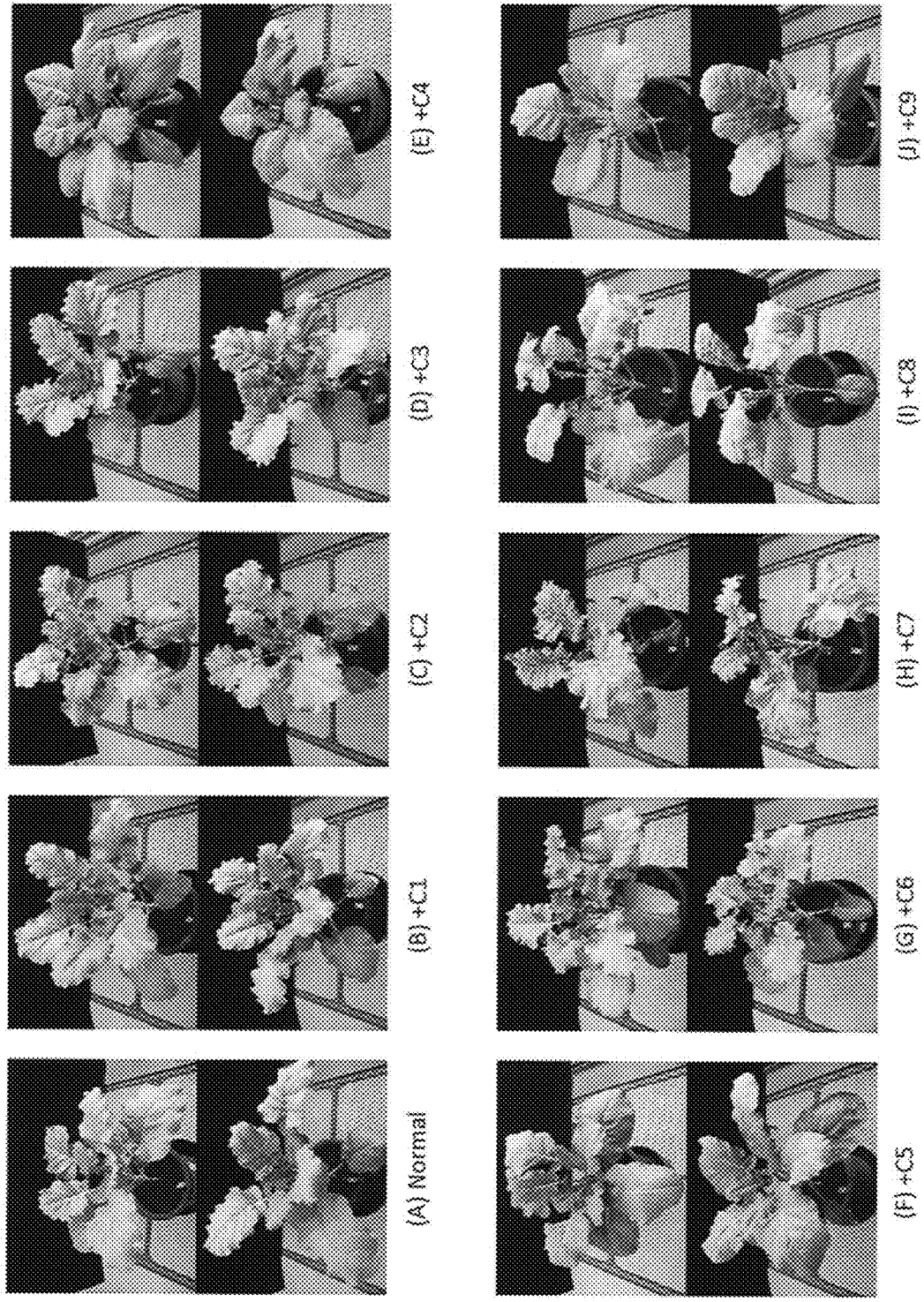
FIG. 1 shows phenotypes of aneuploids from broccoli plants, where in the figure, (A) represents a normal individual (Normal), (B) represents chromosome 1 trisomy (+C1), (C) represents chromosome 2 trisomy (+C2), (D) represents chromosome 3 trisomy (+C3), (E) represents chromosome 4 trisomy (+C4), (F) represents chromosome 5 trisomy (+C5), (G) represents chromosome 6 trisomy (+C6), (H) represents chromosome 7 trisomy (+C7), (I) represents chromosome 8 trisomy (+C8), and (3) represents chromosome 9 trisomy (+C9)

Hereinafter, the present invention will be described in detail.

As described above, the present invention relates to a method for detecting an aneuploid of a *Brassica oleracea* plant, including: performing real-time PCR using DNA extracted from a sample derived from a *Brassica oleracea* plant to be tested as a template and DNA markers specific to each of two or more chromosomes of a *Brassica oleracea* plant; and detecting chromosomal aneuploidy from a relative difference between the amplification values obtained by DNA markers. According to a preferred embodiment of the present invention, the number of chromosomes used for the detection method is 3 or more, 4 or more, 5 or more, 6 or more, 7 or more, and 8 or more are more preferred in this order. Most preferably, markers for all the nine chromosomes are used.

Therefore, the method of the present invention preferably includes: determining whether a plant to be tested is an aneuploid for a chromosome using DNA markers specific to each of chromosomes, 1 through 9, of *Brassica oleracea* plant.

In the present invention, the *Brassica oleracea* plant means a plant of *Brassica oleracea* species of the genus *Brassica*, which includes, but is not limited to, *B. oleracea* var. *capitata* (cabbage), *B. oleracea* var. *italica* (broccoli), *B. oleracea* var. *botrytis* (cauliflower), *B. oleracea* var. *gemmifera* (brussels sprout), *B. oleracea* var. *gongyloides* (kohlrabi), *B. oleracea* var. *acephara* (ornamental cabbage, kale), *B. oleracea* var. *albograbra* (Chinese kale). In the present invention, the *Brassica oleracea* plant is preferably broccoli, cauliflower or cabbage.

The term "aneuploid" or "off-type" used herein means an individual with a chromosome number abnormality (aneuploidy). In this case there is an abnormality in the number of chromosomes found in the *Brassica oleracea* plant. The number of chromosome in a normal *Brassica oleracea* plant is eighteen (2n=18), therefore resulting in nine pairs of chromosomes in one cell. For example, in the case of an aneuploid, specifically an aneuploid plant with chromosome 1 trisomy, the number in chromosome 1 is increased from two to three; this indicates that the ploidy level of chromosome 1 is abnormal. Although some aneuploid individuals may be acceptable as agricultural products or fresh produce depending on the plant species and growth situation, most often off-type individuals are poorly valued as agricultural products and in many cases may not be sold as fresh produce. For this reason, it is important to be able to detect aneuploids rapidly and simply.

In the aneuploid detection method of the present invention, a *Brassica oleracea* plant to be tested is sampled, DNA is extracted from a sample derived from the *Brassica oleracea* plant to be tested, and the DNA is used as a template for PCR.

In regard to the method of DNA extraction, any method known to those skilled in the art can be used to extract nucleic acid. In the present invention, the extracted crude DNA can be used as it is to serve as a template for PCR. For example, a phenol/chloroform method, a cell lysis method with a detergent, a cell lysis method with a protease enzyme, a physical destruction method with glass beads, a treatment method including repeating freeze-thawing, and a combination thereof may be used to perform DNA extraction. Various DNA extraction kits sold by reagent manufacturers, such as QIAGEN Plant mini Kit (manufactured by QIAGEN GmbH), may also be used. The DNA extracted by these methods is preferably held in a state suitable for use as a template for PCR. For example, the DNA is preferably stored at a low temperature after being dissolved in an appropriate buffer solution. The purity of the obtained DNA can be tested by measuring the absorbance at 230, 260, and 280 nm using a spectrophotometer. In performing PCR it is preferable that the ratio of the absorbance at 260/230 nm is 2.0 or more and the ratio of the absorbance at 260/280 nm is from 1.8 to 2.0. Regarding the obtained DNA solution, it may be confirmed that amplification occurs by PCR using a primer pair for an endogenous gene common to plants.

In the detection method of the present invention, real-time PCR is performed by using DNA extracted from a sample derived from *Brassica oleracea* plant to be tested as a template and a DNA marker capable of amplifying a part of each chromosome of the *Brassica oleracea* plant. Specifically, real-time PCR is performed using two or more DNA markers specific to each of two or more chromosomes of a *Brassica oleracea* plant as the DNA marker. More specifically, real-time PCR is performed by using two or more DNA markers specific to each of two or more chromosomes of chromosomes 1 through 9 of a *Brassica oleracea* plant as the DNA marker.

The DNA marker used herein is not particularly limited as long as it is a DNA marker located on any of the chromosomes of *Brassica oleracea* plant which is present as a single copy in the genome and is not affected by the other sequences present on different chromosomes. In the present invention, such a marker is used, thereby enabling the ability to detect a relative difference between the amplification values obtained by DNA markers by real-time PCR and to test aneuploids of various *Brassica oleracea* crops.

Therefore, it is preferable that the marker is a pair of primers which is specific to only one of chromosomal DNAs of the *Brassica oleracea* plant and can produce an amplification product by PCR reaction when the chromosomal DNA is present. Here, the term "specific to only one of the chromosomal DNAs of the *Brassica oleracea* plant" means that the primer is specific to only one of the nine chromosome pairs, but is not specific to other chromosomes. When the chromosomal DNA specific to only one of the nine chromosome pairs is present, the primer can amplify a target product by PCR reaction. For example, the DNA marker to be used may include a primer which is specific only to the DNA of chromosome 1 and can produce an amplification product by PCR reaction when the DNA of chromosome 1 is present.

Regarding the design of the primer used herein, a person skilled in the art can appropriately prepare a primer designed to be specific only to any one of chromosomal DNAs of the *Brassica oleracea* plant and to be able to produce an amplification product by PCR reaction when the chromosomal DNA is present. Specifically, the person skilled in the art can appropriately prepare a desired primer by referring to the description of Example 1 described later.

In the present invention, it is possible to test an aneuploid by performing real-time PCR using the primer having the above properties, and the intercalator method may be used as one preferred embodiment. In the intercalator method, an intercalator which has been added to a PCR reaction solution binds to a double-stranded DNA synthesized by a PCR reaction and the intercalator emits fluorescence. Accordingly, an elongation reaction by the primer occurs to amplify a product, thereby emitting fluorescence. This fluorescence is detected, making it possible to measure the relative difference between the amplification values obtained by DNA markers.

For example, SYBR Green I can be used as the intercalator.

According to a specific embodiment of the intercalator method, (i) a pair of primers which is specific to only one of the chromosomal DNAs of the *Brassica oleracea* plant and can amplify a product by PCR reaction when the chromosomal DNA is present and (ii) an intercalator is added to a PCR reaction solution, a fluorescence signal emitted in a step of elongation reaction in PCR is measured for every cycle, and the amplification values obtained by DNA markers are calculated. Consequently, it is possible to measure relative difference between the amplification values obtained by DNA markers.

Another preferred embodiment of the present invention is a probe method using a probe capable of detecting an amplification product generated by a PCR reaction based on the primer having the above properties. The probe to be used is not particularly limited as long as the probe can detect a target amplification product, and it is preferable to use a labeled probe which is modified with a fluorescent dye so that fluorescence is emitted by the PCR elongation reaction. The method for calculating relative difference between the amplification values obtained by DNA markers is performed by measuring the fluorescence emitted during the PCR elongation reaction, whereby the method can be performed by the same principle as the intercalator method. In addition, the probe method can reduce the risk of detecting non-specific PCR products, compared to the intercalator method.

According to a specific embodiment of the probe method, (i) a pair of primers which is specific to only one of chromosomal DNAs of the *Brassica oleracea* plant and can amplify a product by PCR reaction when the chromosomal DNA is present; and (ii) a probe which is specific to the chromosomal DNA identical to any one of chromosomal DNAs described in (i) and can detect an amplification product by PCR reaction based on the primers described in (i) are used, a fluorescence signal emitted in a step of elongation reaction in PCR is measured for every cycle, and the amplification values obtained by DNA markers are calculated. Consequently, it is possible to measure the relative difference between the amplification values obtained by DNA markers As for the fluorescence-labeled probe, a TaqMan probe double-labeled with a fluorescent substance and a quenching substance is preferred. In the TaqMan probe, the 5' end of a nucleic acid probe is usually modified with a fluorescent substance (reporter fluorescent dye) and the 3' end is usually modified with a quenching substance (quencher fluorescent dye). Examples of the reporter fluorescent dye include: fluorescein-based fluorescent dyes such as Cy3, Cy5, 6-carboxyfluorescein (6-FAM), 6-carboxy-4,7,2',7'-tetrachlorofluorescein (TET), and 6-carboxy-2',4',7',4,7-hexachlorofluorescein (HEX). As for the quencher fluorescent dye, a rhodamine-based fluorescent dye such as 6-carboxytetramethylrhodamine (TAM RA) or 6-carboxy-X-rhodamine (ROX) may be used. In the case of performing multiplex PCR, it is preferable to select a dark quencher such as BHQ-1, BHQ-2, BHQ-3 or Eclipse. In the present invention, it is possible to use, for example, a hydrolysis probe labeled with three types of fluorescent dyes such as FAM, HEX, and Cy5 at the 5' end and two types of quenchers such as BHQ-1 and BHQ-3 at the 3' end.

Therefore, in the detection method of the present invention, it is preferable to use an intercalator that binds to a double-stranded DNA synthesized by a PCR reaction and emits fluorescence or to use a probe modified with a fluorescent dye so as to emit fluorescence by a PCR elongation reaction.

In the case of using the fluorescent-dye modified probe, multiplex PCR can be performed by using probes labeled with different types of fluorescent dyes and mixing them with several types of markers. Similarly to the method described above, regarding each of the individual's samples to be tested and each of the markers, it is possible to measure a relative difference between the amplification values obtained by DNA markers based on the fluorescent signals emitted by fluorescent probes. In that process, in the case of multiplex PCR, it is possible to calculate the relative difference between the amplification values obtained by DNA markers in the same reaction solution set as the endogenous control and reduction of experimental errors would result in improvement of reliability of the result.

Therefore, according to a further preferred embodiment of the present invention, multiplex PCR is performed by the probe method.

Thus, according to one preferred embodiment of the present invention, an increase in fluorescence signal obtained by real-time PCR is used as an index for detecting an aneuploid of a chromosome in the detection method of the present invention.

The oligonucleotide to be used as a primer or probe can be synthesized by a known method in the art as a method for synthesizing the oligonucleotide, such as a phosphotriethyl method or a phosphodiester method, using a usual DNA automatic synthesizer.

According to a more preferred embodiment of the present invention, the DNA marker to be used may be one or more primers having the nucleotide sequences shown in SEQ ID NOs: 1 to 18, and more preferably, may be one or more primers described in Table 1 below, can be used. According to another more preferred embodiment of the present invention, it is possible use one or more primers having the nucleotide sequences shown in SEQ ID NOs: 1 to 18 and one or more probes having the nucleotide sequences shown in SEQ ID NOs: 19 to 27. More preferably, it is possible to use one or more primers described in Table 1 and one or more probes described in Table 2. These markers are markers corresponding to chromosomes 1 to 9.

Here, the DNA marker "having" a nucleotide sequence means that the marker has the nucleotide sequence. In the present invention, the DNA marker is specific to DNA of a predetermined chromosome as described above. Therefore, as long as the DNA marker has properties as the marker, one or several (for example, one, two or three, preferably one or two, and more preferably one) of any of the bases in the nucleotide sequence corresponding to the DNA may be substituted, deleted, added or eliminated, or the DNA marker may be a sequence which contains the nucleotide sequence corresponding to the DNA as a part and retains predetermined properties. In such a case, the term "having" may be paraphrased as "including". Further, in the case where the substitution, deletion, addition or elimination of one base is permitted, the term "having" may be paraphrased as "substantially consisting of".

According to another more preferred embodiment of the present invention, the DNA marker to be used may be one or more primer pairs having the nucleotide sequences shown in SEQ ID NOs: 1 to 18, and more preferably, may be one or more primer pairs described in Table 1 below. According to another more preferred embodiment of the present invention, it is possible use one or more primer pairs having the nucleotide sequences shown in SEQ ID NOs: 1 to 18 and a probe having the nucleotide sequences shown in SEQ ID NOs: 19 to 27 corresponding to the primer pairs. More preferably, it is possible to use one or more primer pairs described in Table 1 and one or more probes described in Table 2.

According to an even more preferred embodiment of the present invention, a more accurate and reproducible test can be performed by using the DNA markers divided into the following three sets:

Chromosome 6 marker, chromosome 4 marker and chromosome 2 marker;
    Chromosome 9 marker, chromosome 3 marker, and chromosome 8 marker; and
    Chromosome 1 marker, chromosome 5 marker, and chromosome 7 marker.

In the present invention, in addition to the use of the above primer pairs and probes, the real-time PCR method may be performed. For example, the method can be based on the ordinary methods described in Real-Time PCR Experiment Guide in Experimental Medicine, Supplement Edition, (YODOSHA CO., LTD), Saiki R K, et al., Science, 230: 1350-1354 (1985), and Plant PCR Experimental Protocol in Plant Cell Engineering, Supplement Edition, supervised by Ko Shimamoto and Takuji Sasaki (1995) and can be performed using commercially available real-time PCR kit or real-time PCR apparatus in accordance with the attached instructions.

As the real-time PCR apparatus, for example, LightCycler 480 System II (manufactured by Roche) or similar equipment can be used. At this time, for example, "Premix Ex Taq (Perfect Real Time)" (manufactured by Takara Bio Inc.) or similar reagents can be used as a reaction reagent, but usage is not particularly limited to the materials mentioned above.

First, using the DNA sample obtained by the above method as a template and using a predetermined primer or primer pair in the present invention, PCR is performed. The PCR amplification is not particularly limited except that the above primer or primer pair is used, and the PCR amplification can be performed according to an ordinary method. Regarding PCR conditions (such as the temperature and time for each of the steps of denaturation, annealing, and elongation, and the number of cycles) and the composition of a PCR reaction solution (such as the amount of DNA template, the type of a buffer solution, the concentration of a primer, the type and concentration of DNA polymerase, the concentration of dNTP, and the concentration of magnesium chloride), the person skilled in the art can appropriately select and set the conditions in which PCR amplification products can be obtained with a desired high sensitivity by PCR using the above-described primer or primer pair, based on the preliminary experiments or the like. In addition, a master mix for real-time PCR in which the DNA polymerase, dNTP concentration, and magnesium chloride concentration are approximately optimized is commercially available, so these may be utilized as appropriate.

As described above, the number of the chromosome of Brassica oleacea is eighteen (2n=18), so in the case of a normal plant there are nine pairs of chromosomes in each cell. On the other hand, for example, in the case of an aneuploid plant with chromosome 1 trisomy, chromosome 1 is increased from two to three copies. When real time PCR is performed using DNA extracted from these plants as a template and the DNA markers described in Table 1 or Tables 1 and 2, in the case of accurately standardizing the amount of DNA added to the reaction solution, in chromosome 1 trisomy, the amplification curve of the marker located on chromosome 1 rises in early cycles, compared to the normal individual. That is, a low threshold cycle value (also abbreviated as "Ct value", that is intersection point of the amplification curve of the marker obtained from the fluorescence intensity, and the threshold line set with a certain standard) is given.

Figure 2:
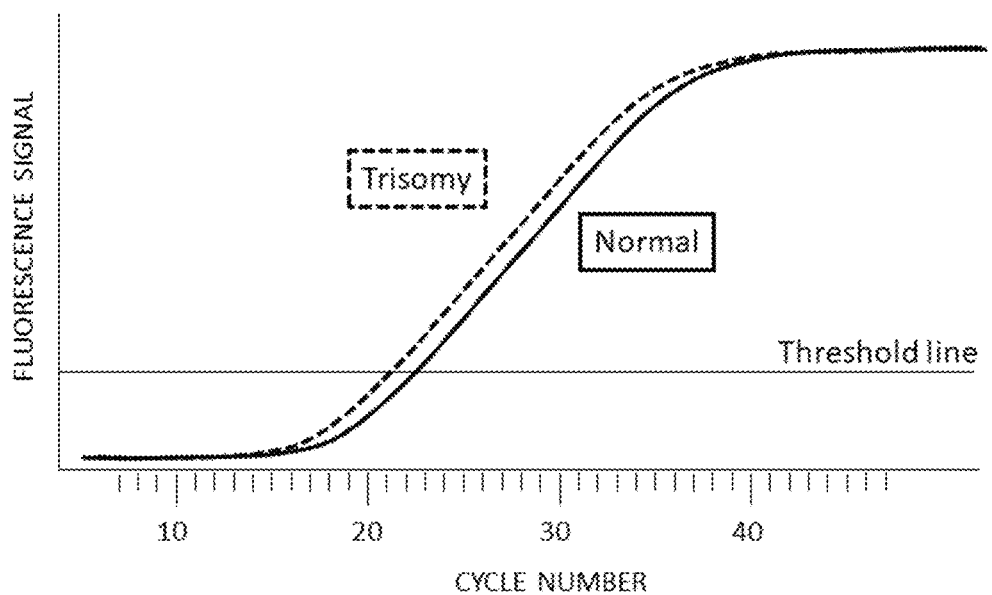
FIG. 2 shows an image of the amplification curve when performing quantitative analysis by real-time PCR, where the figure is based on an example of chromosome 6 trisomy, and when the amount of DNA as the template to be added to the PCR reaction solution is constant, for example in the case of chromosome 6 trisomy (Trisomy), the amplification curve of the marker located on chromosome 6 rises faster than that of normal individual (Normal)

As a specific example, as shown in FIG. 2, when the amount of DNA to be added to the reaction solution of PCR as a template is constant, for example, in the case of chromosome 6 trisomy (Trisomy), the amplification curve of the marker located on chromosome 6 rises faster than that of normal individual (Normal).

However, it is difficult to accurately standardize the amount of DNA in a large number of samples in an actual test site. Therefore, instead of standardizing the amount of DNA, the amplification of markers of chromosomes is subjected to relative quantification, whereby the number of each of the chromosomes can be estimated from the relative difference between the amplification values obtained by each of DNA markers, and the aneuploidy such as trisomy can be determined.

In order to widely apply this method to *Brassica oleracea* species, it is necessary to design primers for PCR in a common region for *Brassica oleracea* species in which single nucleotide polymorphisms (SNPs) do not exist. As a result of intensive studies by the present inventors, there has been success in designing DNA markers which can be widely applied to *Brassica oleracea* species and with which an efficient test can be performed by multiplex PCR. This led to the invention of the detection method of the present invention.

Therefore, in the detection method of the present invention, as described above, real time PCR is performed using a chromosome-specific DNA marker, and the chromosomal aneuploidy is detected from a relative difference between the amplification values obtained by DNA markers.

Here, relative difference between the amplification values obtained by DNA markers can be confirmed by performing real-time PCR on DNA markers that are specific to each of two or more chromosomes of the *Brassica oleracea* plant to be tested and comparing the amplification values for each of the chromosome markers. Hence, when the amplification of a plurality of chromosome markers is subjected to relative quantification and an abnormality in any of the chromosomes is present, an obvious difference occurs between the amplification of the marker on the aneuploid chromosome and the amplification of the markers on the chromosomes with normal ploidy level. As a result, it becomes possible to detect the presence of aneuploids.

The amplification values obtained by DNA markers can be confirmed by using the amplification curve of the marker. The amplification curve of the marker can be easily created based on the fluorescence intensity measured by PCR reaction.

In the case of performing measurement of the relative difference between the amplification values obtained by DNA markers, i.e., performing relative quantification, it is preferable to utilize the amplification curve obtained by each marker. For example, an intersection point between the amplification curve and the threshold line set with a certain standard is defined as a threshold cycle value (Ct value), and each Ct value is compared with another Ct value of different chromosome, thereby achieving the estimation of the number of target chromosomes. From the viewpoint of seeking more reproducible estimations of the chromosome number, Ct value can be substituted by the different value calculated by 2nd derivative method which differentiate the amplification curve twice, and adopt the cycle value of the position showing the maximum score.

In the present invention, regarding the Ct value indicated by each of the individuals in a sample to be tested and each of the markers, the value calculated by second derivative method as described above is adopted, and the ratio of copy numbers between the targeted genomic regions can be estimated based on relative difference between the amplification values obtained by DNA markers by the ΔΔCt method.

In other words, a part of the preferred embodiment of the detection method according to the present invention can be specifically expressed as the following methods (a) or (b):

(a) A method including: detecting the Ct value of each of the individuals in a sample to be tested and each of the markers from the signal emitted by a fluorescent dye such as SYBR Green I; and estimating the ratio of copy numbers of a targeted genomic region based on the relative difference between the amplification values obtained by DNA markers by methods such as the ΔΔCt method, where a fluorescent dye such as SYBR Green I is mixed with a PCR reaction solution, and markers of chromosomes are separately amplified by PCR; or (b) A method including: detecting the Ct value of each of the individuals in a sample to be tested and each of the markers from the fluorescence signal emitted by a florescent probe; and estimating the ratio of copy numbers of a targeted genomic region based on the relative difference between the amplification values obtained by DNA markers by methods such as the ΔΔCt method, where multiplex PCR is performed by using probes labeled with different types of fluorescent dyes and mixing several types of markers.

Although the method (a) can be performed with a relatively inexpensive reagent, separate PCR tests are performed for each chromosomes. Thus, multiple PCR tests are needed for each plant. In the method (b), it is necessary to synthesize a fluorescent probe, while relative difference between the amplification values obtained by DNA markers can be performed with the endogenous control as a standard. Thus, the number of tests can also be reduced.

The above-described primers, primer pairs, and probes can also be prepared as a kit. The kit of the present invention may be any one as long as the kit includes the above-described primer or primer pair, or at least a primer or a primer pair and a probe. If necessary, the kit may include a DNA molecule containing a target sequence as a positive control for PCR, a reagent for DNA extraction, a PCR buffer solution, a PCR reagent such as DNA polymerase, a labeling substance, and a manual.

Thus, according to another preferred embodiment of the present invention, a primer set is provided for the purpose for detecting an aneuploid of a *Brassica oleracea* plant, including at least one or more kinds of primers having the nucleotide sequences shown in SEQ ID NOs: 1 to 18. Further, according to still another preferred embodiment of the present invention, a primer and probe set is provided for the purpose of detecting an aneuploid of a *Brassica oleracea* plant, including: at least one or more primers having the nucleotide sequences shown in SEQ ID NOs: 1 to 18; and at least one or more fluorescent dye-modified probes having the nucleotide sequences shown in SEQ ID NOs: 19 to 27.

The method for detecting an aneuploid of the present invention is used to evaluate the frequency of occurrence of aneuploids of the chromosomes for each line of the *Brassica oleracea* plant. By utilizing this, the present invention can provide a method for breeding a *Brassica oleracea* crop, including selecting a line with a low rate of occurrence of aneuploids.

The method for detecting an aneuploid of the present invention is used so that it is possible to provide a method for controlling the quality of *Brassica oleracea* seeds, including testing the contamination rate of aneuploids contained in seeds of a *Brassica oleracea* seed lot.

The rate of aneuploids contained in seeds has been estimated by the grow-out test. Such testing requires a large-scale field and a growing period of several months. Further, it has been impossible to derive accurate results unless the grow-out is evaluated by a skilled examiner. According to the quality control method of seeds of the present invention, it is possible to perform the test for the rate of aneuploids in a space-saving manner, and to obtain rapid and accurate results.

The method for detecting an aneuploid of the present invention is used so that it is possible to provide a method for controlling the quality of a *Brassica oleracea* plants, including testing the contamination rate of aneuploids contained in the *Brassica oleracea* seed lot.

According to the quality control method of *Brassica oleracea* plant of the present invention, it is also possible to test newly emerged cotyledons from germinating seed as a material. Further, if the test for aneuploids is performed up to the planting stage, it is possible to select and cultivate only normal individuals. As a result, normal fresh produce can be harvested from almost all plants.

EXAMPLES

The present invention will be specifically described with reference to the following examples, but the present invention is not limited to these examples. For example, the sample to be tested, from which DNA is extracted, may be in any growth stage. Seeds, cotyledons, true leaves, roots, and any tissues may be used. No special method is required for the DNA extraction method as long as the DNA is purified to the extent that PCR can be performed without problems. As the fluorescent dye, any fluorescent dye may be used as long as it is a dye generally used in the real-time PCR method.

As shown in the following examples, the method of the present invention is versatile and can detect aneuploids in different crops such as broccoli, cauliflower and cabbage using a common marker. In addition, the present inventors have confirmed that this method can be performed on a large number of lines in addition to these examples, and this method is not limited to the line used in the following examples.

Example 1: Preparation of Marker

PCR was performed using random amplified polymorphic DNA (RAPD) primers (10 mer), Operon Technologies, Inc., and sequence related amplified polymorphism (SRAP) primers designed by the present inventors, and DNA of the broccoli F2 population as a template, thereby constructing a linkage map of *Brassica oleracea*.

Then, the linkage map constructed by the present inventors was compared with the article: I. Parkin et al., Genetics 171 (2005) p. 765, Segmental structure of the *Brassica napus* genome based on comparative analysis with *Arabidopsis thaliana*, the article: X. Cheng et al., Theoretical Applied Genetics 118 (2009) p. 1121, Development and genetic mapping of microsatellite markers from genome survey sequences in *Brassica napus*, and the public information registered in NCBI, thereby analyzing the relationship between markers located on linkage groups and public linkage maps.

Further, it was necessary to modify markers on chromosomes to broaden the use to include all kinds of *Brassica oleracea* species, and thus characteristic lines were selected from broad genetic resources of cabbage, broccoli, and cauliflower. DNAs of these lines were used as templates to identify regions without SNPs and the primers were redesigned.

These markers were used to perform PCR using nine types of trisomic plants as templates (FIG. 1) in which each of the chromosomes 1 to 9 identified in the course of marker development became trisomic. It was confirmed that there was no non-specific amplification from other chromosomes affecting the determination, and then each of the marker was considered as a marker specific to one of the chromosomes.

Further, in order to perform a simpler and stable multiplex fluorescence probe method, hydrolysis probes labeled with three types of fluorescent dyes including FAM, HEX, and Cy5 were designed. The goal was designing primers and probes such that even if three kinds of markers were mixed in a reaction solution, (i.e., even if six kinds of primers and three kinds of probes were mixed), the markers did not interfere with the probes and reproducible results could be obtained. Generally, when multiplex PCR is performed, complicated reactions such as formation of primer dimers and annealing of another primer to an amplified DNA fragment occur. Thus, it is difficult to construct a system that stably detects the difference between two and three chromosomes (1.5-fold difference) with respect to the crude template DNA. However, the present inventors succeeded in designing the markers shown in Tables 1 and 2 as a result of repeated improvement of the marker sequence and intensive studies.

Further, in order to perform a more accurate and stable test, the markers obtained from nine chromosomes were divided into three groups comprising of three markers each (see Example 4 to be described later).

TABLE 1

| Sequence listing of primers for PCR | | | |
|---|---|---|---|
| Seq ID | name | Chromosome | Sequence |
| Seq ID No: 1 | BoC1-Fw | C1 | CTGGCAAATGTAAGCCC-TTTCT |
| Seq ID No: 2 | BoC1-Rv | C1 | CTTGTCTTATTACAGCA-GATGCATTC |

TABLE 1-continued

Sequence listing of primers for PCR

| Seq ID | name | Chromosome | Sequence |
|---|---|---|---|
| Seq ID No: 3 | BoC2-Fw | C2 | CGCCATTGCTTTCTCTCTACTCT |
| Seq ID No: 4 | BoC2-Rv | C2 | GAAGAGGAAGGACTCGAGGAAG |
| Seq ID No: 5 | BoC3-Fw | C3 | CTTAGGATTCGGGTTCGTTTG |
| Seq ID No: 6 | BoC3-Rv | C3 | GCCGTAAGATTTCAAAGAGACTTC |
| Seq ID No: 7 | BoC4-Fw | C4 | CGTCTCTTGTGGTGGTTGAAG |
| Seq ID No: 8 | BoC4-Rv | C4 | TCAACTTCATCTGCTTGGTAATG |
| Seq ID No: 9 | BoC5-Fw | C5 | AGCACATCATCCCCCATACTT |
| Seq ID No: 10 | BoC5-Rv | C5 | CAGTCTCTCTcTCCTTGATGACG |
| Seq ID No: 11 | BoC6-Fw | C6 | AGGAAGAGGAAATTGTCATTCG |
| Seq ID No: 12 | BoC6-Rv | C6 | GTGACCGTTGCAGCAGATAA |
| Seq ID No: 13 | BoC7-Fw | C7 | AAGAAATTAGCCACAAGTCGTAAATA |
| Seq ID No: 14 | BoC7-Rv | C7 | ACGTGAATGATGGATATTTGATCTC |
| Seq ID No: 15 | BoC8-Fw | C8 | AAAGCTCGTGAAGCAAATACTACC |
| Seq ID No: 16 | BoC8-Rv | C8 | GAAGCATACCAGGAGGGAAATAA |
| Seq ID No: 17 | BoC9-Fw | C9 | GCCATCGCGAATCAAAGATA |
| Seq ID No: 18 | BoC9-Rv | C9 | ATTTGGTATTTTGCAGGCTACAG |

TABLE 2

Sequence listing of fluorescent probes

| Seq ID | name | Chromosome | Sequence | Example of fluorescence label |
|---|---|---|---|---|
| Seq ID No: 19 | BoC1-Prb | C1 | CACTTGTAAAACATGGGTTTGATCAAAAGA | 5'-FAM, 3'-BHQ1 |
| Seq ID No: 20 | BoC2-Prb | C2 | TCCTCTACTTCCACCCCATCTGCC | 5'-Cy5, 3'-BHQ3 |
| Seq ID No: 21 | BoC3-Prb | C3 | CCGATCTGAAAAGGGAGCTAACGAC | 5'-HEX, 3'-BHQ1 |
| Seq ID No: 22 | BoC4-Prb | C4 | TTGCAGCAAGGAGCTTAGACCACAG | 5'-HEX, 3'-BHQ1 |
| Seq ID No: 23 | BoC5-Prb | C5 | TCTCGAGAAATCTCATCGCTGCTTG | 5'-HEX, 3'-BHQ1 |
| Seq ID No: 24 | BoC6-Prb | C6 | TTCTCAGAGCTGTTCCCTCCTCCAC | 5'-FAM, 3'-BHQ1 |
| Seq ID No: 25 | BoC7-Prb | C7 | TTGCACCACCGTTACCTTTTAACACAA | 5'-Cy5, 3'-BHQ3 |
| Seq ID No: 26 | BoC8-Prb | C8 | TGTTTTGTTTGGTGGGCAAATCTCTT | 5'-Cy5, 3'-BHQ3 |
| Seq ID No: 27 | BoC9-Prb | C9 | TGGAGATCTTCCACCTCATCTTGGA | 5'-FAM, 3'-BHQ1 |

FIG. 2 shows the basic principle associated with relative quantification using real time PCR.

When the amount of DNA as the template to be added to the PCR reaction solution is constant, for example in the case of chromosome 6 trisomy, the amplification curve of the marker located on chromosome 6 rises faster than that of normal individual. In the case of performing relative quantification, an intersection point between the amplification curve and the threshold line set with a certain standard is defined as a Ct value and compared with the Ct value of each of the markers of other chromosomes, thereby achieving the estimation of the number of target chromosomes.

Figure 3:
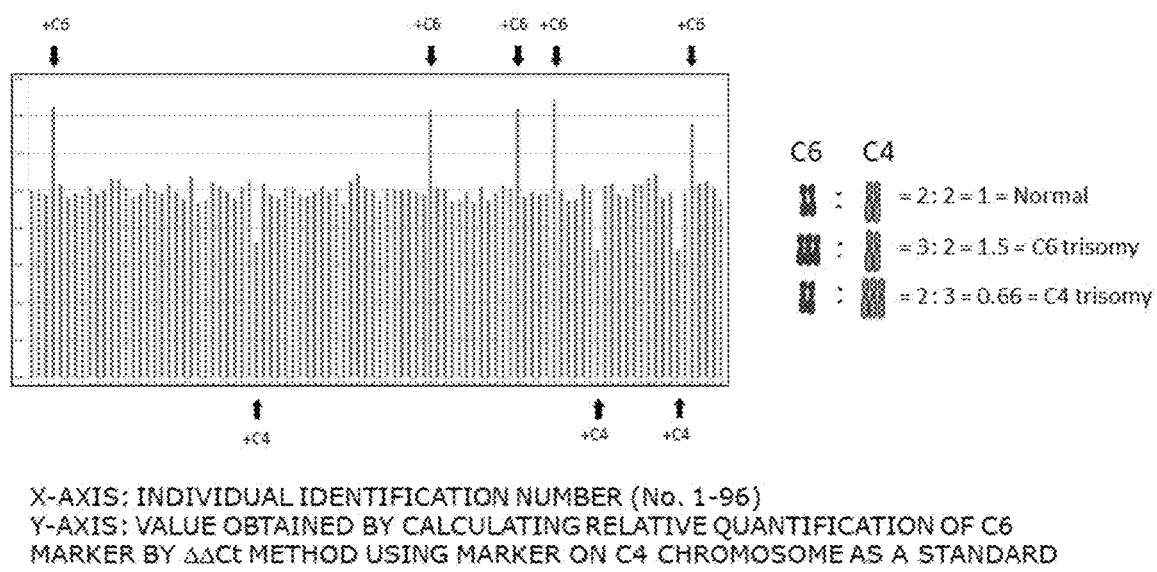
FIG. 3 shows an example of aneuploid detection, namely, an example of the calculated result from a relative difference between the amplification values obtained by DNA markers by performing real time PCR. Ninety-six individuals, obtained from the F1 generation of a broccoli variety being used as materials, were tested by multiplex PCR using a chromosome 4 marker and a chromosome 6 marker, the marker on chromosome 6 was subjected to a relative difference between the amplification values on the chromosome 4 as a standard, and as a result, the chromosome 6 trisomy and the chromosome 4 trisomy could be identified.

FIG. 3 shows an example of the calculation result of relative quantification obtained by performing real time PCR. In this test, multiplex PCR was performed by the fluorescent probe method using 96 individuals of an F1 variety of broccoli as materials, a chromosome 4 marker, and a chromosome 6 marker. The "LightCycler 480 System II" of Roche was used as a real-time PCR machine, and "Premix Ex Taq (Perfect Real Time)" of Takara Bio Inc. was used as a reaction reagent. In the figure, the X axis shows the number of individuals and the Y axis shows the relative quantification of the chromosome 6 marker calculated by the ΔΔCt method using the chromosome 4 marker as a standard.

Among the 96 individuals tested, 88 normal type individuals showed a value around 1, while 5 individuals with chromosome 6 trisomy showed a value around 1.4 and 3 individuals with a chromosome 4 trisomy showed a value around 0.7. When the PCR amplification efficiency was assumed as double per cycle, the theoretical values of chromosome 6 trisomy and chromosome 4 trisomy were 1.5 and 0.66, respectively, and thus the actual values were close to these values.

Example 2 Observation of Chromosome in Trisomic Plant of Broccoli

Among the plants determined to be trisomic by real-time PCR, the chromosome 6 trisomy, the chromosome 7 trisomy, and the chromosome 2 trisomy were used as materials and the chromosome were observed.

Anthers were taken out from broccoli's buds having a length of 1 to 2 mm and dyed with 1% Orcein acetic acid solution. The chromosomes at first metaphase (MI stage) of meiosis of pollen mother cells were observed.

Figure 4:
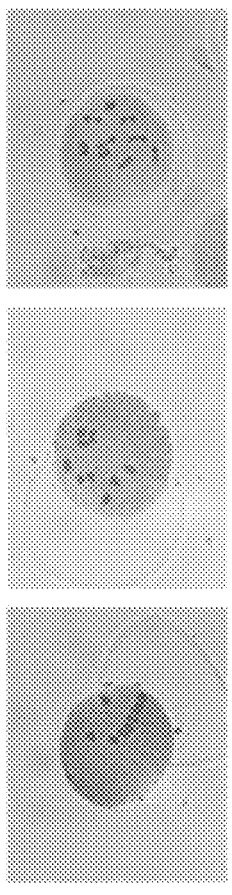
FIG. 4 shows micrographs of chromosomes observed in pollen mother cells of trisomic plants. Using microscopic observation of the cells at first metaphase of meiosis of pollen mother cells, nine divalent chromosomes were observed in the case of the normal chromosome (2n=18). While nine divalent chromosomes and one additional chromosome (indicated by an arrow) were observed in the case of the chromosome level of the trisomic plant (2n+1)
Figure 4:
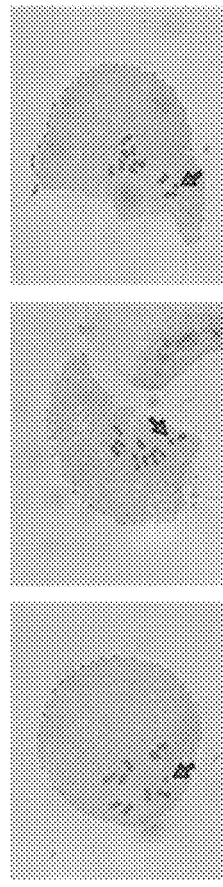
Figure 4:
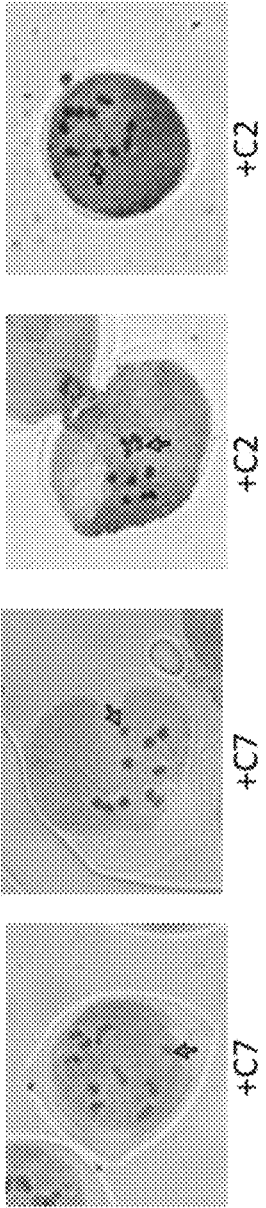

The results were as shown in FIG. 4.

As shown in FIG. 4, in the case of the chromosome of the normal individual, nine divalent chromosomes were observed (2n=18). Meanwhile, in the case of the chromosome observed in the trisomic plant, nine divalent chromosomes and one chromosome (indicated by an arrow) were observed (2n+1).

Example 3 Detection of Off-type in Broccoli

The seeds of the F1 variety of broccoli "SBR-48" under development by SAKATA SEED CORPORATION were sown in nursery trays. DNA of 445 individuals was extracted from newly emerged cotyledons from germinating seeds and real-time PCR was performed by the SYBR method using markers specific to each chromosomes.

Specifically, primers having the nucleotide sequences shown in SEQ ID NOs: 1 to 18 were used as the markers specific to the chromosomes. SYBR Green I (purchased from Roche) as an intercalator was added to a normal PCR reaction solution resulting in a final concentration of 1/20000, then PCR was performed. For real-time PCR, "LightCycler 480 System II" of Roche was used. The method used for PCR included incubation at 95° C. for 1 minute, followed by 40 cycles of 3-step PCR at 95° C. for 15 seconds, 60° C. for 30 seconds and 72° C. for 30 seconds. In the signal measurement with SYBR Green I, a filter with an excitation wavelength of 465 nm and a detection wavelength of 510 nm was used.

Based on the Ct value obtained by second derivative method, the relative quantification was calculated by the ΔΔCt method using the marker on chromosome 9 as a standard.

The results were as shown in Table 3.

These results are summarized in Table 3 for each chromosome, and thus it is clear that the aneuploids are included at the ratio as shown in Table 4.

In this example, no chromosome 3 trisomy appeared. However, as shown in FIG. 1, the chromosome 3 trisomy appears in rare cases (the phenotypic characteristics of each chromosome trisomy are as shown in FIG. 7). Note that the present inventors have separately confirmed that there is no problem with the designed markers including the chromosome 3 trisomy.

TABLE 3

Result of testing aneuploid in the F1 variety of broccoli (raw data obtained by PCR based on the SYBR method (value calculated by the ΔΔCt method))

| individual No. | SYBR C1 C1/C9 ΔΔCt | SYBR C2 C2/C9 ΔΔCt | SYBR C3 C3/C9 ΔΔCt | SYBR C4 C4/C9 ΔΔCt | SYBR C5 C5/C9 ΔΔCt | SYBR C6 C6/C9 ΔΔCt | SYBR C7 C7/C9 ΔΔCt | SYBR C8 C8/C9 ΔΔCt | SYBR C9 C9/C9 ΔΔCt | results |
|---|---|---|---|---|---|---|---|---|---|---|
| 1 | 0.98 | 1.06 | 1.04 | 1.11 | 0.95 | 1.08 | 0.94 | 0.96 | 1.00 | Normal |
| 2 | 1.03 | 0.98 | 0.99 | 1.02 | 0.98 | 1.04 | 0.95 | 0.91 | 1.00 | Normal |
| 3 | 0.86 | 0.96 | 1.13 | 1.23 | 1.04 | 0.92 | 1.10 | 1.18 | 1.00 | aneuploid (+C4) |
| 4 | 0.98 | 1.03 | 0.97 | 0.99 | 1.03 | 1.03 | 0.95 | 0.98 | 1.00 | Normal |
| 5 | 1.10 | 1.00 | 0.94 | 1.12 | 0.93 | 1.07 | 0.95 | 0.99 | 1.00 | Normal |
| 6 | 0.96 | 0.99 | 0.95 | 0.94 | 0.96 | 1.03 | 0.95 | 0.95 | 1.00 | Normal |
| 7 | 1.01 | 1.05 | 1.01 | 1.02 | 1.00 | 1.05 | 0.93 | 0.96 | 1.00 | Normal |
| 8 | 1.03 | 0.99 | 0.98 | 1.06 | 1.00 | 1.07 | 0.95 | 0.94 | 1.00 | Normal |
| 9 | 1.03 | 0.96 | 0.94 | 1.02 | 0.96 | 1.01 | 0.95 | 0.95 | 1.00 | Normal |
| 10 | 1.03 | 0.93 | 1.01 | 0.99 | 1.01 | 0.92 | 1.00 | 0.98 | 1.00 | Normal |
| 11 | 0.95 | 0.98 | 0.96 | 0.96 | 0.94 | 1.05 | 0.92 | 0.90 | 1.00 | Normal |
| 12 | 1.03 | 1.01 | 0.93 | 1.06 | 0.94 | 1.08 | 0.94 | 1.09 | 1.00 | Normal |
| 13 | 1.05 | 1.05 | 1.02 | 1.01 | 1.04 | 1.08 | 0.97 | 1.10 | 1.00 | Normal |
| 14 | 1.01 | 1.04 | 1.08 | 1.00 | 1.03 | 1.08 | 0.95 | 0.96 | 1.00 | Normal |
| 15 | 1.08 | 1.08 | 1.07 | 1.01 | 1.08 | 1.06 | 0.96 | 0.96 | 1.00 | Normal |
| 16 | 1.00 | 1.02 | 0.98 | 1.02 | 1.00 | 1.07 | 0.98 | 0.95 | 1.00 | Normal |
| 17 | 0.97 | 1.02 | 0.99 | 1.01 | 0.96 | 1.05 | 0.98 | 0.98 | 1.00 | Normal |
| 18 | 1.02 | 1.03 | 1.04 | 1.12 | 0.99 | 1.05 | 0.92 | 1.00 | 1.00 | Normal |
| 19 | 1.03 | 0.98 | 0.99 | 1.14 | 1.00 | 1.02 | 0.93 | 0.92 | 1.00 | Normal |
| 20 | 1.03 | 1.04 | 0.98 | 1.12 | 1.03 | 1.03 | 0.97 | 1.02 | 1.00 | Normal |
| 21 | 1.04 | 1.06 | 0.99 | 1.04 | 1.03 | 1.08 | 0.99 | 1.03 | 1.00 | Normal |
| 22 | 1.00 | 0.94 | 0.98 | 1.02 | 0.99 | 1.00 | 1.00 | 1.01 | 1.00 | Normal |
| 23 | 0.96 | 0.97 | 0.97 | 1.03 | 0.98 | 1.02 | 0.97 | 1.02 | 1.00 | Normal |
| 24 | 0.98 | 1.03 | 1.01 | 0.96 | 1.01 | 1.05 | 0.98 | 0.98 | 1.00 | Normal |
| 25 | 0.91 | 1.00 | 1.06 | 1.00 | 1.00 | 1.02 | 0.96 | 1.00 | 1.00 | Normal |
| 26 | 0.92 | 1.00 | 1.01 | 1.02 | 1.03 | 1.06 | 1.00 | 0.99 | 1.00 | Normal |
| 27 | 0.99 | 0.98 | 0.91 | 1.03 | 0.98 | 0.99 | 0.92 | 0.98 | 1.00 | Normal |
| 28 | 0.97 | 1.01 | 0.94 | 1.01 | 1.00 | 1.04 | 0.92 | 0.95 | 1.00 | Normal |
| 29 | 1.04 | 1.03 | 0.98 | 1.10 | 1.02 | 1.10 | 0.95 | 1.02 | 1.00 | Normal |
| 30 | 1.00 | 1.02 | 1.01 | 1.05 | 1.07 | 1.08 | 1.02 | 1.00 | 1.00 | Normal |
| 31 | 0.97 | 0.97 | 0.99 | 0.97 | 1.02 | 0.98 | 0.95 | 0.96 | 1.00 | Normal |
| 32 | 0.90 | 0.97 | 0.97 | 0.98 | 0.99 | 1.00 | 1.41 | 0.92 | 1.00 | aneuploid (+C7) |
| 33 | 0.59 | 0.90 | 0.91 | 0.83 | 0.92 | 0.89 | 1.25 | 0.90 | 1.00 | aneuploid (others) |
| 34 | 1.01 | 0.99 | 0.99 | 0.99 | 1.03 | 1.04 | 0.93 | 0.96 | 1.00 | Normal |
| 35 | 0.95 | 1.04 | 1.01 | 0.98 | 1.07 | 0.95 | 1.09 | 1.02 | 1.00 | Normal |
| 36 | 1.43 | 1.00 | 0.97 | 1.05 | 1.02 | 1.03 | 0.98 | 0.98 | 1.00 | aneuploid (+C1) |
| 37 | 0.98 | 1.00 | 0.95 | 0.99 | 1.05 | 1.06 | 0.97 | 0.91 | 1.00 | Normal |
| 38 | 1.03 | 1.02 | 1.01 | 1.01 | 0.99 | 1.08 | 0.92 | 0.95 | 1.00 | Normal |
| 39 | 1.01 | 1.00 | 1.01 | 1.06 | 1.00 | 1.04 | 0.95 | 0.99 | 1.00 | Normal |
| 40 | 1.02 | 1.02 | 0.92 | 1.08 | 0.99 | 1.09 | 0.92 | 0.98 | 1.00 | Normal |
| 41 | 0.99 | 1.02 | 0.95 | 1.02 | 0.98 | 0.98 | 0.94 | 0.92 | 1.00 | Normal |
| 42 | 1.03 | 1.05 | 1.10 | 1.12 | 1.12 | 1.15 | 1.04 | 1.02 | 1.00 | Normal |
| 43 | 1.03 | 0.98 | 1.01 | 1.02 | 1.03 | 1.03 | 0.95 | 0.94 | 1.00 | Normal |
| 44 | 1.02 | 1.03 | 1.03 | 1.00 | 1.05 | 0.98 | 1.04 | 1.05 | 1.00 | Normal |
| 45 | 0.99 | 0.98 | 0.99 | 0.94 | 1.00 | 0.98 | 0.94 | 0.90 | 1.00 | Normal |

TABLE 3-continued

Result of testing aneuploid in the F1 variety of broccoli (raw data obtained by PCR based on the SYBR method (value calculated by the ΔΔCt method))

| individual No. | SYBR C1 C1/C9 ΔΔCt | SYBR C2 C2/C9 ΔΔCt | SYBR C3 C3/C9 ΔΔCt | SYBR C4 C4/C9 ΔΔCt | SYBR C5 C5/C9 ΔΔCt | SYBR C6 C6/C9 ΔΔCt | SYBR C7 C7/C9 ΔΔCt | SYBR C8 C8/C9 ΔΔCt | SYBR C9 C9/C9 ΔΔCt | results |
|---|---|---|---|---|---|---|---|---|---|---|
| 46 | 1.11 | 1.11 | 1.10 | 1.05 | 1.03 | 1.06 | 1.02 | 1.05 | 1.00 | Normal |
| 47 | 0.99 | 1.02 | 1.00 | 1.07 | 1.03 | 1.01 | 1.06 | 1.07 | 1.00 | Normal |
| 48 | 0.98 | 0.97 | 0.94 | 1.05 | 0.99 | 1.05 | 0.97 | 1.00 | 1.00 | Normal |
| 49 | 1.00 | 1.00 | 0.97 | 0.98 | 1.01 | 1.05 | 0.93 | 0.91 | 1.00 | Normal |
| 50 | 1.12 | 1.10 | 1.01 | 1.09 | 0.93 | 1.14 | 0.93 | 1.00 | 1.00 | Normal |
| 51 | 1.01 | 1.02 | 0.99 | 1.02 | 1.00 | 1.12 | 0.95 | 1.00 | 1.00 | Normal |
| 52 | 1.01 | 1.00 | 0.94 | 1.01 | 1.01 | 1.00 | 0.94 | 0.94 | 1.00 | Normal |
| 53 | 1.03 | 1.05 | 1.04 | 1.05 | 1.04 | 1.03 | 1.00 | 1.00 | 1.00 | Normal |
| 54 | 0.99 | 1.03 | 1.01 | 0.99 | 1.08 | 1.05 | 0.97 | 0.96 | 1.00 | Normal |
| 55 | 1.03 | 0.98 | 1.00 | 1.00 | 1.03 | 1.00 | 1.00 | 0.94 | 1.00 | Normal |
| 56 | 0.99 | 1.02 | 1.04 | 1.06 | 1.03 | 0.99 | 1.07 | 1.05 | 1.00 | Normal |
| 57 | 1.02 | 0.99 | 0.99 | 0.97 | 1.02 | 1.08 | 0.97 | 0.93 | 1.00 | Normal |
| 58 | 1.00 | 0.98 | 0.94 | 0.96 | 1.02 | 0.98 | 0.97 | 1.01 | 1.00 | Normal |
| 59 | 0.95 | 1.11 | 1.11 | 1.06 | 1.05 | 1.12 | 1.14 | 1.08 | 1.00 | Normal |
| 60 | 1.05 | 1.02 | 0.99 | 1.02 | 1.05 | 1.03 | 1.06 | 0.97 | 1.00 | Normal |
| 61 | 1.02 | 1.05 | 0.97 | 0.94 | 1.03 | 1.05 | 1.00 | 0.97 | 1.00 | Normal |
| 62 | 1.03 | 0.98 | 0.93 | 1.02 | 1.05 | 1.11 | 0.95 | 0.94 | 1.00 | Normal |
| 63 | 1.05 | 1.02 | 0.97 | 1.08 | 1.03 | 1.05 | 0.95 | 0.96 | 1.00 | Normal |
| 64 | 1.08 | 0.96 | 0.94 | 1.10 | 0.98 | 1.10 | 0.93 | 1.00 | 1.00 | Normal |
| 65 | 1.00 | 0.98 | 0.98 | 1.12 | 1.02 | 1.03 | 0.95 | 1.04 | 1.00 | Normal |
| 66 | 0.92 | 1.00 | 1.07 | 1.10 | 1.08 | 0.93 | 1.07 | 1.07 | 1.00 | Normal |
| 67 | 0.95 | 1.02 | 1.05 | 1.00 | 1.05 | 0.91 | 1.08 | 1.00 | 1.00 | Normal |
| 68 | 0.98 | 1.00 | 0.99 | 0.95 | 0.98 | 0.91 | 0.97 | 1.01 | 1.00 | Normal |
| 69 | 0.99 | 0.46 | 1.14 | 1.11 | 1.13 | 0.94 | 1.23 | 1.10 | 1.00 | aneuploid (others) |
| 70 | 0.99 | 0.97 | 0.95 | 1.02 | 1.00 | 1.03 | 0.94 | 0.98 | 1.00 | Normal |
| 71 | 1.09 | 1.10 | 0.95 | 1.05 | 1.03 | 1.11 | 0.97 | 1.02 | 1.00 | Normal |
| 72 | 1.09 | 1.04 | 1.01 | 1.07 | 1.12 | 1.07 | 0.99 | 1.04 | 1.00 | Normal |
| 73 | 1.04 | 0.96 | 0.95 | 1.05 | 1.03 | 1.07 | 0.97 | 1.00 | 1.00 | Normal |
| 74 | 1.00 | 1.05 | 1.03 | 1.09 | 1.10 | 1.08 | 1.04 | 1.10 | 1.00 | Normal |
| 75 | 0.99 | 1.01 | 0.93 | 1.11 | 1.00 | 1.01 | 1.49 | 1.01 | 1.00 | aneuploid (+C7) |
| 76 | 1.02 | 1.00 | 0.97 | 1.02 | 0.98 | 1.02 | 0.99 | 1.01 | 1.00 | Normal |
| 77 | 1.02 | 1.01 | 0.99 | 1.03 | 0.99 | 1.00 | 1.01 | 0.99 | 1.00 | Normal |
| 78 | 1.01 | 0.98 | 0.99 | 1.02 | 1.03 | 1.03 | 1.02 | 0.97 | 1.00 | Normal |
| 79 | 1.03 | 1.03 | 0.98 | 1.02 | 1.00 | 1.03 | 0.98 | 0.96 | 1.00 | Normal |
| 80 | 0.91 | 1.01 | 1.05 | 1.02 | 1.04 | 0.92 | 1.07 | 1.05 | 1.00 | Normal |
| 81 | 0.92 | 1.00 | 1.02 | 0.97 | 1.08 | 1.60 | 1.07 | 0.97 | 1.00 | aneuploid (+C6) |
| 82 | 0.96 | 0.99 | 0.99 | 1.00 | 1.06 | 0.97 | 1.08 | 1.08 | 1.00 | Normal |
| 83 | 1.05 | 1.00 | 0.97 | 1.09 | 1.01 | 1.00 | 0.99 | 1.00 | 1.00 | Normal |
| 84 | 1.03 | 1.03 | 1.01 | 1.04 | 1.10 | 1.05 | 1.00 | 0.97 | 1.00 | Normal |
| 85 | 0.61 | 0.65 | 0.66 | 0.65 | 0.67 | 0.64 | 0.67 | 0.68 | 1.00 | aneuploid (+C9) |
| 86 | 0.96 | 1.01 | 0.96 | 1.06 | 1.00 | 1.00 | 0.98 | 0.93 | 1.00 | Normal |
| 87 | 1.03 | 1.01 | 0.94 | 1.05 | 1.01 | 1.04 | 0.97 | 1.00 | 1.00 | Normal |
| 88 | 1.00 | 0.95 | 0.95 | 1.01 | 1.00 | 1.02 | 0.95 | 1.04 | 1.00 | Normal |
| 89 | 0.93 | 0.92 | 0.95 | 1.08 | 0.94 | 0.92 | 0.93 | 1.02 | 1.00 | Normal |
| 90 | 1.00 | 0.98 | 1.04 | 1.01 | 1.00 | 1.04 | 1.00 | 1.05 | 1.00 | Normal |
| 91 | 1.11 | 1.12 | 1.13 | 1.12 | 1.14 | 1.13 | 1.10 | 1.12 | 1.00 | Normal |
| 92 | 1.01 | 1.00 | 0.95 | 1.02 | 0.97 | 1.00 | 0.94 | 1.00 | 1.00 | Normal |
| 93 | 1.02 | 0.98 | 0.96 | 0.98 | 0.99 | 1.03 | 0.97 | 0.96 | 1.00 | Normal |
| 94 | 0.96 | 0.99 | 1.01 | 0.94 | 0.99 | 1.00 | 0.97 | 0.98 | 1.00 | Normal |
| 95 | 1.00 | 1.01 | 0.98 | 1.00 | 0.98 | 0.99 | 0.96 | 1.05 | 1.00 | Normal |
| 96 | 1.04 | 1.07 | 1.09 | 0.99 | 0.99 | 1.05 | 0.98 | 1.00 | 1.00 | Normal |
| 97 | 1.03 | 1.00 | 1.07 | 1.05 | 1.08 | 1.06 | 1.02 | 1.00 | 1.00 | Normal |
| 98 | 1.07 | 1.14 | 1.07 | 1.13 | 1.05 | 1.15 | 1.00 | 1.05 | 1.00 | Normal |
| 99 | 1.03 | 0.98 | 0.99 | 1.01 | 0.98 | 0.94 | 0.97 | 1.00 | 1.00 | Normal |
| 100 | 0.96 | 0.97 | 1.10 | 1.08 | 1.06 | 0.93 | 1.11 | 1.09 | 1.00 | Normal |
| 101 | 0.97 | 0.98 | 1.01 | 0.93 | 1.03 | 1.03 | 1.02 | 0.96 | 1.00 | Normal |
| 102 | 1.03 | 0.96 | 1.02 | 0.96 | 1.00 | 0.95 | 0.96 | 1.03 | 1.00 | Normal |
| 103 | 1.04 | 1.00 | 1.05 | 0.99 | 1.01 | 1.03 | 1.02 | 0.98 | 1.00 | Normal |
| 104 | 1.08 | 1.07 | 1.01 | 0.98 | 1.03 | 1.02 | 0.97 | 0.96 | 1.00 | Normal |
| 105 | 1.02 | 1.01 | 0.98 | 0.94 | 0.99 | 0.98 | 0.95 | 0.96 | 1.00 | Normal |
| 106 | 0.96 | 1.00 | 1.05 | 1.02 | 1.07 | 0.95 | 1.66 | 1.04 | 1.00 | aneuploid (+C7) |
| 107 | 1.02 | 1.00 | 0.96 | 1.04 | 1.00 | 1.00 | 0.95 | 1.00 | 1.00 | Normal |
| 108 | 1.05 | 1.05 | 1.01 | 0.98 | 1.00 | 0.98 | 1.02 | 0.98 | 1.00 | Normal |
| 109 | 0.99 | 1.00 | 0.99 | 0.98 | 1.00 | 1.00 | 0.94 | 0.94 | 1.00 | Normal |
| 110 | 1.00 | 1.02 | 1.07 | 1.02 | 1.06 | 1.03 | 0.98 | 1.01 | 1.00 | Normal |
| 111 | 1.05 | 1.05 | 1.01 | 1.11 | 1.07 | 1.05 | 1.00 | 1.02 | 1.00 | Normal |
| 112 | 1.06 | 1.00 | 1.00 | 0.94 | 0.96 | 0.98 | 0.97 | 1.01 | 1.00 | Normal |
| 113 | 1.03 | 1.04 | 1.02 | 0.94 | 1.00 | 0.96 | 1.02 | 1.00 | 1.00 | Normal |
| 114 | 1.05 | 1.00 | 0.99 | 0.94 | 1.02 | 1.04 | 0.95 | 0.91 | 1.00 | Normal |
| 115 | 1.01 | 0.96 | 0.93 | 1.00 | 0.96 | 1.05 | 0.93 | 0.99 | 1.00 | Normal |
| 116 | 1.05 | 1.00 | 1.02 | 1.04 | 1.02 | 1.02 | 1.00 | 1.06 | 1.00 | Normal |
| 117 | 1.02 | 1.01 | 0.99 | 1.00 | 0.99 | 0.98 | 1.00 | 1.04 | 1.00 | Normal |

TABLE 3-continued

Result of testing aneuploid in the F1 variety of broccoli (raw data obtained by PCR based on the SYBR method (value calculated by the ΔΔCt method))

| individual No. | SYBR C1 C1/C9 ΔΔCt | SYBR C2 C2/C9 ΔΔCt | SYBR C3 C3/C9 ΔΔCt | SYBR C4 C4/C9 ΔΔCt | SYBR C5 C5/C9 ΔΔCt | SYBR C6 C6/C9 ΔΔCt | SYBR C7 C7/C9 ΔΔCt | SYBR C8 C8/C9 ΔΔCt | SYBR C9 C9/C9 ΔΔCt | results |
|---|---|---|---|---|---|---|---|---|---|---|
| 118 | 0.98 | 1.01 | 1.01 | 1.01 | 0.99 | 0.96 | 0.93 | 0.98 | 1.00 | Normal |
| 119 | 1.06 | 1.00 | 0.99 | 1.02 | 1.02 | 1.02 | 0.97 | 1.05 | 1.00 | Normal |
| 120 | 0.99 | 1.01 | 1.00 | 0.99 | 1.00 | 1.04 | 0.95 | 0.93 | 1.00 | Normal |
| 121 | 1.04 | 1.02 | 1.04 | 1.14 | 1.00 | 1.12 | 1.00 | 1.02 | 1.00 | Normal |
| 122 | 1.03 | 0.96 | 0.98 | 0.94 | 0.98 | 0.96 | 1.04 | 0.89 | 1.00 | Normal |
| 123 | 1.01 | 1.02 | 1.00 | 1.02 | 1.05 | 1.04 | 1.00 | 1.00 | 1.00 | Normal |
| 124 | 1.00 | 1.00 | 1.01 | 0.97 | 1.00 | 1.00 | 0.95 | 0.96 | 1.00 | Normal |
| 125 | 0.99 | 0.98 | 1.05 | 0.99 | 1.00 | 1.00 | 0.97 | 1.02 | 1.00 | Normal |
| 126 | 0.97 | 0.95 | 1.07 | 0.96 | 0.98 | 0.96 | 0.94 | 1.00 | 1.00 | Normal |
| 127 | 1.09 | 1.05 | 1.00 | 0.96 | 1.00 | 1.04 | 1.02 | 0.97 | 1.00 | Normal |
| 128 | 1.00 | 1.00 | 1.00 | 0.99 | 0.98 | 1.00 | 0.94 | 0.98 | 1.00 | Normal |
| 129 | 1.00 | 1.02 | 0.99 | 0.94 | 1.00 | 1.00 | 0.97 | 0.98 | 1.00 | Normal |
| 130 | 0.98 | 1.03 | 1.01 | 0.99 | 1.01 | 1.03 | 1.00 | 0.96 | 1.00 | Normal |
| 131 | 0.98 | 1.08 | 1.07 | 1.11 | 1.08 | 1.06 | 1.02 | 1.04 | 1.00 | Normal |
| 132 | 1.00 | 1.00 | 0.95 | 1.06 | 1.00 | 1.01 | 0.97 | 0.92 | 1.00 | Normal |
| 133 | 1.04 | 1.02 | 1.01 | 1.14 | 1.07 | 1.00 | 1.01 | 1.03 | 1.00 | Normal |
| 134 | 1.03 | 0.96 | 0.95 | 0.99 | 1.01 | 0.96 | 1.02 | 0.97 | 1.00 | Normal |
| 135 | 1.11 | 1.03 | 1.05 | 1.07 | 1.07 | 1.10 | 1.05 | 1.05 | 1.00 | Normal |
| 136 | 1.03 | 1.00 | 0.99 | 0.97 | 0.99 | 0.97 | 0.99 | 1.00 | 1.00 | Normal |
| 137 | 1.07 | 1.04 | 1.02 | 1.07 | 1.04 | 1.01 | 1.02 | 1.02 | 1.00 | Normal |
| 138 | 1.08 | 1.00 | 1.05 | 0.98 | 1.00 | 0.98 | 1.02 | 1.02 | 1.00 | Normal |
| 139 | 1.04 | 1.07 | 1.07 | 1.01 | 0.99 | 0.98 | 1.05 | 1.04 | 1.00 | Normal |
| 140 | 1.06 | 1.07 | 1.06 | 1.01 | 1.02 | 1.04 | 1.06 | 1.07 | 1.00 | Normal |
| 141 | 1.09 | 1.07 | 1.01 | 1.05 | 1.08 | 1.08 | 1.04 | 1.01 | 1.00 | Normal |
| 142 | 1.06 | 1.09 | 1.06 | 1.11 | 1.06 | 1.08 | 1.05 | 1.02 | 1.00 | Normal |
| 143 | 1.03 | 1.08 | 1.04 | 1.04 | 1.04 | 1.03 | 1.04 | 0.98 | 1.00 | Normal |
| 144 | 1.04 | 1.03 | 1.04 | 1.00 | 1.03 | 0.97 | 1.06 | 0.99 | 1.00 | Normal |
| 145 | 1.07 | 1.11 | 1.06 | 1.02 | 1.10 | 1.05 | 1.07 | 1.01 | 1.00 | Normal |
| 146 | 1.09 | 0.51 | 1.09 | 1.05 | 1.03 | 1.03 | 1.07 | 1.03 | 1.00 | aneuploid (others) |
| 147 | 1.03 | 0.97 | 0.97 | 1.03 | 0.96 | 0.99 | 0.95 | 1.00 | 1.00 | Normal |
| 148 | 1.14 | 1.14 | 1.09 | 1.08 | 1.12 | 1.08 | 1.10 | 1.07 | 1.00 | Normal |
| 149 | 0.95 | 0.96 | 1.04 | 0.99 | 1.05 | 0.99 | 1.05 | 1.02 | 1.00 | Normal |
| 150 | 0.98 | 1.01 | 1.01 | 1.02 | 1.06 | 1.00 | 1.05 | 1.11 | 1.00 | Normal |
| 151 | 1.05 | 1.02 | 1.00 | 1.08 | 1.03 | 1.13 | 0.97 | 1.04 | 1.00 | Normal |
| 152 | 0.96 | 1.02 | 1.05 | 1.02 | 1.04 | 0.98 | 1.50 | 1.02 | 1.00 | aneuploid (+C7) |
| 153 | 1.03 | 1.00 | 0.93 | 1.08 | 0.98 | 1.06 | 0.92 | 0.99 | 1.00 | Normal |
| 154 | 0.93 | 1.00 | 1.01 | 1.03 | 1.07 | 0.93 | 1.07 | 1.02 | 1.00 | Normal |
| 155 | 0.94 | 1.00 | 1.01 | 0.98 | 0.96 | 1.00 | 0.97 | 0.98 | 1.00 | Normal |
| 156 | 1.01 | 1.01 | 1.04 | 1.04 | 1.01 | 0.94 | 1.01 | 1.00 | 1.00 | Normal |
| 157 | 1.02 | 1.00 | 0.98 | 0.96 | 0.97 | 0.98 | 0.95 | 0.97 | 1.00 | Normal |
| 158 | 1.11 | 1.11 | 1.13 | 1.08 | 1.05 | 1.60 | 1.11 | 1.10 | 1.00 | aneuploid (+C6) |
| 159 | 0.98 | 1.02 | 0.93 | 1.00 | 0.95 | 0.99 | 0.95 | 0.94 | 1.00 | Normal |
| 160 | 1.00 | 0.99 | 1.00 | 0.96 | 1.00 | 0.91 | 0.99 | 0.97 | 1.00 | Normal |
| 161 | 1.00 | 1.02 | 0.97 | 0.98 | 1.37 | 1.60 | 0.92 | 1.00 | 1.00 | aneuploid (others) |
| 162 | 0.97 | 1.03 | 1.02 | 1.05 | 0.96 | 1.04 | 1.04 | 1.04 | 1.00 | Normal |
| 163 | 1.06 | 1.05 | 0.97 | 1.05 | 1.00 | 1.07 | 0.99 | 0.98 | 1.00 | Normal |
| 164 | 1.03 | 1.11 | 1.04 | 1.03 | 0.98 | 1.03 | 1.07 | 1.02 | 1.00 | Normal |
| 165 | 0.97 | 1.01 | 1.08 | 1.05 | 1.02 | 0.91 | 1.09 | 1.00 | 1.00 | Normal |
| 166 | 0.98 | 0.97 | 0.93 | 0.93 | 0.93 | 0.96 | 0.93 | 0.92 | 1.00 | Normal |
| 167 | 1.11 | 1.13 | 1.07 | 1.04 | 0.90 | 1.04 | 0.98 | 1.02 | 1.00 | Normal |
| 168 | 1.11 | 1.11 | 1.04 | 1.08 | 0.87 | 1.07 | 1.00 | 1.00 | 1.00 | Normal |
| 169 | 0.96 | 0.96 | 1.01 | 0.87 | 0.92 | 1.00 | 0.97 | 1.00 | 1.00 | Normal |
| 170 | 0.94 | 1.11 | 1.04 | 0.89 | 0.90 | 0.91 | 1.01 | 0.95 | 1.00 | Normal |
| 171 | 0.98 | 0.98 | 0.97 | 1.00 | 0.96 | 1.06 | 1.01 | 0.97 | 1.00 | Normal |
| 172 | 1.06 | 1.13 | 1.09 | 1.10 | 1.09 | 1.11 | 1.05 | 1.05 | 1.00 | Normal |
| 173 | 1.00 | 0.97 | 1.00 | 1.04 | 1.05 | 1.10 | 0.85 | 0.95 | 1.00 | Normal |
| 174 | 1.00 | 1.05 | 0.95 | 1.14 | 0.99 | 0.98 | 1.01 | 1.05 | 1.00 | Normal |
| 175 | 0.98 | 0.96 | 0.99 | 0.99 | 0.96 | 0.96 | 0.95 | 0.93 | 1.00 | Normal |
| 176 | 1.00 | 0.98 | 0.99 | 0.97 | 1.00 | 1.02 | 0.98 | 0.95 | 1.00 | Normal |
| 177 | 1.05 | 1.03 | 1.01 | 1.00 | 1.06 | 1.07 | 1.04 | 1.06 | 1.00 | Normal |
| 178 | 1.03 | 1.02 | 1.03 | 0.98 | 0.89 | 0.98 | 0.98 | 0.98 | 1.00 | Normal |
| 179 | 0.98 | 0.96 | 1.01 | 0.91 | 0.97 | 0.96 | 0.95 | 1.04 | 1.00 | Normal |
| 180 | 1.02 | 1.00 | 1.01 | 0.93 | 1.00 | 1.00 | 0.98 | 0.97 | 1.00 | Normal |
| 181 | 1.05 | 1.07 | 1.03 | 1.02 | 0.96 | 1.08 | 0.95 | 1.00 | 1.00 | Normal |
| 182 | 1.01 | 1.01 | 1.01 | 0.94 | 0.97 | 0.96 | 1.00 | 0.96 | 1.00 | Normal |
| 183 | 1.07 | 1.02 | 1.04 | 1.00 | 1.00 | 1.03 | 1.01 | 0.99 | 1.00 | Normal |
| 184 | 0.98 | 1.04 | 0.99 | 1.02 | 0.96 | 1.08 | 0.95 | 0.96 | 1.00 | Normal |
| 185 | 1.08 | 1.11 | 1.06 | 1.06 | 1.02 | 1.11 | 1.00 | 1.04 | 1.00 | Normal |
| 186 | 0.98 | 1.07 | 1.05 | 1.06 | 0.99 | 1.06 | 1.01 | 1.07 | 1.00 | Normal |
| 187 | 1.00 | 1.03 | 1.03 | 1.00 | 1.03 | 1.06 | 1.04 | 1.00 | 1.00 | Normal |
| 188 | 1.03 | 1.04 | 1.01 | 1.07 | 1.00 | 1.01 | 1.05 | 1.06 | 1.00 | Normal |
| 189 | 1.06 | 0.98 | 1.00 | 0.96 | 0.98 | 0.92 | 1.06 | 0.96 | 1.00 | Normal |

TABLE 3-continued

Result of testing aneuploid in the F1 variety of broccoli (raw data obtained by PCR based on the SYBR method (value calculated by the ΔΔCt method))

| individual No. | SYBR C1 C1/C9 ΔΔCt | SYBR C2 C2/C9 ΔΔCt | SYBR C3 C3/C9 ΔΔCt | SYBR C4 C4/C9 ΔΔCt | SYBR C5 C5/C9 ΔΔCt | SYBR C6 C6/C9 ΔΔCt | SYBR C7 C7/C9 ΔΔCt | SYBR C8 C8/C9 ΔΔCt | SYBR C9 C9/C9 ΔΔCt | results |
|---|---|---|---|---|---|---|---|---|---|---|
| 190 | 1.11 | 1.08 | 1.09 | 1.00 | 0.98 | 1.05 | 1.06 | 1.05 | 1.00 | Normal |
| 191 | 1.02 | 1.05 | 1.04 | 0.96 | 1.03 | 0.95 | 1.00 | 1.05 | 1.00 | Normal |
| 192 | 0.99 | 1.01 | 1.04 | 1.00 | 1.00 | 0.97 | 0.97 | 1.06 | 1.00 | Normal |
| 193 | 1.10 | 1.07 | 1.02 | 0.96 | 0.99 | 1.03 | 1.02 | 1.00 | 1.00 | Normal |
| 194 | 1.03 | 1.00 | 1.04 | 0.99 | 0.94 | 1.01 | 1.07 | 1.02 | 1.00 | Normal |
| 195 | 1.03 | 1.54 | 1.01 | 0.93 | 0.89 | 1.03 | 1.02 | 0.96 | 1.00 | aneuploid (+C2) |
| 196 | 0.98 | 1.00 | 0.97 | 0.99 | 0.99 | 0.99 | 1.00 | 0.93 | 1.00 | Normal |
| 197 | 1.00 | 1.04 | 0.95 | 1.00 | 1.00 | 1.00 | 0.96 | 0.94 | 1.00 | Normal |
| 198 | 1.04 | 1.05 | 1.04 | 1.04 | 1.02 | 1.11 | 0.99 | 1.03 | 1.00 | Normal |
| 199 | 1.01 | 1.02 | 0.95 | 0.44 | 0.89 | 0.98 | 0.93 | 0.90 | 1.00 | aneuploid (others) |
| 200 | 1.02 | 0.99 | 0.97 | 0.91 | 0.95 | 0.95 | 0.99 | 0.99 | 1.00 | Normal |
| 201 | 0.94 | 0.95 | 0.97 | 0.91 | 0.96 | 0.91 | 0.90 | 0.92 | 1.00 | Normal |
| 202 | 1.06 | 1.06 | 1.01 | 1.03 | 1.03 | 1.05 | 1.02 | 1.00 | 1.00 | Normal |
| 203 | 1.02 | 1.05 | 1.01 | 0.92 | 0.98 | 0.99 | 1.01 | 1.00 | 1.00 | Normal |
| 204 | 1.04 | 1.05 | 1.05 | 0.98 | 0.97 | 1.00 | 1.02 | 0.96 | 1.00 | Normal |
| 205 | 1.03 | 1.00 | 0.95 | 1.00 | 1.03 | 1.05 | 0.97 | 1.00 | 1.00 | Normal |
| 206 | 1.04 | 1.05 | 0.99 | 0.98 | 1.05 | 1.03 | 1.06 | 1.00 | 1.00 | Normal |
| 207 | 0.98 | 1.02 | 0.97 | 0.96 | 0.96 | 0.97 | 0.97 | 0.92 | 1.00 | Normal |
| 208 | 0.98 | 1.11 | 0.99 | 1.03 | 1.01 | 0.97 | 0.95 | 1.06 | 1.00 | Normal |
| 209 | 1.05 | 1.03 | 1.00 | 0.98 | 1.01 | 1.00 | 1.01 | 0.94 | 1.00 | Normal |
| 210 | 1.00 | 1.05 | 1.07 | 0.92 | 0.91 | 0.98 | 1.00 | 1.04 | 1.00 | Normal |
| 211 | 1.11 | 1.08 | 1.12 | 1.03 | 1.06 | 1.01 | 1.11 | 1.09 | 1.00 | Normal |
| 212 | 1.00 | 1.02 | 0.99 | 0.96 | 1.01 | 0.96 | 0.97 | 0.95 | 1.00 | Normal |
| 213 | 0.98 | 1.05 | 1.01 | 0.96 | 1.03 | 1.01 | 1.04 | 0.98 | 1.00 | Normal |
| 214 | 1.05 | 1.09 | 0.99 | 0.99 | 1.02 | 1.00 | 1.00 | 0.96 | 1.00 | Normal |
| 215 | 1.00 | 0.98 | 0.97 | 1.01 | 1.02 | 0.96 | 0.98 | 1.02 | 1.00 | Normal |
| 216 | 0.98 | 1.04 | 0.97 | 0.96 | 1.00 | 0.98 | 0.96 | 1.03 | 1.00 | Normal |
| 217 | 0.98 | 1.02 | 1.00 | 1.02 | 1.03 | 0.94 | 1.02 | 0.97 | 1.00 | Normal |
| 218 | 1.03 | 1.00 | 1.00 | 1.02 | 1.01 | 0.95 | 1.00 | 1.08 | 1.00 | Normal |
| 219 | 1.13 | 0.98 | 0.97 | 0.99 | 0.97 | 0.96 | 0.95 | 1.04 | 1.00 | Normal |
| 220 | 1.01 | 0.97 | 0.98 | 0.92 | 0.94 | 0.96 | 0.93 | 0.91 | 1.00 | Normal |
| 221 | 1.11 | 1.10 | 1.06 | 1.03 | 1.08 | 1.06 | 0.98 | 1.05 | 1.00 | Normal |
| 222 | 0.98 | 1.00 | 1.00 | 1.00 | 1.05 | 0.98 | 0.95 | 1.04 | 1.00 | Normal |
| 223 | 1.03 | 0.96 | 0.95 | 1.05 | 0.96 | 0.91 | 0.97 | 1.05 | 1.00 | Normal |
| 224 | 0.97 | 1.06 | 0.99 | 1.02 | 1.00 | 1.03 | 0.97 | 1.05 | 1.00 | Normal |
| 225 | 1.03 | 1.02 | 1.04 | 1.11 | 1.04 | 1.05 | 0.94 | 1.01 | 1.00 | Normal |
| 226 | 0.98 | 1.03 | 0.95 | 1.00 | 1.03 | 1.02 | 1.02 | 1.00 | 1.00 | Normal |
| 227 | 0.99 | 0.94 | 0.96 | 1.03 | 0.97 | 0.98 | 0.97 | 1.02 | 1.00 | Normal |
| 228 | 1.00 | 0.97 | 0.99 | 1.08 | 0.99 | 0.98 | 1.01 | 1.01 | 1.00 | Normal |
| 229 | 1.04 | 0.97 | 0.99 | 0.98 | 0.98 | 0.94 | 1.00 | 1.00 | 1.00 | Normal |
| 230 | 1.03 | 1.05 | 1.10 | 1.04 | 1.01 | 0.98 | 1.04 | 1.03 | 1.00 | Normal |
| 231 | 1.05 | 1.02 | 1.04 | 1.00 | 0.97 | 0.98 | 1.00 | 1.02 | 1.00 | Normal |
| 232 | 1.00 | 0.97 | 0.95 | 0.93 | 0.96 | 0.94 | 0.97 | 1.03 | 1.00 | Normal |
| 233 | 1.05 | 1.06 | 1.04 | 0.97 | 1.05 | 1.05 | 1.00 | 0.96 | 1.00 | Normal |
| 234 | 1.13 | 1.08 | 0.99 | 1.11 | 1.02 | 1.00 | 0.96 | 1.02 | 1.00 | Normal |
| 235 | 0.94 | 0.99 | 1.04 | 0.99 | 1.03 | 0.99 | 0.99 | 0.98 | 1.00 | Normal |
| 236 | 0.99 | 1.02 | 1.01 | 0.97 | 1.03 | 1.00 | 1.00 | 0.97 | 1.00 | Normal |
| 237 | 1.07 | 1.03 | 1.00 | 1.06 | 1.00 | 1.10 | 0.83 | 0.97 | 1.00 | Normal |
| 238 | 1.03 | 1.00 | 1.01 | 1.00 | 1.01 | 1.00 | 0.99 | 0.99 | 1.00 | Normal |
| 239 | 1.06 | 1.01 | 1.02 | 1.01 | 0.99 | 1.00 | 1.00 | 1.00 | 1.00 | Normal |
| 240 | 1.03 | 1.02 | 1.04 | 1.00 | 0.91 | 0.96 | 1.02 | 1.00 | 1.00 | Normal |
| 241 | 1.10 | 1.04 | 1.05 | 1.02 | 0.97 | 1.03 | 1.01 | 1.02 | 1.00 | Normal |
| 242 | 1.05 | 1.08 | 1.12 | 1.00 | 1.00 | 1.10 | 1.02 | 1.07 | 1.00 | Normal |
| 243 | 0.98 | 0.95 | 0.99 | 0.92 | 0.94 | 0.95 | 0.98 | 0.94 | 1.00 | Normal |
| 244 | 1.05 | 1.03 | 1.04 | 0.98 | 1.06 | 0.98 | 1.04 | 1.00 | 1.00 | Normal |
| 245 | 1.00 | 1.04 | 1.07 | 1.02 | 1.11 | 1.40 | 1.09 | 1.05 | 1.00 | aneuploid (+C6) |
| 246 | 0.98 | 0.98 | 1.01 | 1.00 | 1.00 | 0.97 | 0.97 | 0.94 | 1.00 | Normal |
| 247 | 1.00 | 1.00 | 1.04 | 1.01 | 1.06 | 1.00 | 1.03 | 0.97 | 1.00 | Normal |
| 248 | 1.00 | 1.02 | 0.99 | 0.96 | 1.00 | 1.02 | 0.97 | 1.02 | 1.00 | Normal |
| 249 | 0.95 | 0.92 | 0.94 | 0.97 | 0.95 | 0.96 | 0.95 | 0.91 | 1.00 | Normal |
| 250 | 0.96 | 0.99 | 1.06 | 1.05 | 1.05 | 0.90 | 1.07 | 1.02 | 1.00 | Normal |
| 251 | 1.03 | 0.94 | 1.02 | 1.00 | 1.03 | 1.03 | 1.00 | 1.03 | 1.00 | Normal |
| 252 | 0.96 | 0.96 | 0.98 | 0.96 | 1.00 | 1.00 | 0.95 | 1.02 | 1.00 | Normal |
| 253 | 0.98 | 1.02 | 1.04 | 0.96 | 1.00 | 0.98 | 0.96 | 0.92 | 1.00 | Normal |
| 254 | 1.05 | 1.11 | 1.04 | 1.00 | 1.05 | 1.03 | 1.04 | 0.38 | 1.00 | Normal |
| 255 | 1.08 | 1.03 | 1.05 | 1.09 | 1.02 | 1.05 | 1.00 | 1.06 | 1.00 | Normal |
| 256 | 0.98 | 1.05 | 1.03 | 1.02 | 1.02 | 1.05 | 1.03 | 0.94 | 1.00 | Normal |
| 257 | 1.01 | 0.97 | 0.99 | 0.98 | 1.02 | 1.00 | 0.97 | 0.96 | 1.00 | Normal |
| 258 | 0.97 | 1.00 | 0.95 | 1.00 | 1.05 | 1.02 | 1.04 | 0.96 | 1.00 | Normal |
| 259 | 1.00 | 0.98 | 0.97 | 1.12 | 0.98 | 1.03 | 0.95 | 1.03 | 1.00 | Normal |
| 260 | 1.01 | 0.98 | 0.99 | 0.98 | 0.98 | 1.05 | 1.00 | 0.99 | 1.00 | Normal |
| 261 | 0.98 | 0.99 | 0.99 | 0.94 | 1.00 | 0.94 | 1.01 | 1.08 | 1.00 | Normal |

TABLE 3-continued

Result of testing aneuploid in the F1 variety of broccoli (raw data obtained by PCR based on the SYBR method (value calculated by the ΔΔCt method))

| individual No. | SYBR C1 C1/C9 ΔΔCt | SYBR C2 C2/C9 ΔΔCt | SYBR C3 C3/C9 ΔΔCt | SYBR C4 C4/C9 ΔΔCt | SYBR C5 C5/C9 ΔΔCt | SYBR C6 C6/C9 ΔΔCt | SYBR C7 C7/C9 ΔΔCt | SYBR C8 C8/C9 ΔΔCt | SYBR C9 C9/C9 ΔΔCt | results |
|---|---|---|---|---|---|---|---|---|---|---|
| 262 | 0.96 | 1.01 | 0.95 | 0.96 | 0.99 | 0.94 | 0.99 | 0.95 | 1.00 | Normal |
| 263 | 1.03 | 0.96 | 0.91 | 0.92 | 0.94 | 0.96 | 0.93 | 0.92 | 1.00 | Normal |
| 264 | 1.05 | 1.03 | 1.01 | 0.98 | 0.99 | 0.96 | 1.06 | 0.98 | 1.00 | Normal |
| 265 | 0.98 | 1.07 | 0.99 | 1.05 | 0.99 | 1.05 | 1.01 | 1.08 | 1.00 | Normal |
| 266 | 0.98 | 1.00 | 0.95 | 0.97 | 0.96 | 0.98 | 0.97 | 0.97 | 1.00 | Normal |
| 267 | 1.02 | 1.07 | 1.05 | 1.02 | 1.00 | 1.04 | 1.04 | 1.02 | 1.00 | Normal |
| 268 | 0.91 | 0.99 | 0.95 | 1.00 | 0.97 | 0.98 | 1.04 | 1.02 | 1.00 | Normal |
| 269 | 0.82 | 1.51 | 0.95 | 1.00 | 0.96 | 0.91 | 0.95 | 0.98 | 1.00 | aneuploid (+C2) |
| 270 | 1.09 | 1.11 | 1.06 | 1.11 | 1.12 | 1.13 | 1.09 | 1.09 | 1.00 | Normal |
| 271 | 0.99 | 1.01 | 0.99 | 1.04 | 1.00 | 1.00 | 1.02 | 1.02 | 1.00 | Normal |
| 272 | 0.99 | 0.97 | 0.97 | 1.01 | 1.01 | 1.54 | 0.97 | 1.05 | 1.00 | aneuploid (+C6) |
| 273 | 1.01 | 0.98 | 0.93 | 0.92 | 0.98 | 1.00 | 0.93 | 1.02 | 1.00 | Normal |
| 274 | 0.94 | 0.95 | 0.93 | 0.85 | 0.90 | 0.93 | 0.95 | 0.89 | 1.00 | Normal |
| 275 | 0.99 | 0.95 | 0.96 | 0.89 | 0.91 | 0.94 | 0.96 | 0.98 | 1.00 | Normal |
| 276 | 0.96 | 0.98 | 0.95 | 1.00 | 1.00 | 0.96 | 0.95 | 1.04 | 1.00 | Normal |
| 277 | 0.97 | 1.00 | 0.98 | 0.93 | 0.98 | 0.95 | 1.00 | 1.03 | 1.00 | Normal |
| 278 | 0.93 | 0.96 | 1.02 | 0.94 | 0.98 | 0.96 | 0.97 | 0.98 | 1.00 | Normal |
| 279 | 0.96 | 0.99 | 0.98 | 0.93 | 1.00 | 0.98 | 0.95 | 0.94 | 1.00 | Normal |
| 280 | 0.96 | 1.02 | 1.02 | 1.00 | 1.00 | 0.98 | 1.08 | 1.08 | 1.00 | Normal |
| 281 | 1.00 | 0.95 | 0.93 | 0.96 | 0.97 | 0.98 | 0.97 | 0.94 | 1.00 | Normal |
| 282 | 0.96 | 0.99 | 0.97 | 1.00 | 1.00 | 0.98 | 1.02 | 1.04 | 1.00 | Normal |
| 283 | 0.99 | 0.91 | 0.90 | 0.96 | 0.93 | 0.92 | 0.89 | 0.94 | 1.00 | Normal |
| 284 | 0.96 | 0.90 | 0.92 | 0.98 | 0.87 | 0.97 | 0.87 | 0.95 | 1.00 | Normal |
| 285 | 0.96 | 0.94 | 0.95 | 0.93 | 0.99 | 0.96 | 0.96 | 0.94 | 1.00 | Normal |
| 286 | 1.03 | 0.96 | 0.97 | 0.94 | 1.01 | 0.96 | 1.02 | 0.98 | 1.00 | Normal |
| 287 | 0.92 | 0.98 | 0.95 | 0.96 | 0.98 | 0.96 | 1.02 | 1.08 | 1.00 | Normal |
| 288 | 0.92 | 0.98 | 1.10 | 0.97 | 0.96 | 1.00 | 0.97 | 1.04 | 1.00 | Normal |
| 289 | 1.00 | 1.04 | 0.99 | 0.96 | 1.01 | 0.96 | 1.03 | 0.97 | 1.00 | Normal |
| 290 | 0.97 | 1.01 | 0.97 | 0.99 | 1.00 | 1.02 | 1.00 | 1.00 | 1.00 | Normal |
| 291 | 1.02 | 1.01 | 1.01 | 0.96 | 0.98 | 1.02 | 1.03 | 1.05 | 1.00 | Normal |
| 292 | 0.90 | 1.01 | 0.93 | 0.95 | 0.98 | 0.92 | 1.04 | 1.00 | 1.00 | Normal |
| 293 | 0.94 | 0.99 | 0.93 | 0.99 | 0.96 | 0.99 | 0.97 | 0.94 | 1.00 | Normal |
| 294 | 0.96 | 1.00 | 0.99 | 1.00 | 0.99 | 0.96 | 1.02 | 0.96 | 1.00 | Normal |
| 295 | 0.98 | 0.92 | 0.98 | 0.93 | 0.97 | 0.93 | 0.95 | 0.92 | 1.00 | Normal |
| 296 | 0.92 | 0.98 | 0.94 | 0.92 | 0.96 | 0.96 | 0.99 | 0.93 | 1.00 | Normal |
| 297 | 0.91 | 1.00 | 1.04 | 0.93 | 1.03 | 0.91 | 1.07 | 1.04 | 1.00 | Normal |
| 298 | 0.94 | 1.05 | 0.97 | 1.06 | 0.98 | 0.95 | 0.95 | 1.00 | 1.00 | Normal |
| 299 | 0.98 | 0.98 | 0.93 | 0.94 | 0.94 | 0.91 | 0.95 | 0.98 | 1.00 | Normal |
| 300 | 0.90 | 0.95 | 0.97 | 0.98 | 0.99 | 0.96 | 1.05 | 1.05 | 1.00 | Normal |
| 301 | 0.98 | 0.99 | 0.99 | 0.93 | 0.96 | 0.93 | 0.99 | 0.96 | 1.00 | Normal |
| 302 | 0.96 | 0.96 | 0.98 | 0.96 | 1.00 | 1.01 | 1.01 | 0.98 | 1.00 | Normal |
| 303 | 0.95 | 0.98 | 1.00 | 0.92 | 0.96 | 0.96 | 1.00 | 0.94 | 1.00 | Normal |
| 304 | 0.99 | 1.00 | 0.93 | 0.96 | 0.96 | 0.98 | 0.99 | 0.97 | 1.00 | Normal |
| 305 | 0.96 | 0.96 | 1.00 | 1.05 | 0.98 | 1.05 | 0.95 | 0.99 | 1.00 | Normal |
| 306 | 0.92 | 0.92 | 0.95 | 0.92 | 0.93 | 0.89 | 0.94 | 0.94 | 1.00 | Normal |
| 307 | 1.00 | 1.05 | 0.99 | 1.02 | 0.96 | 1.03 | 0.99 | 1.05 | 1.00 | Normal |
| 308 | 0.89 | 0.91 | 0.93 | 0.91 | 0.98 | 0.89 | 0.96 | 1.05 | 1.00 | Normal |
| 309 | 0.92 | 0.99 | 1.00 | 0.94 | 0.98 | 0.96 | 1.05 | 1.04 | 1.00 | Normal |
| 310 | 0.58 | 0.60 | 0.60 | 0.57 | 0.59 | 0.57 | 0.59 | 0.63 | 1.00 | aneuploid (+C9) |
| 311 | 0.95 | 0.94 | 0.91 | 0.89 | 0.93 | 0.93 | 0.95 | 0.94 | 1.00 | Normal |
| 312 | 0.95 | 0.97 | 1.02 | 0.92 | 0.93 | 0.96 | 1.00 | 0.98 | 1.00 | Normal |
| 313 | 0.92 | 0.94 | 1.04 | 1.01 | 0.98 | 0.93 | 1.01 | 1.01 | 1.00 | Normal |
| 314 | 0.95 | 1.01 | 1.01 | 0.98 | 0.99 | 0.96 | 1.05 | 1.08 | 1.00 | Normal |
| 315 | 1.02 | 1.00 | 1.00 | 0.99 | 1.00 | 0.96 | 1.04 | 1.03 | 1.00 | Normal |
| 316 | 0.95 | 0.94 | 0.97 | 1.00 | 1.00 | 1.01 | 1.01 | 1.08 | 1.00 | Normal |
| 317 | 0.98 | 0.98 | 0.97 | 1.02 | 1.00 | 1.05 | 0.92 | 1.08 | 1.00 | Normal |
| 318 | 0.96 | 0.99 | 1.01 | 0.95 | 0.97 | 0.93 | 1.03 | 1.02 | 1.00 | Normal |
| 319 | 0.95 | 0.94 | 0.94 | 0.92 | 0.95 | 0.94 | 0.96 | 0.96 | 1.00 | Normal |
| 320 | 1.01 | 0.96 | 0.96 | 0.92 | 0.95 | 0.94 | 1.01 | 0.97 | 1.00 | Normal |
| 321 | 0.92 | 0.90 | 0.97 | 0.85 | 0.95 | 0.89 | 1.02 | 0.96 | 1.00 | Normal |
| 322 | 0.99 | 0.95 | 0.97 | 1.05 | 0.98 | 0.99 | 1.00 | 1.06 | 1.00 | Normal |
| 323 | 1.03 | 1.06 | 1.01 | 0.93 | 0.96 | 1.02 | 0.97 | 1.02 | 1.00 | Normal |
| 324 | 1.00 | 1.00 | 0.96 | 0.92 | 1.01 | 0.98 | 1.03 | 0.99 | 1.00 | Normal |
| 325 | 1.03 | 1.07 | 1.07 | 1.03 | 1.00 | 0.92 | 1.12 | 1.05 | 1.00 | Normal |
| 326 | 0.98 | 1.02 | 0.99 | 0.98 | 1.00 | 1.03 | 1.01 | 1.02 | 1.00 | Normal |
| 327 | 0.98 | 1.04 | 1.01 | 1.06 | 0.97 | 1.09 | 1.04 | 1.04 | 1.00 | Normal |
| 328 | 0.99 | 1.01 | 0.95 | 1.12 | 1.03 | 1.12 | 0.93 | 1.05 | 1.00 | Normal |
| 329 | 0.98 | 0.94 | 0.97 | 0.89 | 0.87 | 0.87 | 0.95 | 0.98 | 1.00 | Normal |
| 330 | 0.99 | 1.02 | 0.99 | 0.97 | 0.98 | 0.89 | 1.09 | 1.04 | 1.00 | Normal |
| 331 | 1.00 | 1.00 | 0.98 | 0.98 | 0.93 | 0.98 | 0.95 | 1.02 | 1.00 | Normal |
| 332 | 1.00 | 0.97 | 0.97 | 0.94 | 1.02 | 0.96 | 1.07 | 1.00 | 1.00 | Normal |
| 333 | 1.03 | 1.01 | 1.02 | 1.05 | 0.92 | 1.02 | 0.92 | 1.01 | 1.00 | Normal |

TABLE 3-continued

Result of testing aneuploid in the F1 variety of broccoli (raw data obtained by PCR based on the SYBR method (value calculated by the ΔΔCt method))

| individual No. | SYBR C1 C1/C9 ΔΔCt | SYBR C2 C2/C9 ΔΔCt | SYBR C3 C3/C9 ΔΔCt | SYBR C4 C4/C9 ΔΔCt | SYBR C5 C5/C9 ΔΔCt | SYBR C6 C6/C9 ΔΔCt | SYBR C7 C7/C9 ΔΔCt | SYBR C8 C8/C9 ΔΔCt | SYBR C9 C9/C9 ΔΔCt | results |
|---|---|---|---|---|---|---|---|---|---|---|
| 334 | 0.96 | 1.00 | 0.99 | 1.02 | 0.99 | 0.96 | 1.00 | 1.10 | 1.00 | Normal |
| 335 | 0.97 | 1.11 | 1.12 | 1.01 | 0.97 | 1.03 | 1.01 | 1.11 | 1.00 | Normal |
| 336 | 1.00 | 1.01 | 1.01 | 1.12 | 1.01 | 1.05 | 1.02 | 1.08 | 1.00 | Normal |
| 337 | 1.04 | 0.98 | 0.99 | 1.05 | 0.96 | 1.05 | 1.00 | 0.98 | 1.00 | Normal |
| 338 | 0.92 | 0.94 | 1.01 | 1.00 | 1.00 | 0.95 | 1.00 | 1.03 | 1.00 | Normal |
| 339 | 1.01 | 0.96 | 1.01 | 1.06 | 0.98 | 0.95 | 1.03 | 1.10 | 1.00 | Normal |
| 340 | 0.98 | 0.97 | 0.94 | 1.02 | 0.92 | 1.05 | 1.01 | 0.98 | 1.00 | Normal |
| 341 | 0.92 | 0.97 | 0.93 | 0.90 | 0.94 | 0.92 | 1.00 | 1.00 | 1.00 | Normal |
| 342 | 1.06 | 1.03 | 1.06 | 1.02 | 0.99 | 0.96 | 1.07 | 1.07 | 1.00 | Normal |
| 343 | 0.96 | 0.94 | 0.97 | 0.96 | 1.00 | 0.94 | 1.00 | 1.02 | 1.00 | Normal |
| 344 | 0.99 | 0.98 | 0.97 | 0.97 | 1.03 | 0.95 | 0.97 | 0.99 | 1.00 | Normal |
| 345 | 0.94 | 0.99 | 0.99 | 1.06 | 0.96 | 0.95 | 0.93 | 1.00 | 1.00 | Normal |
| 346 | 0.92 | 1.00 | 0.96 | 1.07 | 0.93 | 1.03 | 1.02 | 1.02 | 1.00 | Normal |
| 347 | 1.03 | 1.00 | 0.93 | 1.11 | 0.97 | 1.02 | 0.96 | 0.96 | 1.00 | Normal |
| 348 | 0.97 | 0.96 | 0.99 | 0.97 | 0.96 | 1.09 | 0.92 | 0.89 | 1.00 | Normal |
| 349 | 1.05 | 0.99 | 0.97 | 1.05 | 1.01 | 1.10 | 1.02 | 0.95 | 1.00 | Normal |
| 350 | 1.01 | 1.03 | 1.01 | 1.06 | 1.02 | 0.99 | 0.95 | 0.97 | 1.00 | Normal |
| 351 | 0.93 | 0.92 | 1.01 | 0.99 | 0.98 | 1.01 | 0.95 | 1.03 | 1.00 | Normal |
| 352 | 1.03 | 1.11 | 1.00 | 1.09 | 1.00 | 1.06 | 0.98 | 1.05 | 1.00 | Normal |
| 353 | 1.05 | 1.05 | 0.97 | 1.06 | 0.92 | 1.04 | 0.94 | 0.99 | 1.00 | Normal |
| 354 | 0.98 | 1.09 | 1.03 | 1.06 | 1.02 | 1.01 | 1.04 | 1.06 | 1.00 | Normal |
| 355 | 0.94 | 1.09 | 0.99 | 1.04 | 1.00 | 1.07 | 1.02 | 1.02 | 1.00 | Normal |
| 356 | 0.96 | 0.99 | 1.01 | 0.99 | 1.00 | 1.01 | 1.02 | 1.08 | 1.00 | Normal |
| 357 | 0.98 | 1.01 | 1.03 | 1.01 | 1.00 | 0.96 | 1.05 | 1.03 | 1.00 | Normal |
| 358 | 1.14 | 1.11 | 1.01 | 1.06 | 0.98 | 1.10 | 0.96 | 1.06 | 1.00 | Normal |
| 359 | 1.04 | 1.00 | 1.01 | 1.09 | 0.98 | 1.04 | 0.96 | 1.04 | 1.00 | Normal |
| 360 | 1.02 | 0.97 | 0.99 | 1.02 | 0.99 | 1.01 | 0.93 | 0.93 | 1.00 | Normal |
| 361 | 1.02 | 1.01 | 1.06 | 0.97 | 0.97 | 1.00 | 1.02 | 0.95 | 1.00 | Normal |
| 362 | 1.05 | 1.01 | 1.01 | 0.95 | 0.98 | 0.94 | 0.98 | 0.93 | 1.00 | Normal |
| 363 | 1.02 | 1.01 | 1.06 | 1.02 | 1.02 | 1.01 | 1.00 | 1.03 | 1.00 | Normal |
| 364 | 1.00 | 1.01 | 1.08 | 1.04 | 0.92 | 0.90 | 1.07 | 1.06 | 1.00 | Normal |
| 365 | 0.98 | 1.00 | 1.06 | 0.97 | 1.02 | 0.97 | 1.05 | 0.94 | 1.00 | Normal |
| 366 | 1.05 | 1.09 | 1.06 | 1.01 | 1.08 | 0.95 | 1.09 | 1.04 | 1.00 | Normal |
| 367 | 1.01 | 1.10 | 1.06 | 0.98 | 1.02 | 1.53 | 1.00 | 1.00 | 1.00 | aneuploid (+C6) |
| 368 | 1.00 | 0.97 | 1.02 | 0.95 | 0.98 | 0.99 | 1.04 | 0.97 | 1.00 | Normal |
| 369 | 1.00 | 1.00 | 1.07 | 1.05 | 1.01 | 0.99 | 1.02 | 1.03 | 1.00 | Normal |
| 370 | 0.99 | 0.98 | 0.95 | 0.98 | 0.97 | 1.03 | 0.94 | 0.98 | 1.00 | Normal |
| 371 | 0.96 | 0.95 | 0.94 | 0.96 | 0.99 | 1.08 | 0.90 | 0.91 | 1.00 | Normal |
| 372 | 1.02 | 1.04 | 1.06 | 0.99 | 1.04 | 1.00 | 0.88 | 0.99 | 1.00 | Normal |
| 373 | 0.96 | 1.01 | 0.99 | 0.99 | 0.99 | 0.91 | 1.07 | 0.99 | 1.00 | Normal |
| 374 | 0.98 | 0.99 | 0.97 | 0.96 | 0.96 | 1.04 | 0.96 | 0.94 | 1.00 | Normal |
| 375 | 1.02 | 1.06 | 1.10 | 1.02 | 1.08 | 0.97 | 1.10 | 1.03 | 1.00 | Normal |
| 376 | 1.02 | 1.04 | 1.01 | 1.09 | 1.05 | 0.99 | 1.07 | 1.02 | 1.00 | Normal |
| 377 | 1.30 | 0.99 | 1.01 | 1.00 | 0.99 | 1.06 | 1.01 | 0.94 | 1.00 | aneuploid (+C1) |
| 378 | 0.98 | 0.97 | 0.95 | 1.01 | 1.00 | 1.13 | 0.95 | 0.09 | 1.00 | Normal |
| 379 | 0.98 | 0.95 | 0.91 | 0.97 | 0.96 | 1.02 | 0.89 | 0.02 | 1.00 | Normal |
| 380 | 1.00 | 0.99 | 0.91 | 0.99 | 0.90 | 0.95 | 0.89 | 0.97 | 1.00 | Normal |
| 381 | 0.99 | 0.97 | 0.97 | 0.95 | 0.96 | 0.92 | 1.00 | 0.96 | 1.00 | Normal |
| 302 | 0.95 | 0.91 | 0.93 | 0.91 | 0.94 | 0.97 | 0.94 | 0.91 | 1.00 | Normal |
| 383 | 1.02 | 1.00 | 0.98 | 0.97 | 0.94 | 0.93 | 0.98 | 0.96 | 1.00 | Normal |
| 384 | 1.00 | 1.01 | 1.01 | 1.00 | 1.05 | 0.93 | 1.06 | 1.00 | 1.00 | Normal |
| 385 | 1.01 | 0.98 | 1.00 | 0.96 | 1.04 | 1.04 | 0.99 | 0.94 | 1.00 | Normal |
| 386 | 1.04 | 1.01 | 1.01 | 0.99 | 1.02 | 1.04 | 1.01 | 0.98 | 1.00 | Normal |
| 387 | 0.98 | 0.97 | 0.95 | 0.95 | 0.99 | 1.07 | 0.95 | 0.91 | 1.00 | Normal |
| 388 | 0.99 | 0.93 | 0.98 | 0.98 | 0.96 | 0.95 | 1.02 | 0.99 | 1.00 | Normal |
| 389 | 0.97 | 1.04 | 1.00 | 1.04 | 1.00 | 1.09 | 0.98 | 0.99 | 1.00 | Normal |
| 390 | 1.03 | 0.97 | 0.99 | 1.01 | 1.00 | 1.09 | 0.94 | 0.99 | 1.00 | Normal |
| 391 | 1.03 | 1.60 | 1.03 | 1.03 | 1.07 | 1.05 | 1.04 | 1.06 | 1.00 | aneuploid (+C2) |
| 392 | 0.96 | 0.95 | 0.98 | 0.95 | 0.98 | 0.91 | 0.98 | 0.93 | 1.00 | Normal |
| 393 | 1.01 | 1.02 | 1.09 | 1.05 | 1.02 | 0.91 | 1.07 | 1.11 | 1.00 | Normal |
| 394 | 1.02 | 0.99 | 0.97 | 0.97 | 1.02 | 0.93 | 0.98 | 0.95 | 1.00 | Normal |
| 395 | 1.02 | 1.06 | 0.99 | 1.05 | 1.03 | 1.02 | 0.98 | 1.01 | 1.00 | Normal |
| 396 | 0.95 | 1.03 | 0.98 | 0.99 | 1.00 | 0.93 | 1.05 | 1.11 | 1.00 | Normal |
| 397 | 1.02 | 1.04 | 1.01 | 1.04 | 1.01 | 1.13 | 1.05 | 1.02 | 1.00 | Normal |
| 398 | 0.94 | 0.93 | 0.91 | 0.91 | 0.99 | 1.08 | 0.90 | 0.89 | 1.00 | Normal |
| 399 | 1.05 | 0.97 | 1.01 | 1.03 | 1.03 | 1.12 | 1.00 | 0.97 | 1.00 | Normal |
| 400 | 1.02 | 0.95 | 0.99 | 1.06 | 0.98 | 1.02 | 1.00 | 0.99 | 1.00 | Normal |
| 401 | 1.06 | 0.98 | 0.99 | 1.02 | 1.06 | 1.04 | 0.97 | 0.99 | 1.00 | Normal |
| 402 | 0.96 | 1.03 | 1.08 | 0.97 | 1.02 | 0.96 | 1.03 | 0.99 | 1.00 | Normal |
| 403 | 1.02 | 1.01 | 1.03 | 1.00 | 1.02 | 1.06 | 1.00 | 0.94 | 1.00 | Normal |
| 404 | 1.07 | 1.06 | 1.04 | 1.03 | 1.01 | 1.01 | 1.02 | 1.01 | 1.00 | Normal |
| 405 | 1.04 | 0.94 | 0.96 | 0.92 | 0.96 | 0.94 | 0.98 | 0.99 | 1.00 | Normal |

TABLE 3-continued

Result of testing aneuploid in the F1 variety of broccoli (raw data obtained by PCR based on the SYBR method (value calculated by the ΔΔCt method))

| individual No. | SYBR C1 C1/C9 ΔΔCt | SYBR C2 C2/C9 ΔΔCt | SYBR C3 C3/C9 ΔΔCt | SYBR C4 C4/C9 ΔΔCt | SYBR C5 C5/C9 ΔΔCt | SYBR C6 C6/C9 ΔΔCt | SYBR C7 C7/C9 ΔΔCt | SYBR C8 C8/C9 ΔΔCt | SYBR C9 C9/C9 ΔΔCt | results |
|---|---|---|---|---|---|---|---|---|---|---|
| 406 | 1.10 | 1.09 | 1.01 | 1.04 | 1.05 | 1.10 | 1.02 | 1.05 | 1.00 | Normal |
| 407 | 1.00 | 0.99 | 0.99 | 0.95 | 1.04 | 1.04 | 1.02 | 0.97 | 1.00 | Normal |
| 408 | 1.01 | 0.98 | 0.97 | 1.06 | 1.02 | 1.05 | 1.02 | 1.09 | 1.00 | Normal |
| 400 | 1.03 | 0.99 | 0.99 | 1.03 | 0.94 | 1.06 | 0.96 | 0.97 | 1.00 | Normal |
| 410 | 1.01 | 0.97 | 0.99 | 0.97 | 1.00 | 1.01 | 0.99 | 0.96 | 1.00 | Normal |
| 411 | 1.00 | 1.02 | 1.02 | 1.00 | 1.02 | 1.04 | 0.97 | 0.96 | 1.00 | Normal |
| 412 | 1.04 | 0.99 | 1.06 | 1.07 | 1.07 | 1.09 | 1.05 | 1.12 | 1.00 | Normal |
| 413 | 1.03 | 1.63 | 1.02 | 1.01 | 1.03 | 1.05 | 1.06 | 1.01 | 1.00 | aneuploid (+C2) |
| 414 | 1.01 | 0.98 | 0.96 | 1.00 | 0.98 | 1.07 | 0.93 | 1.00 | 1.00 | Normal |
| 415 | 1.04 | 1.06 | 1.05 | 1.03 | 1.05 | 0.95 | 1.01 | 1.00 | 1.00 | Normal |
| 416 | 0.99 | 1.42 | 0.90 | 1.01 | 0.95 | 0.98 | 0.90 | 0.97 | 1.00 | aneuploid (+C2) |
| 417 | 1.10 | 1.03 | 0.95 | 1.13 | 0.99 | 1.15 | 0.92 | 0.98 | 1.00 | Normal |
| 418 | 1.00 | 1.03 | 0.99 | 1.06 | 0.97 | 1.08 | 0.92 | 1.00 | 1.00 | Normal |
| 419 | 0.96 | 0.95 | 1.00 | 0.98 | 0.98 | 1.02 | 0.96 | 0.91 | 1.00 | Normal |
| 420 | 1.06 | 0.93 | 0.95 | 1.00 | 0.96 | 1.05 | 0.94 | 0.87 | 1.00 | Normal |
| 421 | 0.99 | 0.93 | 0.97 | 1.06 | 0.95 | 1.07 | 0.92 | 1.00 | 1.00 | Normal |
| 422 | 0.97 | 0.97 | 1.00 | 1.14 | 1.02 | 1.07 | 0.94 | 0.99 | 1.00 | Normal |
| 423 | 0.62 | 0.63 | 0.65 | 0.66 | 0.65 | 0.69 | 0.66 | 0.66 | 1.00 | aneuploid (+C9) |
| 424 | 0.99 | 0.97 | 1.01 | 1.01 | 1.03 | 1.05 | 0.98 | 0.91 | 1.00 | Normal |
| 425 | 1.00 | 1.05 | 1.01 | 1.07 | 1.03 | 1.12 | 0.96 | 1.05 | 1.00 | Normal |
| 426 | 1.02 | 0.97 | 0.97 | 1.00 | 1.02 | 1.04 | 0.95 | 0.96 | 1.00 | Normal |
| 427 | 0.97 | 1.01 | 1.06 | 0.97 | 1.02 | 0.87 | 1.10 | 1.01 | 1.00 | Normal |
| 428 | 1.03 | 1.00 | 0.96 | 0.98 | 0.94 | 0.99 | 0.97 | 0.97 | 1.00 | Normal |
| 429 | 1.02 | 0.99 | 0.99 | 0.97 | 1.02 | 1.09 | 0.99 | 0.99 | 1.00 | Normal |
| 430 | 1.00 | 0.97 | 1.02 | 1.02 | 1.01 | 0.98 | 1.02 | 1.01 | 1.00 | Normal |
| 431 | 0.97 | 0.98 | 0.98 | 0.93 | 0.95 | 0.94 | 0.96 | 0.94 | 1.00 | Normal |
| 432 | 1.01 | 0.44 | 1.00 | 0.93 | 0.96 | 0.90 | 0.87 | 1.01 | 1.00 | aneuploid (others) |
| 433 | 1.01 | 1.03 | 0.96 | 0.99 | 0.96 | 0.93 | 0.96 | 1.02 | 1.00 | Normal |
| 434 | 0.98 | 0.95 | 0.99 | 0.91 | 1.01 | 0.93 | 1.05 | 0.97 | 1.00 | Normal |
| 435 | 1.02 | 1.01 | 0.93 | 1.01 | 0.97 | 1.02 | 0.96 | 1.03 | 1.00 | Normal |
| 436 | 0.97 | 0.98 | 1.01 | 0.91 | 0.99 | 1.01 | 1.01 | 1.10 | 1.00 | Normal |
| 437 | 0.96 | 0.97 | 0.99 | 0.95 | 1.00 | 0.99 | 1.00 | 0.95 | 1.00 | Normal |
| 438 | 0.98 | 0.97 | 0.97 | 0.93 | 0.97 | 0.98 | 0.98 | 0.99 | 1.00 | Normal |
| 439 | 1.09 | 1.01 | 0.98 | 1.01 | 0.99 | 0.99 | 1.58 | 1.03 | 1.00 | aneuploid (+C7) |
| 440 | 0.95 | 0.94 | 1.05 | 0.98 | 0.96 | 0.97 | 1.01 | 1.00 | 1.00 | Normal |
| 441 | 0.93 | 0.89 | 0.95 | 0.88 | 0.99 | 0.94 | 0.96 | 0.98 | 1.00 | Normal |
| 442 | 0.99 | 1.06 | 0.99 | 1.06 | 1.00 | 1.08 | 0.98 | 1.02 | 1.00 | Normal |
| 443 | 1.02 | 1.08 | 1.04 | 1.06 | 1.01 | 1.07 | 1.00 | 1.06 | 1.00 | Normal |
| 444 | 0.93 | 0.95 | 1.00 | 0.93 | 1.02 | 0.93 | 1.07 | 0.99 | 1.00 | Normal |
| 445 | 1.00 | 0.95 | 1.03 | 0.91 | 1.01 | 0.88 | 1.02 | 1.01 | 1.00 | Normal |

TABLE 4

Result of testing aneuploid in the F1 variety of broccoli by the SYBR method (summary)

| | Number of plants | ratio (%) |
|---|---|---|
| Normal | 418 | 93.9% |
| aneuploid (+C1) | 2 | 0.4% |
| aneuploid (+C2) | 5 | 1.1% |
| aneuploid (+C3) | 0 | 0.0% |
| aneuploid (+C4) | 1 | 0.2% |
| aneuploid (+C5) | 0 | 0.0% |
| aneuploid (+C6) | 5 | 1.1% |
| aneuploid (+C7) | 5 | 1.1% |
| aneuploid (+C8) | 0 | 0.0% |
| aneuploid (+C9) | 3 | 0.7% |
| aneuploid (others) | 6 | 1.3% |

Example 4 Example of Detection of Off-Type in Cauliflower

The seeds of the F1 variety of cauliflower "SCF-30" under development by SAKATA SEED CORPORATION were sown in a nursery tray. DNA was extracted from newly emerged cotyledons from germinating seeds of 654 individuals, then a real-time PCR was performed by the fluorescence probe method using markers specific to each chromosomes.

Specifically, the above process was performed as follows.

DNA was extracted from cotyledons of cauliflower in the same manner as in Example 3 described above.

The PCR test was performed using the chromosome-specific markers divided into the following three combinations:

Triplex including the chromosome 6 marker, the chromosome 4 marker, and the chromosome 2 marker;

Triplex including the chromosome 9 marker, the chromosome 3 marker, and the chromosome 8 marker; and Triplex including the chromosome 1 marker, the chromosome 5 marker, and the chromosome 7 marker.

As for the chromosome markers used herein, the primers and probes shown in Tables 1 and 2 were used for each of the chromosomes. For example, a pair of primers having the sequences shown in SEQ ID NOs: 1 and 2 and a probe having the sequence shown in SEQ ID NO: 19 were used as a chromosome 1 marker.

Regarding real-time PCR, the same machine as noted in Example 3 was used, and the PCR conditions of incubation at 95° C. for 1 minute, followed by 40 cycles of 2-step PCR at 95° C. for 15 seconds and 60° C. for 45 seconds were used. Filters with excitation wavelengths of 465 nm, 533 nm, 618 nm, and detection wavelengths 510 nm, 580 nm, and 660 nm were used for the measurement of signals of FAM, HEX, and Cy5, respectively.

Based on the Ct value obtained by the second derivative method, the relative quantification was calculated by the ΔΔCt method using the respective markers of chromosome 2, chromosome 8 and chromosome 7 as endogenous controls.

The results were as shown in Table 5.

These results are summarized in Table 5 and thus it is clear that the aneuploids are included at the ratio as shown in Table 6.

Figure 5:
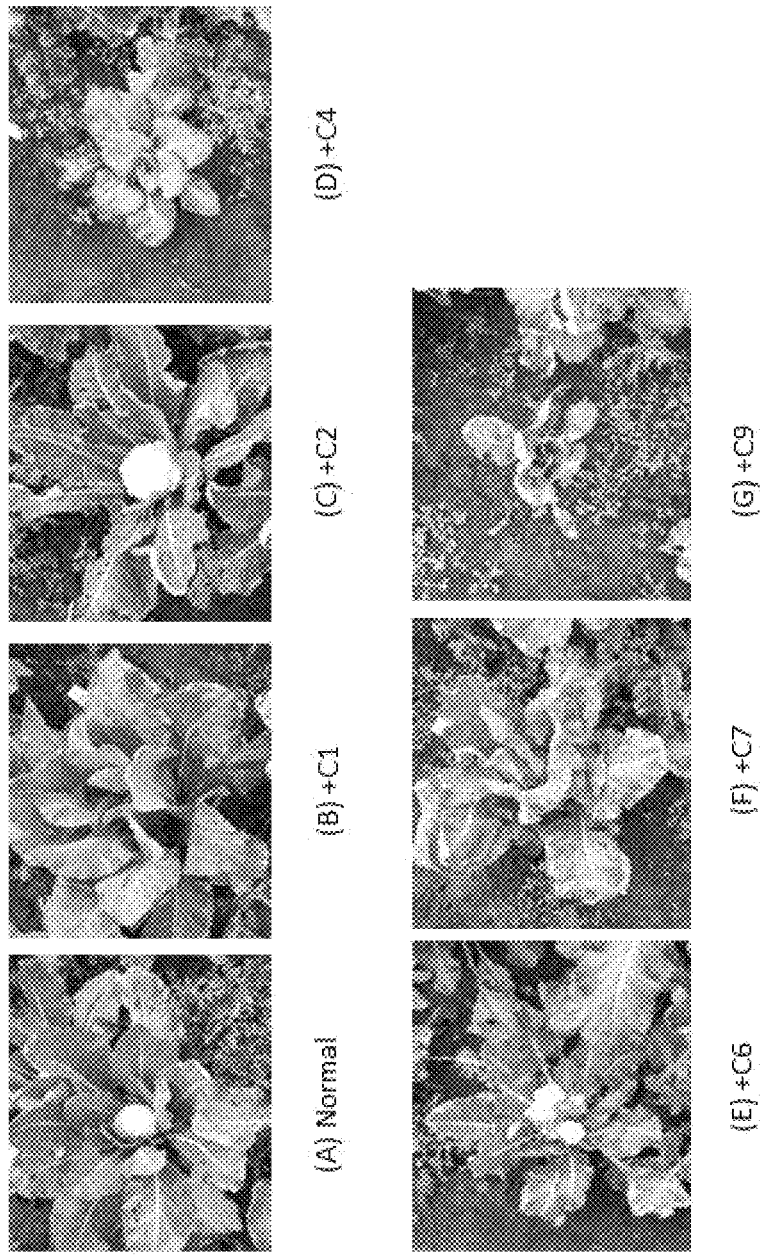
FIG. 5 shows phenotypes of aneuploids from cauliflower variety, where in the figure, (A) represents a normal individual (Normal), (B) represents chromosome 1 trisomy (+C1), (C) represents chromosome 2 trisomy (+C2), (D) represents chromosome 4 trisomy (+C4), (E) represents chromosome 6 trisomy (+C6), (F) represents chromosome 7 trisomy (+C7), and (G) represents chromosome 9 trisomy (+C9)

Furthermore, plants assumed to be aneuploids in this experiment were cultivated in the field to investigate the subsequent phenotype. Consistent with the case of broccoli, each of the aneuploids exhibited a characteristic appearance (FIG. 5) (the phenotypic characteristics of the chromosome trisomies were as shown in FIG. 7).

The above results indicate that, similar to broccoli, aneuploids appear in cauliflower and this method is an effective procedure for detecting these aneuploids in cauliflower.

TABLE 5

Result of testing aneuploid in the F1 variety of cauliflower (raw data obtained by multiplex PCR based on the fluorescent probe method (value calculated by the ΔΔCt method))

| individual No. | C6C4C2 triplex PCR | | | C9C3C8 triplex PCR | | | C1C5C7 triplex PCR | | | results |
|---|---|---|---|---|---|---|---|---|---|---|
| | C6 C6/C2 ΔΔCt | C4 C4/C2 ΔΔCt | C2 C2/C2 ΔΔCt | C9 C9/C8 ΔΔCt | C3 C3/C8 ΔΔCt | C8 C8/C8 ΔΔCt | C1 C1/C7 ΔΔCt | C5 C5/C7 ΔΔCt | C7 C7/C7 ΔΔCt | |
| 1 | 0.98 | 0.99 | 1.00 | 1.00 | 1.02 | 1.00 | 1.04 | 0.98 | 1.00 | Normal |
| 2 | 0.99 | 1.02 | 1.00 | 0.94 | 1.05 | 1.00 | 0.96 | 1.09 | 1.00 | Normal |
| 3 | 0.75 | 0.73 | 1.00 | 1.11 | 1.07 | 1.00 | 0.94 | 0.98 | 1.00 | aneuploid (+C2) |
| 4 | 0.98 | 0.94 | 1.00 | 1.02 | 1.06 | 1.00 | 1.12 | 1.09 | 1.00 | Normal |
| 5 | 1.03 | 1.02 | 1.00 | 0.99 | 0.89 | 1.00 | 0.78 | 0.77 | 1.00 | aneuploid (+C7) |
| 6 | 0.95 | 0.97 | 1.00 | 0.98 | 1.03 | 1.00 | 1.06 | 1.11 | 1.00 | Normal |
| 7 | 0.97 | 1.02 | 1.00 | 1.02 | 0.88 | 1.00 | 1.06 | 1.05 | 1.00 | Normal |
| 8 | 0.98 | 1.01 | 1.00 | 1.03 | 0.96 | 1.00 | 0.98 | 1.00 | 1.00 | Normal |
| 9 | 0.96 | 0.96 | 1.00 | 1.02 | 0.97 | 1.00 | 0.98 | 1.00 | 1.00 | Normal |
| 10 | 0.90 | 0.96 | 1.00 | 1.00 | 0.93 | 1.00 | 1.08 | 1.13 | 1.00 | Normal |
| 11 | 1.02 | 1.03 | 1.00 | 0.93 | 0.93 | 1.00 | 0.95 | 0.94 | 1.00 | Normal |
| 12 | 0.93 | 0.94 | 1.00 | 1.04 | 0.96 | 1.00 | 0.97 | 0.93 | 1.00 | Normal |
| 13 | 0.93 | 1.04 | 1.00 | 1.09 | 1.00 | 1.00 | 0.91 | 0.95 | 1.00 | Normal |
| 14 | 0.98 | 1.06 | 1.00 | 1.03 | 1.00 | 1.00 | 0.98 | 0.96 | 1.00 | Normal |
| 15 | 1.01 | 1.02 | 1.00 | 1.03 | 1.02 | 1.00 | 1.09 | 1.02 | 1.00 | Normal |
| 16 | 0.95 | 1.00 | 1.00 | 1.02 | 1.01 | 1.00 | 0.96 | 1.00 | 1.00 | Normal |
| 17 | 1.09 | 1.05 | 1.00 | 0.98 | 0.87 | 1.00 | 1.03 | 0.98 | 1.00 | Normal |
| 18 | 0.99 | 0.93 | 1.00 | 1.01 | 0.95 | 1.00 | 0.96 | 0.99 | 1.00 | Normal |
| 19 | 1.05 | 1.06 | 1.00 | 1.05 | 1.01 | 1.00 | 1.03 | 1.06 | 1.00 | Normal |
| 20 | 1.06 | 1.09 | 1.00 | 1.05 | 1.02 | 1.00 | 1.03 | 0.96 | 1.00 | Normal |
| 21 | 0.94 | 0.98 | 1.00 | 0.88 | 1.03 | 1.00 | 1.13 | 1.06 | 1.00 | Normal |
| 22 | 0.90 | 0.91 | 1.00 | 0.98 | 1.01 | 1.00 | 0.98 | 1.03 | 1.00 | Normal |
| 23 | 1.06 | 1.06 | 1.00 | 1.03 | 1.03 | 1.00 | 1.06 | 1.03 | 1.00 | Normal |
| 24 | 1.11 | 1.05 | 1.00 | 1.01 | 1.08 | 1.00 | 1.01 | 1.01 | 1.00 | Normal |
| 25 | 0.97 | 0.94 | 1.00 | 0.96 | 1.01 | 1.00 | 0.98 | 0.98 | 1.00 | Normal |
| 26 | 1.02 | 1.00 | 1.00 | 0.89 | 0.93 | 1.00 | 1.24 | 0.95 | 1.00 | aneuploid (+C1) |
| 27 | 0.95 | 0.95 | 1.00 | 1.00 | 0.83 | 1.00 | 1.01 | 0.98 | 1.00 | Normal |
| 28 | 0.97 | 1.00 | 1.00 | 1.09 | 0.97 | 1.00 | 1.03 | 1.02 | 1.00 | Normal |
| 29 | 0.96 | 0.96 | 1.00 | 1.00 | 0.97 | 1.00 | 1.06 | 0.97 | 1.00 | Normal |
| 30 | 0.96 | 1.00 | 1.00 | 1.07 | 0.99 | 1.00 | 1.01 | 0.94 | 1.00 | Normal |
| 31 | 1.12 | 1.08 | 1.00 | 0.96 | 0.93 | 1.00 | 1.04 | 1.00 | 1.00 | Normal |
| 32 | 0.96 | 0.99 | 1.00 | 0.98 | 0.93 | 1.00 | 1.04 | 0.94 | 1.00 | Normal |
| 33 | 1.01 | 1.00 | 1.00 | 1.02 | 0.96 | 1.00 | 0.96 | 0.98 | 1.00 | Normal |
| 34 | 0.94 | 1.06 | 1.00 | 0.99 | 0.86 | 1.00 | 1.12 | 0.98 | 1.00 | Normal |
| 35 | 1.01 | 1.04 | 1.00 | 0.98 | 0.99 | 1.00 | 1.03 | 0.95 | 1.00 | Normal |
| 36 | 0.93 | 0.95 | 1.00 | 1.00 | 0.99 | 1.00 | 1.01 | 1.05 | 1.00 | Normal |
| 37 | 0.99 | 0.98 | 1.00 | 1.04 | 1.01 | 1.00 | 1.01 | 0.99 | 1.00 | Normal |
| 38 | 0.96 | 0.98 | 1.00 | 1.00 | 1.00 | 1.00 | 1.10 | 0.94 | 1.00 | Normal |
| 39 | 0.97 | 1.01 | 1.00 | 1.04 | 1.09 | 1.00 | 0.88 | 0.95 | 1.00 | Normal |
| 40 | 1.03 | 1.05 | 1.00 | 0.98 | 0.95 | 1.00 | 0.92 | 0.98 | 1.00 | Normal |
| 41 | 1.05 | 0.98 | 1.00 | 0.96 | 0.94 | 1.00 | 1.03 | 0.98 | 1.00 | Normal |
| 42 | 1.03 | 1.06 | 1.00 | 0.96 | 1.01 | 1.00 | 0.92 | 0.98 | 1.00 | Normal |
| 43 | 1.03 | 0.99 | 1.00 | 1.04 | 0.95 | 1.00 | 0.98 | 0.92 | 1.00 | Normal |
| 44 | 1.06 | 0.95 | 1.00 | 1.00 | 0.97 | 1.00 | 0.97 | 0.93 | 1.00 | Normal |
| 45 | 1.02 | 0.98 | 1.00 | 1.00 | 0.99 | 1.00 | 1.03 | 1.04 | 1.00 | Normal |
| 46 | 0.93 | 0.94 | 1.00 | 1.00 | 0.96 | 1.00 | 0.89 | 1.03 | 1.00 | Normal |
| 47 | 1.01 | 1.05 | 1.00 | 0.98 | 0.89 | 1.00 | 0.92 | 0.96 | 1.00 | Normal |
| 48 | 0.92 | 0.90 | 1.00 | 0.94 | 0.91 | 1.00 | 1.01 | 1.03 | 1.00 | Normal |
| 49 | 0.98 | 0.91 | 1.00 | 0.98 | 0.99 | 1.00 | 1.13 | 1.03 | 1.00 | Normal |
| 50 | 0.93 | 0.96 | 1.00 | 0.96 | 0.99 | 1.00 | 1.01 | 1.02 | 1.00 | Normal |
| 51 | 1.00 | 1.00 | 1.00 | 0.95 | 0.99 | 1.00 | 0.95 | 0.96 | 1.00 | Normal |
| 52 | 1.02 | 1.08 | 1.00 | 0.96 | 0.93 | 1.00 | 0.96 | 0.99 | 1.00 | Normal |

TABLE 5-continued

Result of testing aneuploid in the F1 variety of cauliflower (raw data obtained by multiplex PCR based on the fluorescent probe method (value calculated by the ΔΔCt method))

| | C6C4C2 triplex PCR | | | C9C3C8 triplex PCR | | | C1C5C7 triplex PCR | | | |
|---|---|---|---|---|---|---|---|---|---|---|
| individual No. | C6 C6/C2 ΔΔCt | C4 C4/C2 ΔΔCt | C2 C2/C2 ΔΔCt | C9 C9/C8 ΔΔCt | C3 C3/C8 ΔΔCt | C8 C8/C8 ΔΔCt | C1 C1/C7 ΔΔCt | C5 C5/C7 ΔΔCt | C7 C7/C7 ΔΔCt | results |
| 53 | 1.01 | 1.04 | 1.00 | 0.94 | 1.04 | 1.00 | 1.01 | 1.06 | 1.00 | Normal |
| 54 | 1.01 | 1.03 | 1.00 | 1.02 | 1.07 | 1.00 | 0.96 | 0.99 | 1.00 | Normal |
| 55 | 1.12 | 1.11 | 1.00 | 0.98 | 1.00 | 1.00 | 1.02 | 1.05 | 1.00 | Normal |
| 56 | 1.03 | 0.98 | 1.00 | 0.99 | 0.97 | 1.00 | 0.93 | 0.94 | 1.00 | Normal |
| 57 | 0.71 | 0.71 | 1.00 | 1.05 | 1.09 | 1.00 | 0.97 | 1.01 | 1.00 | aneuploid (+C2) |
| 58 | 0.97 | 1.00 | 1.00 | 0.98 | 1.01 | 1.00 | 0.94 | 0.94 | 1.00 | Normal |
| 59 | 0.98 | 0.97 | 1.00 | 1.02 | 1.11 | 1.00 | 1.02 | 1.04 | 1.00 | Normal |
| 60 | 1.03 | 1.01 | 1.00 | 1.04 | 1.00 | 1.00 | 1.01 | 1.05 | 1.00 | Normal |
| 61 | 0.99 | 1.02 | 1.00 | 0.95 | 0.97 | 1.00 | 1.08 | 1.12 | 1.00 | Normal |
| 62 | 0.94 | 0.97 | 1.00 | 1.05 | 1.09 | 1.00 | 1.01 | 1.02 | 1.00 | Normal |
| 63 | 0.95 | 1.02 | 1.00 | 0.94 | 0.99 | 1.00 | 1.07 | 1.05 | 1.00 | Normal |
| 64 | 0.96 | 1.00 | 1.00 | 0.98 | 1.01 | 1.00 | 1.01 | 1.02 | 1.00 | Normal |
| 65 | 1.00 | 1.01 | 1.00 | 1.02 | 1.00 | 1.00 | 0.96 | 0.94 | 1.00 | Normal |
| 66 | 1.03 | 0.96 | 1.00 | 1.00 | 1.03 | 1.00 | 0.98 | 0.95 | 1.00 | Normal |
| 67 | 0.99 | 1.02 | 1.00 | 1.04 | 1.07 | 1.00 | 1.00 | 0.93 | 1.00 | Normal |
| 68 | 1.10 | 1.05 | 1.00 | 0.97 | 0.99 | 1.00 | 1.03 | 0.92 | 1.00 | Normal |
| 69 | 1.09 | 1.08 | 1.00 | 1.10 | 1.11 | 1.00 | 0.98 | 1.00 | 1.00 | Normal |
| 70 | 0.98 | 1.02 | 1.00 | 1.13 | 1.12 | 1.00 | 0.98 | 1.01 | 1.00 | Normal |
| 71 | 1.01 | 0.99 | 1.00 | 0.99 | 1.12 | 1.00 | 1.04 | 1.06 | 1.00 | Normal |
| 72 | 0.93 | 0.98 | 1.00 | 1.02 | 1.09 | 1.00 | 0.96 | 0.92 | 1.00 | Normal |
| 73 | 1.03 | 1.00 | 1.00 | 1.05 | 1.09 | 1.00 | 1.03 | 1.07 | 1.00 | Normal |
| 74 | 1.05 | 1.09 | 1.00 | 0.94 | 1.01 | 1.00 | 1.01 | 1.02 | 1.00 | Normal |
| 75 | 0.89 | 0.98 | 1.00 | 1.07 | 1.04 | 1.00 | 0.93 | 0.94 | 1.00 | Normal |
| 76 | 0.91 | 0.98 | 1.00 | 1.02 | 0.99 | 1.00 | 0.90 | 0.98 | 1.00 | Normal |
| 77 | 1.01 | 0.94 | 1.00 | 1.05 | 1.09 | 1.00 | 1.01 | 0.98 | 1.00 | Normal |
| 78 | 1.01 | 1.06 | 1.00 | 0.93 | 0.99 | 1.00 | 0.96 | 1.01 | 1.00 | Normal |
| 79 | 0.94 | 0.96 | 1.00 | 1.06 | 1.07 | 1.00 | 0.89 | 0.99 | 1.00 | Normal |
| 80 | 1.07 | 1.05 | 1.00 | 0.99 | 1.06 | 1.00 | 0.97 | 0.98 | 1.00 | Normal |
| 81 | 0.73 | 0.76 | 1.00 | 1.02 | 1.00 | 1.00 | 1.03 | 1.03 | 1.00 | aneuploid (+C2) |
| 82 | 1.03 | 1.02 | 1.00 | 0.96 | 1.01 | 1.00 | 0.99 | 0.99 | 1.00 | Normal |
| 83 | 1.12 | 1.07 | 1.00 | 0.97 | 1.12 | 1.00 | 1.04 | 1.07 | 1.00 | Normal |
| 84 | 0.97 | 0.94 | 1.00 | 1.03 | 0.97 | 1.00 | 1.02 | 1.06 | 1.00 | Normal |
| 85 | 0.88 | 0.90 | 1.00 | 1.04 | 1.04 | 1.00 | 1.06 | 1.03 | 1.00 | Normal |
| 86 | 1.06 | 1.06 | 1.00 | 0.97 | 0.91 | 1.00 | 1.04 | 1.10 | 1.00 | Normal |
| 87 | 0.94 | 0.96 | 1.00 | 1.00 | 1.00 | 1.00 | 0.97 | 1.01 | 1.00 | Normal |
| 88 | 1.37 | 1.04 | 1.00 | 0.93 | 0.89 | 1.00 | 0.89 | 0.98 | 1.00 | aneuploid (+C6) |
| 89 | 1.04 | 1.00 | 1.00 | 1.03 | 1.01 | 1.00 | 0.97 | 0.95 | 1.00 | Normal |
| 90 | 1.06 | 1.02 | 1.00 | 0.98 | 0.95 | 1.00 | 0.91 | 0.99 | 1.00 | Normal |
| 91 | 1.11 | 1.05 | 1.00 | 0.94 | 0.95 | 1.00 | 1.02 | 1.06 | 1.00 | Normal |
| 92 | 0.94 | 0.95 | 1.00 | 1.06 | 0.99 | 1.00 | 0.97 | 0.90 | 1.00 | Normal |
| 93 | 0.91 | 0.98 | 1.00 | 1.04 | 0.93 | 1.00 | 1.05 | 0.96 | 1.00 | Normal |
| 94 | 1.05 | 1.12 | 1.00 | 1.04 | 1.02 | 1.00 | 1.01 | 1.02 | 1.00 | Normal |
| 95 | 0.92 | 0.94 | 1.00 | 1.00 | 1.03 | 1.00 | 0.93 | 1.01 | 1.00 | Normal |
| 96 | 1.00 | 1.04 | 1.00 | 0.96 | 1.03 | 1.00 | 0.91 | 0.99 | 1.00 | Normal |
| 97 | 0.98 | 1.02 | 1.00 | 1.00 | 1.01 | 1.00 | 0.93 | 0.99 | 1.00 | Normal |
| 98 | 1.01 | 1.00 | 1.00 | 1.09 | 0.93 | 1.00 | 0.93 | 0.90 | 1.00 | Normal |
| 99 | 1.09 | 1.10 | 1.00 | 1.12 | 1.09 | 1.00 | 1.01 | 0.96 | 1.00 | Normal |
| 100 | 1.01 | 1.00 | 1.00 | 0.97 | 0.95 | 1.00 | 0.98 | 0.97 | 1.00 | Normal |
| 101 | 1.06 | 1.05 | 1.00 | 1.01 | 0.99 | 1.00 | 1.01 | 1.02 | 1.00 | Normal |
| 102 | 0.98 | 0.96 | 1.00 | 1.05 | 1.00 | 1.00 | 0.88 | 0.96 | 1.00 | Normal |
| 103 | 0.97 | 0.99 | 1.00 | 0.97 | 0.97 | 1.00 | 1.05 | 1.11 | 1.00 | Normal |
| 104 | 0.98 | 1.00 | 1.00 | 1.01 | 1.06 | 1.00 | 1.09 | 1.02 | 1.00 | Normal |
| 105 | 0.94 | 1.01 | 1.00 | 0.96 | 1.03 | 1.00 | 0.93 | 0.98 | 1.00 | Normal |
| 106 | 1.02 | 1.05 | 1.00 | 1.01 | 1.09 | 1.00 | 1.03 | 1.04 | 1.00 | Normal |
| 107 | 0.95 | 0.94 | 1.00 | 1.28 | 1.10 | 1.00 | 1.03 | 1.08 | 1.00 | aneuploid (+C9) |
| 108 | 0.98 | 1.00 | 1.00 | 1.00 | 0.96 | 1.00 | 0.98 | 1.10 | 1.00 | Normal |
| 109 | 0.94 | 1.03 | 1.00 | 1.01 | 1.07 | 1.00 | 1.00 | 1.08 | 1.00 | Normal |
| 110 | 1.00 | 0.98 | 1.00 | 0.90 | 1.03 | 1.00 | 0.96 | 0.96 | 1.00 | Normal |
| 111 | 0.88 | 0.91 | 1.00 | 0.96 | 1.01 | 1.00 | 0.89 | 0.93 | 1.00 | Normal |
| 112 | 1.05 | 1.02 | 1.00 | 0.99 | 0.97 | 1.00 | 0.97 | 1.01 | 1.00 | Normal |
| 113 | 0.89 | 0.90 | 1.00 | 1.07 | 1.01 | 1.00 | 0.94 | 1.02 | 1.00 | Normal |
| 114 | 0.95 | 0.94 | 1.00 | 0.97 | 1.06 | 1.00 | 1.07 | 1.02 | 1.00 | Normal |
| 115 | 1.03 | 1.04 | 1.00 | 0.92 | 0.93 | 1.00 | 1.05 | 0.97 | 1.00 | Normal |
| 116 | 0.96 | 1.00 | 1.00 | 0.95 | 1.02 | 1.00 | 0.98 | 0.99 | 1.00 | Normal |
| 117 | 1.12 | 1.10 | 1.00 | 0.90 | 1.01 | 1.00 | 0.97 | 1.05 | 1.00 | Normal |
| 118 | 0.96 | 1.02 | 1.00 | 1.04 | 1.01 | 1.00 | 0.92 | 1.02 | 1.00 | Normal |
| 119 | 0.88 | 0.89 | 1.00 | 1.07 | 1.05 | 1.00 | 1.03 | 1.00 | 1.00 | Normal |
| 120 | 0.95 | 0.94 | 1.00 | 0.95 | 0.95 | 1.00 | 1.00 | 1.06 | 1.00 | Normal |
| 121 | 0.91 | 1.05 | 1.00 | 0.97 | 1.07 | 1.00 | 1.03 | 1.04 | 1.00 | Normal |
| 122 | 1.11 | 1.02 | 1.00 | 1.03 | 0.96 | 1.00 | 0.92 | 0.96 | 1.00 | Normal |
| 123 | 1.03 | 0.98 | 1.00 | 1.00 | 1.11 | 1.00 | 0.98 | 1.07 | 1.00 | Normal |

TABLE 5-continued

Result of testing aneuploid in the F1 variety of cauliflower (raw data obtained by multiplex PCR based on the fluorescent probe method (value calculated by the ΔΔCt method))

| | C6C4C2 triplex PCR | | | C9C3C8 triplex PCR | | | C1C5C7 triplex PCR | | | |
|---|---|---|---|---|---|---|---|---|---|---|
| individual No. | C6 C6/C2 ΔΔCt | C4 C4/C2 ΔΔCt | C2 C2/C2 ΔΔCt | C9 C9/C8 ΔΔCt | C3 C3/C8 ΔΔCt | C8 C8/C8 ΔΔCt | C1 C1/C7 ΔΔCt | C5 C5/C7 ΔΔCt | C7 C7/C7 ΔΔCt | results |
| 124 | 1.02 | 0.98 | 1.00 | 1.11 | 1.09 | 1.00 | 1.00 | 1.05 | 1.00 | Normal |
| 125 | 1.12 | 1.06 | 1.00 | 1.05 | 1.01 | 1.00 | 0.96 | 0.94 | 1.00 | Normal |
| 126 | 1.09 | 1.11 | 1.00 | 0.94 | 0.95 | 1.00 | 1.13 | 1.03 | 1.00 | Normal |
| 127 | 0.93 | 1.00 | 1.00 | 1.01 | 0.95 | 1.00 | 1.09 | 1.12 | 1.00 | Normal |
| 128 | 1.32 | 1.00 | 1.00 | 0.98 | 1.01 | 1.00 | 1.03 | 0.91 | 1.00 | aneuploid (+C6) |
| 129 | 1.01 | 0.99 | 1.00 | 0.98 | 0.98 | 1.00 | 0.99 | 1.05 | 1.00 | Normal |
| 130 | 1.01 | 1.00 | 1.00 | 0.95 | 1.05 | 1.00 | 1.01 | 1.06 | 1.00 | Normal |
| 131 | 1.01 | 1.02 | 1.00 | 1.00 | 0.88 | 1.00 | 0.96 | 0.94 | 1.00 | Normal |
| 132 | 1.04 | 1.02 | 1.00 | 0.92 | 1.00 | 1.00 | 1.09 | 1.12 | 1.00 | Normal |
| 133 | 1.12 | 1.07 | 1.00 | 1.02 | 1.04 | 1.00 | 1.05 | 0.99 | 1.00 | Normal |
| 134 | 1.04 | 1.07 | 1.00 | 1.03 | 0.99 | 1.00 | 0.98 | 1.03 | 1.00 | Normal |
| 135 | 1.08 | 1.03 | 1.00 | 0.91 | 0.94 | 1.00 | 1.08 | 0.98 | 1.00 | Normal |
| 136 | 1.04 | 1.02 | 1.00 | 0.98 | 0.95 | 1.00 | 0.98 | 0.97 | 1.00 | Normal |
| 137 | 0.94 | 0.86 | 1.00 | 1.03 | 1.08 | 1.00 | 1.02 | 0.96 | 1.00 | Normal |
| 138 | 1.00 | 1.05 | 1.00 | 0.99 | 1.01 | 1.00 | 0.95 | 1.03 | 1.00 | Normal |
| 139 | 1.04 | 1.04 | 1.00 | 1.01 | 1.06 | 1.00 | 1.10 | 1.11 | 1.00 | Normal |
| 140 | 0.92 | 0.95 | 1.00 | 1.01 | 0.99 | 1.00 | 1.01 | 1.03 | 1.00 | Normal |
| 141 | 0.94 | 0.93 | 1.00 | 1.00 | 1.04 | 1.00 | 0.99 | 0.96 | 1.00 | Normal |
| 142 | 1.04 | 1.06 | 1.00 | 1.00 | 1.00 | 1.00 | 0.99 | 1.03 | 1.00 | Normal |
| 143 | 0.99 | 0.96 | 1.00 | 1.14 | 1.04 | 1.00 | 0.99 | 1.08 | 1.00 | Normal |
| 144 | 0.98 | 1.00 | 1.00 | 0.99 | 0.95 | 1.00 | 0.97 | 1.02 | 1.00 | Normal |
| 145 | 1.06 | 1.08 | 1.00 | 1.10 | 1.01 | 1.00 | 0.95 | 1.03 | 1.00 | Normal |
| 146 | 0.92 | 0.99 | 1.00 | 0.98 | 0.99 | 1.00 | 1.05 | 1.00 | 1.00 | Normal |
| 147 | 0.98 | 0.98 | 1.00 | 1.00 | 1.04 | 1.00 | 0.95 | 0.96 | 1.00 | Normal |
| 148 | 0.94 | 0.98 | 1.00 | 1.02 | 1.01 | 1.00 | 1.06 | 1.06 | 1.00 | Normal |
| 149 | 0.99 | 0.92 | 1.00 | 0.96 | 1.10 | 1.00 | 1.02 | 1.05 | 1.00 | Normal |
| 150 | 1.06 | 1.07 | 1.00 | 0.99 | 1.01 | 1.00 | 1.01 | 0.93 | 1.00 | Normal |
| 151 | 1.03 | 0.98 | 1.00 | 1.10 | 1.09 | 1.00 | 1.03 | 1.02 | 1.00 | Normal |
| 152 | 0.96 | 1.01 | 1.00 | 1.09 | 1.03 | 1.00 | 1.09 | 1.06 | 1.00 | Normal |
| 153 | 1.06 | 1.08 | 1.00 | 1.02 | 0.95 | 1.00 | 1.01 | 1.02 | 1.00 | Normal |
| 154 | 0.98 | 1.05 | 1.00 | 1.10 | 1.09 | 1.00 | 0.96 | 0.96 | 1.00 | Normal |
| 155 | 0.99 | 0.98 | 1.00 | 0.95 | 0.94 | 1.00 | 1.02 | 0.96 | 1.00 | Normal |
| 156 | 1.04 | 0.98 | 1.00 | 1.03 | 1.10 | 1.00 | 0.97 | 0.99 | 1.00 | Normal |
| 157 | 1.00 | 1.03 | 1.00 | 0.90 | 0.95 | 1.00 | 1.01 | 0.94 | 1.00 | Normal |
| 158 | 1.06 | 1.02 | 1.00 | 0.99 | 1.03 | 1.00 | 0.99 | 1.09 | 1.00 | Normal |
| 159 | 0.93 | 0.96 | 1.00 | 0.94 | 0.98 | 1.00 | 0.93 | 0.94 | 1.00 | Normal |
| 150 | 0.98 | 0.95 | 1.00 | 1.03 | 1.01 | 1.00 | 1.01 | 0.96 | 1.00 | Normal |
| 161 | 0.97 | 0.98 | 1.00 | 0.98 | 1.03 | 1.00 | 0.91 | 0.95 | 1.00 | Normal |
| 162 | 1.02 | 0.98 | 1.00 | 1.05 | 1.12 | 1.00 | 1.00 | 1.05 | 1.00 | Normal |
| 163 | 1.01 | 1.05 | 1.00 | 0.90 | 0.95 | 1.00 | 1.06 | 1.05 | 1.00 | Normal |
| 164 | 0.91 | 0.92 | 1.00 | 0.98 | 0.98 | 1.00 | 0.96 | 0.96 | 1.00 | Normal |
| 165 | 1.03 | 1.05 | 1.00 | 1.03 | 1.13 | 1.00 | 0.96 | 0.92 | 1.00 | Normal |
| 166 | 0.88 | 0.94 | 1.00 | 1.00 | 0.93 | 1.00 | 1.05 | 0.99 | 1.00 | Normal |
| 167 | 0.88 | 1.00 | 1.00 | 0.95 | 0.97 | 1.00 | 1.01 | 0.93 | 1.00 | Normal |
| 168 | 0.97 | 1.00 | 1.00 | 0.99 | 0.97 | 1.00 | 0.97 | 0.92 | 1.00 | Normal |
| 169 | 0.94 | 0.92 | 1.00 | 0.97 | 0.89 | 1.00 | 0.96 | 0.93 | 1.00 | Normal |
| 170 | 1.03 | 1.02 | 1.00 | 1.05 | 1.01 | 1.00 | 1.29 | 0.95 | 1.00 | aneuploid (+C1) |
| 171 | 0.98 | 1.05 | 1.00 | 1.05 | 1.01 | 1.00 | 1.09 | 1.02 | 1.00 | Normal |
| 172 | 0.94 | 0.98 | 1.00 | 0.98 | 0.96 | 1.00 | 0.97 | 1.00 | 1.00 | Normal |
| 173 | 1.06 | 1.24 | 1.00 | 1.00 | 1.02 | 1.00 | 1.09 | 1.02 | 1.00 | aneuploid (+C4) |
| 174 | 1.00 | 1.08 | 1.00 | 0.92 | 0.97 | 1.00 | 1.06 | 1.10 | 1.00 | Normal |
| 175 | 1.08 | 1.08 | 1.00 | 1.01 | 0.99 | 1.00 | 1.04 | 0.95 | 1.00 | Normal |
| 176 | 1.03 | 1.11 | 1.00 | 1.01 | 0.94 | 1.00 | 0.99 | 0.96 | 1.00 | Normal |
| 177 | 0.96 | 1.01 | 1.00 | 0.96 | 0.96 | 1.00 | 0.98 | 1.00 | 1.00 | Normal |
| 178 | 1.01 | 1.05 | 1.00 | 0.97 | 0.95 | 1.00 | 1.06 | 1.00 | 1.00 | Normal |
| 179 | 0.87 | 0.96 | 1.00 | 1.00 | 0.99 | 1.00 | 1.01 | 1.02 | 1.00 | Normal |
| 180 | 1.08 | 1.05 | 1.00 | 1.02 | 0.97 | 1.00 | 0.98 | 1.00 | 1.00 | Normal |
| 181 | 0.96 | 1.04 | 1.00 | 0.92 | 1.02 | 1.00 | 0.94 | 0.93 | 1.00 | Normal |
| 182 | 1.04 | 1.08 | 1.00 | 1.10 | 1.12 | 1.00 | 0.88 | 0.96 | 1.00 | Normal |
| 183 | 1.04 | 1.04 | 1.00 | 0.99 | 1.07 | 1.00 | 1.11 | 0.98 | 1.00 | Normal |
| 184 | 1.03 | 1.03 | 1.00 | 1.07 | 1.08 | 1.00 | 1.01 | 0.99 | 1.00 | Normal |
| 185 | 0.94 | 0.94 | 1.00 | 0.94 | 0.97 | 1.00 | 1.02 | 1.00 | 1.00 | Normal |
| 186 | 1.01 | 1.00 | 1.00 | 0.99 | 0.97 | 1.00 | 1.08 | 1.02 | 1.00 | Normal |
| 187 | 1.01 | 0.98 | 1.00 | 1.00 | 0.94 | 1.00 | 1.01 | 1.05 | 1.00 | Normal |
| 188 | 1.12 | 1.06 | 1.00 | 1.13 | 1.10 | 1.00 | 0.99 | 1.03 | 1.00 | Normal |
| 189 | 1.04 | 1.03 | 1.00 | 1.00 | 0.99 | 1.00 | 1.06 | 1.02 | 1.00 | Normal |
| 190 | 1.04 | 1.00 | 1.00 | 0.96 | 0.90 | 1.00 | 0.99 | 0.97 | 1.00 | Normal |
| 191 | 1.09 | 1.11 | 1.00 | 1.01 | 0.96 | 1.00 | 1.08 | 1.01 | 1.00 | Normal |
| 192 | 1.10 | 1.09 | 1.00 | 1.02 | 0.99 | 1.00 | 1.00 | 1.00 | 1.00 | Normal |
| 193 | 1.06 | 1.00 | 1.00 | 0.96 | 0.98 | 1.00 | 0.96 | 1.00 | 1.00 | Normal |
| 194 | 0.99 | 0.99 | 1.00 | 1.05 | 0.90 | 1.00 | 1.07 | 1.11 | 1.00 | Normal |

TABLE 5-continued

Result of testing aneuploid in the F1 variety of cauliflower (raw data obtained by multiplex PCR based on the fluorescent probe method (value calculated by the ΔΔCt method))

| | C6C4C2 triplex PCR | | | C9C3C8 triplex PCR | | | C1C5C7 triplex PCR | | | |
|---|---|---|---|---|---|---|---|---|---|---|
| individual No. | C6 C6/C2 ΔΔCt | C4 C4/C2 ΔΔCt | C2 C2/C2 ΔΔCt | C9 C9/C8 ΔΔCt | C3 C3/C8 ΔΔCt | C8 C8/C8 ΔΔCt | C1 C1/C7 ΔΔCt | C5 C5/C7 ΔΔCt | C7 C7/C7 ΔΔCt | results |
| 195 | 0.96 | 1.07 | 1.00 | 0.99 | 0.94 | 1.00 | 1.02 | 1.03 | 1.00 | Normal |
| 196 | 1.09 | 1.06 | 1.00 | 1.00 | 0.95 | 1.00 | 0.99 | 1.02 | 1.00 | Normal |
| 197 | 0.92 | 0.94 | 1.00 | 0.99 | 0.96 | 1.00 | 0.91 | 0.94 | 1.00 | Normal |
| 198 | 1.05 | 1.04 | 1.00 | 1.03 | 1.01 | 1.00 | 0.96 | 0.98 | 1.00 | Normal |
| 199 | 0.93 | 0.98 | 1.00 | 0.94 | 0.94 | 1.00 | 1.02 | 0.98 | 1.00 | Normal |
| 200 | 1.07 | 1.01 | 1.00 | 0.95 | 0.99 | 1.00 | 1.00 | 1.03 | 1.00 | Normal |
| 201 | 1.03 | 1.03 | 1.00 | 1.05 | 1.01 | 1.00 | 1.01 | 1.04 | 1.00 | Normal |
| 202 | 1.01 | 1.06 | 1.00 | 1.05 | 0.95 | 1.00 | 1.02 | 1.11 | 1.00 | Normal |
| 203 | 1.06 | 1.10 | 1.00 | 1.01 | 0.95 | 1.00 | 0.97 | 1.01 | 1.00 | Normal |
| 204 | 1.06 | 1.04 | 1.00 | 1.05 | 1.01 | 1.00 | 1.03 | 1.00 | 1.00 | Normal |
| 205 | 0.95 | 0.98 | 1.00 | 0.98 | 0.94 | 1.00 | 0.97 | 0.95 | 1.00 | Normal |
| 206 | 1.06 | 1.06 | 1.00 | 1.01 | 0.97 | 1.00 | 1.03 | 1.02 | 1.00 | Normal |
| 207 | 1.00 | 1.00 | 1.00 | 1.13 | 1.05 | 1.00 | 0.98 | 1.00 | 1.00 | Normal |
| 208 | 0.91 | 0.94 | 1.00 | 1.00 | 1.01 | 1.00 | 1.02 | 0.98 | 1.00 | Normal |
| 209 | 1.01 | 0.99 | 1.00 | 0.98 | 0.95 | 1.00 | 1.03 | 1.02 | 1.00 | Normal |
| 210 | 1.06 | 1.00 | 1.00 | 0.99 | 1.07 | 1.00 | 0.93 | 0.91 | 1.00 | Normal |
| 211 | 0.94 | 0.90 | 1.00 | 0.93 | 0.97 | 1.00 | 1.05 | 1.00 | 1.00 | Normal |
| 212 | 1.06 | 1.05 | 1.00 | 1.00 | 0.98 | 1.00 | 1.04 | 1.08 | 1.00 | Normal |
| 213 | 1.04 | 1.03 | 1.00 | 1.02 | 0.98 | 1.00 | 0.97 | 0.96 | 1.00 | Normal |
| 214 | 0.94 | 0.96 | 1.00 | 0.95 | 0.98 | 1.00 | 0.96 | 0.94 | 1.00 | Normal |
| 215 | 1.01 | 1.02 | 1.00 | 0.96 | 0.98 | 1.00 | 1.02 | 0.98 | 1.00 | Normal |
| 216 | 1.09 | 1.04 | 1.00 | 1.00 | 0.99 | 1.00 | 1.05 | 1.01 | 1.00 | Normal |
| 217 | 1.03 | 0.91 | 1.00 | 1.00 | 1.12 | 1.00 | 1.05 | 1.02 | 1.00 | Normal |
| 218 | 1.06 | 1.06 | 1.00 | 0.92 | 0.98 | 1.00 | 1.06 | 1.05 | 1.00 | Normal |
| 219 | 0.99 | 1.00 | 1.00 | 0.96 | 0.99 | 1.00 | 0.96 | 1.01 | 1.00 | Normal |
| 220 | 0.92 | 0.93 | 1.00 | 0.98 | 0.99 | 1.00 | 1.03 | 0.99 | 1.00 | Normal |
| 221 | 1.06 | 1.11 | 1.00 | 1.05 | 1.12 | 1.00 | 1.00 | 1.07 | 1.00 | Normal |
| 222 | 1.10 | 1.10 | 1.00 | 1.00 | 1.01 | 1.00 | 0.96 | 0.98 | 1.00 | Normal |
| 223 | 0.99 | 1.02 | 1.00 | 1.03 | 1.00 | 1.00 | 0.93 | 1.01 | 1.00 | Normal |
| 224 | 0.96 | 1.01 | 1.00 | 1.01 | 1.00 | 1.00 | 0.99 | 1.08 | 1.00 | Normal |
| 225 | 1.01 | 1.01 | 1.00 | 1.08 | 1.03 | 1.00 | 0.96 | 0.98 | 1.00 | Normal |
| 226 | 0.96 | 1.02 | 1.00 | 0.97 | 0.99 | 1.00 | 1.12 | 1.08 | 1.00 | Normal |
| 227 | 1.12 | 0.98 | 1.00 | 1.02 | 0.98 | 1.00 | 0.95 | 1.00 | 1.00 | Normal |
| 228 | 1.41 | 1.08 | 1.00 | 0.94 | 0.93 | 1.00 | 0.91 | 0.92 | 1.00 | aneuploid (+C6) |
| 229 | 1.00 | 0.99 | 1.00 | 0.90 | 0.98 | 1.00 | 1.01 | 1.01 | 1.00 | Normal |
| 230 | 0.93 | 0.89 | 1.00 | 0.98 | 1.01 | 1.00 | 1.05 | 1.02 | 1.00 | Normal |
| 231 | 1.08 | 1.10 | 1.00 | 1.00 | 0.97 | 1.00 | 1.06 | 1.11 | 1.00 | Normal |
| 232 | 1.01 | 1.07 | 1.00 | 1.03 | 1.06 | 1.00 | 0.96 | 0.99 | 1.00 | Normal |
| 233 | 1.03 | 1.08 | 1.00 | 0.94 | 1.06 | 1.00 | 0.93 | 1.00 | 1.00 | Normal |
| 234 | 0.97 | 1.05 | 1.00 | 0.96 | 1.02 | 1.00 | 0.97 | 0.93 | 1.00 | Normal |
| 235 | 1.07 | 0.98 | 1.00 | 0.90 | 0.89 | 1.00 | 1.12 | 1.08 | 1.00 | Normal |
| 236 | 1.03 | 1.02 | 1.00 | 1.02 | 0.94 | 1.00 | 0.95 | 0.98 | 1.00 | Normal |
| 237 | 1.03 | 1.08 | 1.00 | 1.05 | 1.09 | 1.00 | 0.95 | 1.05 | 1.00 | Normal |
| 238 | 1.08 | 1.07 | 1.00 | 1.01 | 1.06 | 1.00 | 0.98 | 0.98 | 1.00 | Normal |
| 239 | 0.96 | 1.02 | 1.00 | 1.02 | 1.09 | 1.00 | 1.01 | 0.98 | 1.00 | Normal |
| 240 | 1.00 | 1.05 | 1.00 | 1.02 | 1.00 | 1.00 | 1.06 | 0.92 | 1.00 | Normal |
| 241 | 0.92 | 0.96 | 1.00 | 1.00 | 1.09 | 1.00 | 0.96 | 0.99 | 1.00 | Normal |
| 242 | 0.94 | 0.99 | 1.00 | 0.98 | 1.01 | 1.00 | 1.09 | 0.98 | 1.00 | Normal |
| 243 | 0.93 | 0.94 | 1.00 | 1.01 | 0.97 | 1.00 | 1.02 | 0.99 | 1.00 | Normal |
| 244 | 0.96 | 1.00 | 1.00 | 1.02 | 1.01 | 1.00 | 0.94 | 0.98 | 1.00 | Normal |
| 245 | 1.02 | 1.05 | 1.00 | 0.94 | 0.96 | 1.00 | 1.03 | 0.92 | 1.00 | Normal |
| 246 | 0.91 | 1.01 | 1.00 | 1.00 | 1.13 | 1.00 | 0.96 | 0.94 | 1.00 | Normal |
| 247 | 1.10 | 1.08 | 1.00 | 0.98 | 1.01 | 1.00 | 1.02 | 0.97 | 1.00 | Normal |
| 248 | 0.96 | 0.96 | 1.00 | 1.07 | 1.03 | 1.00 | 1.04 | 1.10 | 1.00 | Normal |
| 249 | 0.98 | 1.02 | 1.00 | 0.99 | 0.98 | 1.00 | 1.08 | 0.98 | 1.00 | Normal |
| 250 | 1.03 | 1.00 | 1.00 | 1.07 | 1.00 | 1.00 | 1.09 | 1.11 | 1.00 | Normal |
| 251 | 1.04 | 1.09 | 1.00 | 0.95 | 0.91 | 1.00 | 1.03 | 0.97 | 1.00 | Normal |
| 252 | 0.93 | 0.92 | 1.00 | 1.01 | 0.95 | 1.00 | 0.91 | 0.90 | 1.00 | Normal |
| 253 | 0.95 | 0.94 | 1.00 | 1.02 | 1.02 | 1.00 | 1.03 | 0.99 | 1.00 | Normal |
| 254 | 1.14 | 1.09 | 1.00 | 0.92 | 0.85 | 1.00 | 1.05 | 0.97 | 1.00 | Normal |
| 255 | 0.89 | 0.89 | 1.00 | 1.05 | 1.13 | 1.00 | 1.03 | 1.00 | 1.00 | Normal |
| 256 | 1.03 | 1.08 | 1.00 | 0.98 | 0.97 | 1.00 | 1.00 | 0.99 | 1.00 | Normal |
| 257 | 1.05 | 1.00 | 1.00 | 0.99 | 0.97 | 1.00 | 1.07 | 1.00 | 1.00 | Normal |
| 258 | 0.93 | 1.06 | 1.00 | 1.06 | 1.02 | 1.00 | 0.96 | 0.95 | 1.00 | Normal |
| 259 | 1.04 | 1.08 | 1.00 | 0.98 | 0.96 | 1.00 | 1.06 | 1.05 | 1.00 | Normal |
| 260 | 0.98 | 1.02 | 1.00 | 1.05 | 1.06 | 1.00 | 1.03 | 1.02 | 1.00 | Normal |
| 261 | 1.00 | 1.01 | 1.00 | 1.01 | 1.01 | 1.00 | 1.03 | 1.05 | 1.00 | Normal |
| 262 | 0.89 | 0.96 | 1.00 | 1.02 | 0.97 | 1.00 | 1.01 | 0.96 | 1.00 | Normal |
| 263 | 1.03 | 1.05 | 1.00 | 1.10 | 1.05 | 1.00 | 1.03 | 1.02 | 1.00 | Normal |
| 264 | 0.94 | 1.03 | 1.00 | 1.04 | 0.98 | 1.00 | 1.03 | 1.05 | 1.00 | Normal |
| 265 | 1.02 | 1.02 | 1.00 | 0.96 | 0.90 | 1.00 | 0.94 | 0.94 | 1.00 | Normal |

TABLE 5-continued

Result of testing aneuploid in the F1 variety of cauliflower (raw data obtained by multiplex PCR based on the fluorescent probe method (value calculated by the ΔΔCt method))

| individual No. | C6C4C2 triplex PCR | | | C9C3C8 triplex PCR | | | C1C5C7 triplex PCR | | | results |
|---|---|---|---|---|---|---|---|---|---|---|
| | C6 C6/C2 ΔΔCt | C4 C4/C2 ΔΔCt | C2 C2/C2 ΔΔCt | C9 C9/C8 ΔΔCt | C3 C3/C8 ΔΔCt | C8 C8/C8 ΔΔCt | C1 C1/C7 ΔΔCt | C5 C5/C7 ΔΔCt | C7 C7/C7 ΔΔCt | |
| 266 | 0.91 | 0.92 | 1.00 | 0.96 | 0.97 | 1.00 | 0.98 | 0.92 | 1.00 | Normal |
| 267 | 0.91 | 1.02 | 1.00 | 0.96 | 1.05 | 1.00 | 1.01 | 0.96 | 1.00 | Normal |
| 268 | 0.96 | 0.96 | 1.00 | 1.04 | 1.10 | 1.00 | 0.96 | 1.01 | 1.00 | Normal |
| 269 | 1.01 | 1.04 | 1.00 | 1.03 | 1.04 | 1.00 | 0.98 | 1.00 | 1.00 | Normal |
| 270 | 0.98 | 1.00 | 1.00 | 1.10 | 1.01 | 1.00 | 1.04 | 1.05 | 1.00 | Normal |
| 271 | 0.94 | 0.93 | 1.00 | 1.00 | 1.02 | 1.00 | 0.89 | 0.86 | 1.00 | Normal |
| 272 | 1.02 | 1.08 | 1.00 | 1.01 | 0.91 | 1.00 | 0.93 | 0.96 | 1.00 | Normal |
| 273 | 0.94 | 0.95 | 1.00 | 1.00 | 0.97 | 1.00 | 0.93 | 0.96 | 1.00 | Normal |
| 274 | 1.02 | 1.08 | 1.00 | 1.10 | 1.00 | 1.00 | 1.03 | 0.96 | 1.00 | Normal |
| 275 | 0.98 | 0.97 | 1.00 | 0.92 | 0.95 | 1.00 | 1.01 | 0.98 | 1.00 | Normal |
| 276 | 1.03 | 0.99 | 1.00 | 0.98 | 0.93 | 1.00 | 1.01 | 1.06 | 1.00 | Normal |
| 277 | 0.98 | 1.00 | 1.00 | 0.99 | 0.99 | 1.00 | 1.06 | 1.05 | 1.00 | Normal |
| 278 | 1.12 | 1.01 | 1.00 | 0.95 | 0.97 | 1.00 | 1.00 | 0.95 | 1.00 | Normal |
| 279 | 1.06 | 0.99 | 1.00 | 1.01 | 1.05 | 1.00 | 1.01 | 1.01 | 1.00 | Normal |
| 280 | 1.01 | 1.02 | 1.00 | 0.98 | 0.94 | 1.00 | 0.96 | 0.98 | 1.00 | Normal |
| 281 | 1.03 | 1.00 | 1.00 | 1.00 | 0.93 | 1.00 | 0.96 | 1.01 | 1.00 | Normal |
| 282 | 1.04 | 0.99 | 1.00 | 1.06 | 1.06 | 1.00 | 0.94 | 0.94 | 1.00 | Normal |
| 283 | 0.97 | 0.96 | 1.00 | 0.92 | 0.90 | 1.00 | 1.07 | 1.05 | 1.00 | Normal |
| 284 | 1.12 | 1.04 | 1.00 | 0.99 | 0.98 | 1.00 | 0.91 | 0.95 | 1.00 | Normal |
| 285 | 1.01 | 0.96 | 1.00 | 0.98 | 0.93 | 1.00 | 0.97 | 0.94 | 1.00 | Normal |
| 286 | 1.05 | 1.00 | 1.00 | 0.96 | 1.09 | 1.00 | 0.88 | 0.96 | 1.00 | Normal |
| 287 | 1.06 | 1.03 | 1.00 | 0.89 | 0.90 | 1.00 | 0.98 | 1.00 | 1.00 | Normal |
| 288 | 0.89 | 0.92 | 1.00 | 1.02 | 1.01 | 1.00 | 1.06 | 0.98 | 1.00 | Normal |
| 289 | 0.89 | 0.89 | 1.00 | 0.97 | 0.95 | 1.00 | 0.95 | 0.99 | 1.00 | Normal |
| 290 | 0.94 | 0.89 | 1.00 | 1.04 | 0.97 | 1.00 | 1.02 | 0.94 | 1.00 | Normal |
| 291 | 1.03 | 1.03 | 1.00 | 1.01 | 1.01 | 1.00 | 0.98 | 0.98 | 1.00 | Normal |
| 292 | 0.96 | 0.99 | 1.00 | 1.01 | 1.06 | 1.00 | 0.88 | 0.98 | 1.00 | Normal |
| 293 | 0.91 | 0.94 | 1.00 | 0.97 | 0.99 | 1.00 | 0.98 | 1.05 | 1.00 | Normal |
| 294 | 1.06 | 1.06 | 1.00 | 1.07 | 1.03 | 1.00 | 0.95 | 0.94 | 1.00 | Normal |
| 295 | 0.94 | 0.87 | 1.00 | 0.95 | 0.93 | 1.00 | 1.08 | 0.98 | 1.00 | Normal |
| 296 | 1.06 | 1.02 | 1.00 | 1.04 | 0.96 | 1.00 | 1.00 | 0.94 | 1.00 | Normal |
| 297 | 0.98 | 1.00 | 1.00 | 0.94 | 0.87 | 1.00 | 1.03 | 1.07 | 1.00 | Normal |
| 298 | 1.03 | 1.00 | 1.00 | 1.12 | 1.09 | 1.00 | 1.02 | 1.02 | 1.00 | Normal |
| 299 | 0.98 | 0.96 | 1.00 | 1.00 | 1.05 | 1.00 | 0.93 | 0.96 | 1.00 | Normal |
| 300 | 0.69 | 0.75 | 1.00 | 0.98 | 0.99 | 1.00 | 1.09 | 1.07 | 1.00 | aneuploid (+C2) |
| 301 | 0.98 | 0.97 | 1.00 | 0.87 | 0.94 | 1.00 | 1.01 | 1.11 | 1.00 | Normal |
| 302 | 1.01 | 1.02 | 1.00 | 1.01 | 0.99 | 1.00 | 0.98 | 0.97 | 1.00 | Normal |
| 303 | 1.01 | 1.05 | 1.00 | 0.96 | 1.08 | 1.00 | 0.99 | 1.02 | 1.00 | Normal |
| 304 | 1.03 | 1.03 | 1.00 | 1.02 | 0.99 | 1.00 | 1.03 | 1.02 | 1.00 | Normal |
| 305 | 1.00 | 0.98 | 1.00 | 0.99 | 1.03 | 1.00 | 0.94 | 0.93 | 1.00 | Normal |
| 306 | 0.93 | 0.99 | 1.00 | 0.98 | 1.03 | 1.00 | 0.99 | 1.01 | 1.00 | Normal |
| 307 | 0.94 | 0.88 | 1.00 | 1.04 | 1.05 | 1.00 | 0.94 | 1.00 | 1.00 | Normal |
| 308 | 1.03 | 1.03 | 1.00 | 1.00 | 0.98 | 1.00 | 1.01 | 0.98 | 1.00 | Normal |
| 309 | 1.01 | 1.06 | 1.00 | 1.03 | 1.00 | 1.00 | 1.01 | 0.97 | 1.00 | Normal |
| 310 | 1.31 | 1.07 | 1.00 | 0.98 | 1.01 | 1.00 | 1.04 | 1.07 | 1.00 | aneuploid (+C6) |
| 311 | 0.98 | 1.00 | 1.00 | 1.01 | 1.03 | 1.00 | 1.07 | 1.04 | 1.00 | Normal |
| 312 | 0.94 | 0.94 | 1.00 | 0.97 | 1.01 | 1.00 | 1.01 | 1.00 | 1.00 | Normal |
| 313 | 1.07 | 1.03 | 1.00 | 1.04 | 0.96 | 1.00 | 1.04 | 1.06 | 1.00 | Normal |
| 314 | 1.06 | 1.08 | 1.00 | 1.02 | 1.06 | 1.00 | 0.96 | 1.00 | 1.00 | Normal |
| 315 | 1.03 | 0.98 | 1.00 | 1.00 | 1.05 | 1.00 | 0.99 | 1.06 | 1.00 | Normal |
| 316 | 1.00 | 1.04 | 1.00 | 0.96 | 1.00 | 1.00 | 0.95 | 0.93 | 1.00 | Normal |
| 317 | 1.06 | 0.94 | 1.00 | 0.96 | 0.98 | 1.00 | 0.91 | 0.99 | 1.00 | Normal |
| 318 | 1.01 | 1.02 | 1.00 | 0.96 | 1.04 | 1.00 | 0.95 | 0.94 | 1.00 | Normal |
| 319 | 1.00 | 0.98 | 1.00 | 1.03 | 0.88 | 1.00 | 0.96 | 0.92 | 1.00 | Normal |
| 320 | 0.95 | 0.92 | 1.00 | 1.07 | 1.04 | 1.00 | 1.03 | 0.97 | 1.00 | Normal |
| 321 | 1.07 | 0.99 | 1.00 | 1.00 | 0.98 | 1.00 | 0.98 | 0.87 | 1.00 | Normal |
| 322 | 1.03 | 0.99 | 1.00 | 1.08 | 1.07 | 1.00 | 1.00 | 0.97 | 1.00 | Normal |
| 323 | 1.05 | 0.98 | 1.00 | 0.98 | 1.08 | 1.00 | 0.91 | 0.96 | 1.00 | Normal |
| 324 | 0.98 | 0.92 | 1.00 | 1.03 | 1.04 | 1.00 | 1.06 | 0.99 | 1.00 | Normal |
| 325 | 1.08 | 1.04 | 1.00 | 1.00 | 0.95 | 1.00 | 0.98 | 0.98 | 1.00 | Normal |
| 326 | 0.99 | 1.02 | 1.00 | 1.06 | 1.02 | 1.00 | 1.06 | 0.94 | 1.00 | Normal |
| 327 | 0.98 | 0.97 | 1.00 | 0.98 | 0.99 | 1.00 | 0.97 | 1.00 | 1.00 | Normal |
| 328 | 1.05 | 0.98 | 1.00 | 1.01 | 1.11 | 1.00 | 1.04 | 0.97 | 1.00 | Normal |
| 329 | 1.06 | 1.01 | 1.00 | 1.04 | 0.98 | 1.00 | 0.90 | 0.98 | 1.00 | Normal |
| 330 | 1.03 | 0.99 | 1.00 | 1.01 | 1.03 | 1.00 | 0.89 | 0.94 | 1.00 | Normal |
| 331 | 0.98 | 0.97 | 1.00 | 1.04 | 0.95 | 1.00 | 0.93 | 0.98 | 1.00 | Normal |
| 332 | 1.03 | 1.01 | 1.00 | 0.96 | 1.04 | 1.00 | 0.99 | 1.01 | 1.00 | Normal |
| 333 | 1.09 | 1.00 | 1.00 | 1.03 | 1.07 | 1.00 | 1.02 | 0.96 | 1.00 | Normal |
| 334 | 1.02 | 0.99 | 1.00 | 0.94 | 1.07 | 1.00 | 0.91 | 0.98 | 1.00 | Normal |
| 335 | 0.97 | 0.98 | 1.00 | 0.97 | 0.90 | 1.00 | 0.97 | 1.02 | 1.00 | Normal |
| 336 | 0.91 | 0.96 | 1.00 | 0.99 | 1.02 | 1.00 | 0.99 | 1.00 | 1.00 | Normal |

TABLE 5-continued

Result of testing aneuploid in the F1 variety of cauliflower (raw data obtained by multiplex PCR based on the fluorescent probe method (value calculated by the ΔΔCt method))

| | C6C4C2 triplex PCR | | | C9C3C8 triplex PCR | | | C1C5C7 triplex PCR | | | |
|---|---|---|---|---|---|---|---|---|---|---|
| individual No. | C6 C6/C2 ΔΔCt | C4 C4/C2 ΔΔCt | C2 C2/C2 ΔΔCt | C9 C9/C8 ΔΔCt | C3 C3/C8 ΔΔCt | C8 C8/C8 ΔΔCt | C1 C1/C7 ΔΔCt | C5 C5/C7 ΔΔCt | C7 C7/C7 ΔΔCt | results |
| 337 | 1.02 | 0.98 | 1.00 | 1.10 | 1.05 | 1.00 | 1.09 | 0.99 | 1.00 | Normal |
| 338 | 0.92 | 0.93 | 1.00 | 1.07 | 0.89 | 1.00 | 0.99 | 1.04 | 1.00 | Normal |
| 339 | 0.99 | 1.03 | 1.00 | 0.99 | 0.97 | 1.00 | 1.09 | 0.96 | 1.00 | Normal |
| 340 | 1.00 | 1.07 | 1.00 | 1.02 | 0.99 | 1.00 | 0.97 | 1.00 | 1.00 | Normal |
| 341 | 1.01 | 0.98 | 1.00 | 1.05 | 1.01 | 1.00 | 0.93 | 0.86 | 1.00 | Normal |
| 342 | 0.96 | 1.04 | 1.00 | 0.98 | 0.90 | 1.00 | 0.94 | 0.95 | 1.00 | Normal |
| 343 | 1.11 | 1.08 | 1.00 | 0.97 | 1.02 | 1.00 | 0.95 | 1.00 | 1.00 | Normal |
| 344 | 0.97 | 1.01 | 1.00 | 0.98 | 0.93 | 1.00 | 1.04 | 0.99 | 1.00 | Normal |
| 345 | 0.88 | 1.03 | 1.00 | 1.01 | 0.90 | 1.00 | 1.04 | 1.03 | 1.00 | Normal |
| 346 | 0.95 | 1.07 | 1.00 | 0.98 | 0.90 | 1.00 | 1.04 | 0.97 | 1.00 | Normal |
| 347 | 0.93 | 0.92 | 1.00 | 1.01 | 0.95 | 1.00 | 1.09 | 1.10 | 1.00 | Normal |
| 348 | 0.87 | 0.91 | 1.00 | 1.05 | 1.00 | 1.00 | 0.96 | 0.98 | 1.00 | Normal |
| 349 | 0.95 | 1.01 | 1.00 | 1.02 | 1.00 | 1.00 | 0.96 | 0.98 | 1.00 | Normal |
| 350 | 0.94 | 0.91 | 1.00 | 0.93 | 0.99 | 1.00 | 1.06 | 1.08 | 1.00 | Normal |
| 351 | 0.98 | 1.03 | 1.00 | 0.97 | 0.96 | 1.00 | 0.97 | 1.02 | 1.00 | Normal |
| 352 | 0.90 | 0.96 | 1.00 | 1.02 | 0.97 | 1.00 | 0.98 | 0.96 | 1.00 | Normal |
| 353 | 1.31 | 1.07 | 1.00 | 1.00 | 0.92 | 1.00 | 1.09 | 1.08 | 1.00 | aneuploid (+C6) |
| 354 | 0.95 | 1.03 | 1.00 | 1.10 | 1.00 | 1.00 | 1.00 | 1.05 | 1.00 | Normal |
| 355 | 0.95 | 0.99 | 1.00 | 0.96 | 1.04 | 1.00 | 1.04 | 1.00 | 1.00 | Normal |
| 356 | 1.02 | 1.03 | 1.00 | 0.97 | 0.88 | 1.00 | 1.06 | 1.05 | 1.00 | Normal |
| 357 | 1.07 | 1.04 | 1.00 | 0.98 | 1.01 | 1.00 | 1.01 | 1.00 | 1.00 | Normal |
| 353 | 1.02 | 1.06 | 1.00 | 1.06 | 1.01 | 1.00 | 1.03 | 0.92 | 1.00 | Normal |
| 359 | 1.02 | 1.00 | 1.00 | 0.97 | 1.00 | 1.00 | 1.05 | 1.11 | 1.00 | Normal |
| 360 | 0.97 | 1.04 | 1.00 | 1.05 | 0.97 | 1.00 | 0.95 | 0.92 | 1.00 | Normal |
| 361 | 0.97 | 0.89 | 1.00 | 1.02 | 0.97 | 1.00 | 0.99 | 0.90 | 1.00 | Normal |
| 362 | 1.00 | 1.02 | 1.00 | 1.05 | 1.04 | 1.00 | 1.09 | 1.12 | 1.00 | Normal |
| 363 | 1.02 | 1.01 | 1.00 | 0.94 | 0.93 | 1.00 | 0.98 | 0.94 | 1.00 | Normal |
| 364 | 1.04 | 1.05 | 1.00 | 0.97 | 0.98 | 1.00 | 1.01 | 0.92 | 1.00 | Normal |
| 365 | 1.06 | 1.09 | 1.00 | 0.97 | 1.06 | 1.00 | 0.93 | 0.95 | 1.00 | Normal |
| 366 | 0.93 | 0.98 | 1.00 | 1.06 | 0.96 | 1.00 | 1.13 | 1.10 | 1.00 | Normal |
| 367 | 0.96 | 0.99 | 1.00 | 1.01 | 1.02 | 1.00 | 1.00 | 0.98 | 1.00 | Normal |
| 368 | 1.05 | 1.03 | 1.00 | 1.02 | 0.93 | 1.00 | 0.96 | 0.96 | 1.00 | Normal |
| 369 | 0.92 | 1.01 | 1.00 | 1.02 | 1.12 | 1.00 | 1.01 | 0.96 | 1.00 | Normal |
| 370 | 1.01 | 1.01 | 1.00 | 0.95 | 0.94 | 1.00 | 1.09 | 1.02 | 1.00 | Normal |
| 371 | 0.98 | 1.01 | 1.00 | 0.95 | 0.96 | 1.00 | 0.95 | 0.94 | 1.00 | Normal |
| 372 | 1.02 | 1.00 | 1.00 | 0.90 | 0.90 | 1.00 | 0.96 | 1.00 | 1.00 | Normal |
| 373 | 1.01 | 1.03 | 1.00 | 0.99 | 0.93 | 1.00 | 0.99 | 1.01 | 1.00 | Normal |
| 374 | 1.00 | 1.03 | 1.00 | 0.97 | 0.92 | 1.00 | 0.98 | 0.93 | 1.00 | Normal |
| 375 | 1.08 | 1.02 | 1.00 | 0.97 | 0.94 | 1.00 | 1.04 | 1.06 | 1.00 | Normal |
| 376 | 1.04 | 1.08 | 1.00 | 0.93 | 0.91 | 1.00 | 1.07 | 1.00 | 1.00 | Normal |
| 377 | 1.02 | 1.01 | 1.00 | 0.95 | 0.97 | 1.00 | 1.11 | 1.11 | 1.00 | Normal |
| 378 | 1.05 | 1.01 | 1.00 | 1.01 | 1.00 | 1.00 | 1.08 | 1.06 | 1.00 | Normal |
| 379 | 1.01 | 1.03 | 1.00 | 0.97 | 1.05 | 1.00 | 1.06 | 1.03 | 1.00 | Normal |
| 380 | 0.93 | 1.01 | 1.00 | 0.98 | 1.03 | 1.00 | 1.10 | 1.02 | 1.00 | Normal |
| 381 | 1.45 | 1.06 | 1.00 | 1.00 | 1.00 | 1.00 | 0.93 | 1.00 | 1.00 | aneuploid (+C6) |
| 382 | 0.95 | 0.96 | 1.00 | 0.99 | 0.90 | 1.00 | 0.97 | 1.08 | 1.00 | Normal |
| 383 | 1.06 | 1.01 | 1.00 | 0.99 | 1.01 | 1.00 | 0.99 | 0.96 | 1.00 | Normal |
| 384 | 1.07 | 1.01 | 1.00 | 1.00 | 1.06 | 1.00 | 1.00 | 1.00 | 1.00 | Normal |
| 385 | 0.94 | 0.90 | 1.00 | 0.98 | 1.04 | 1.00 | 1.03 | 1.04 | 1.00 | Normal |
| 386 | 0.97 | 0.96 | 1.00 | 0.93 | 0.91 | 1.00 | 1.01 | 0.99 | 1.00 | Normal |
| 387 | 0.93 | 1.02 | 1.00 | 1.00 | 1.01 | 1.00 | 0.91 | 0.94 | 1.00 | Normal |
| 388 | 1.02 | 0.97 | 1.00 | 1.00 | 0.95 | 1.00 | 1.12 | 1.00 | 1.00 | Normal |
| 389 | 1.04 | 1.03 | 1.00 | 1.02 | 0.96 | 1.00 | 0.93 | 0.94 | 1.00 | Normal |
| 390 | 1.04 | 1.01 | 1.00 | 1.03 | 1.07 | 1.00 | 1.04 | 1.07 | 1.00 | Normal |
| 391 | 1.02 | 1.08 | 1.00 | 1.05 | 1.02 | 1.00 | 1.00 | 0.96 | 1.00 | Normal |
| 392 | 0.98 | 0.91 | 1.00 | 1.02 | 0.92 | 1.00 | 1.05 | 0.95 | 1.00 | Normal |
| 393 | 0.91 | 0.89 | 1.00 | 0.98 | 1.07 | 1.00 | 1.00 | 0.94 | 1.00 | Normal |
| 394 | 0.99 | 1.02 | 1.00 | 1.02 | 1.01 | 1.00 | 1.27 | 1.05 | 1.00 | aneuploid (+C1) |
| 395 | 0.90 | 1.00 | 1.00 | 0.98 | 1.02 | 1.00 | 1.00 | 1.02 | 1.00 | Normal |
| 396 | 0.93 | 0.99 | 1.00 | 1.04 | 1.05 | 1.00 | 1.02 | 0.98 | 1.00 | Normal |
| 397 | 1.04 | 0.98 | 1.00 | 1.01 | 0.97 | 1.00 | 1.03 | 0.98 | 1.00 | Normal |
| 398 | 0.97 | 0.96 | 1.00 | 1.00 | 1.00 | 1.00 | 1.30 | 1.08 | 1.00 | aneuploid (+C1) |
| 399 | 0.97 | 0.97 | 1.00 | 1.06 | 1.10 | 1.00 | 1.03 | 1.08 | 1.00 | Normal |
| 400 | 0.96 | 1.00 | 1.00 | 1.06 | 0.97 | 1.00 | 1.00 | 0.98 | 1.00 | Normal |
| 401 | 0.97 | 1.01 | 1.00 | 1.01 | 1.00 | 1.00 | 1.04 | 1.03 | 1.00 | Normal |
| 402 | 0.99 | 0.96 | 1.00 | 0.90 | 0.97 | 1.00 | 0.95 | 0.98 | 1.00 | Normal |
| 403 | 1.00 | 1.03 | 1.00 | 1.05 | 0.96 | 1.00 | 1.09 | 1.13 | 1.00 | Normal |
| 404 | 1.14 | 1.08 | 1.00 | 0.99 | 0.96 | 1.00 | 0.95 | 0.98 | 1.00 | Normal |
| 405 | 1.10 | 0.96 | 1.00 | 1.04 | 0.97 | 1.00 | 0.95 | 1.00 | 1.00 | Normal |
| 406 | 0.97 | 1.02 | 1.00 | 1.03 | 1.07 | 1.00 | 1.07 | 1.00 | 1.00 | Normal |
| 407 | 0.99 | 1.01 | 1.00 | 1.00 | 1.00 | 1.00 | 1.04 | 0.95 | 1.00 | Normal |

TABLE 5-continued

Result of testing aneuploid in the F1 variety of cauliflower (raw data obtained by multiplex PCR based on the fluorescent probe method (value calculated by the ΔΔCt method))

| | C6C4C2 triplex PCR | | | C9C3C8 triplex PCR | | | C1C5C7 triplex PCR | | | |
|---|---|---|---|---|---|---|---|---|---|---|
| individual No. | C6 C6/C2 ΔΔCt | C4 C4/C2 ΔΔCt | C2 C2/C2 ΔΔCt | C9 C9/C8 ΔΔCt | C3 C3/C8 ΔΔCt | C8 C8/C8 ΔΔCt | C1 C1/C7 ΔΔCt | C5 C5/C7 ΔΔCt | C7 C7/C7 ΔΔCt | results |
| 408 | 0.93 | 0.89 | 1.00 | 1.01 | 1.01 | 1.00 | 1.00 | 0.99 | 1.00 | Normal |
| 409 | 1.01 | 0.95 | 1.00 | 0.99 | 0.97 | 1.00 | 0.97 | 0.94 | 1.00 | Normal |
| 410 | 1.04 | 1.03 | 1.00 | 0.99 | 0.98 | 1.00 | 0.96 | 1.00 | 1.00 | Normal |
| 411 | 1.02 | 1.02 | 1.00 | 0.93 | 0.90 | 1.00 | 0.96 | 1.00 | 1.00 | Normal |
| 412 | 1.00 | 1.01 | 1.00 | 0.96 | 0.93 | 1.00 | 1.01 | 1.01 | 1.00 | Normal |
| 413 | 0.96 | 1.03 | 1.00 | 1.03 | 1.08 | 1.00 | 1.04 | 0.98 | 1.00 | Normal |
| 414 | 1.02 | 0.98 | 1.00 | 1.01 | 1.07 | 1.00 | 1.00 | 1.03 | 1.00 | Normal |
| 415 | 0.99 | 0.98 | 1.00 | 1.01 | 1.07 | 1.00 | 1.04 | 1.09 | 1.00 | Normal |
| 416 | 1.07 | 1.02 | 1.00 | 1.04 | 1.13 | 1.00 | 1.01 | 0.97 | 1.00 | Normal |
| 417 | 0.99 | 1.03 | 1.00 | 1.04 | 1.01 | 1.00 | 0.95 | 1.00 | 1.00 | Normal |
| 418 | 1.01 | 1.01 | 1.00 | 1.03 | 1.08 | 1.00 | 0.99 | 0.98 | 1.00 | Normal |
| 419 | 0.99 | 1.04 | 1.00 | 1.01 | 1.03 | 1.00 | 0.98 | 1.01 | 1.00 | Normal |
| 420 | 1.01 | 0.99 | 1.00 | 0.99 | 0.98 | 1.00 | 0.92 | 0.96 | 1.00 | Normal |
| 421 | 0.95 | 0.94 | 1.00 | 0.98 | 0.94 | 1.00 | 0.97 | 1.00 | 1.00 | Normal |
| 422 | 0.88 | 0.91 | 1.00 | 1.01 | 1.00 | 1.00 | 0.94 | 1.00 | 1.00 | Normal |
| 423 | 1.00 | 1.02 | 1.00 | 0.95 | 1.00 | 1.00 | 0.97 | 0.98 | 1.00 | Normal |
| 424 | 1.03 | 0.99 | 1.00 | 0.99 | 1.04 | 1.00 | 1.04 | 1.07 | 1.00 | Normal |
| 425 | 0.96 | 0.92 | 1.00 | 0.97 | 1.00 | 1.00 | 1.01 | 0.97 | 1.00 | Normal |
| 426 | 1.08 | 1.02 | 1.00 | 1.04 | 1.00 | 1.00 | 0.95 | 0.98 | 1.00 | Normal |
| 427 | 1.05 | 1.05 | 1.00 | 1.05 | 1.03 | 1.00 | 0.92 | 0.96 | 1.00 | Normal |
| 428 | 1.00 | 1.01 | 1.00 | 1.05 | 1.02 | 1.00 | 0.92 | 0.94 | 1.00 | Normal |
| 429 | 0.93 | 0.98 | 1.00 | 1.02 | 1.04 | 1.00 | 1.08 | 0.98 | 1.00 | Normal |
| 430 | 1.03 | 1.01 | 1.00 | 0.97 | 0.93 | 1.00 | 1.01 | 1.03 | 1.00 | Normal |
| 431 | 0.92 | 0.98 | 1.00 | 1.03 | 1.00 | 1.00 | 1.05 | 1.13 | 1.00 | Normal |
| 432 | 0.97 | 1.06 | 1.00 | 0.99 | 0.90 | 1.00 | 1.03 | 0.99 | 1.00 | Normal |
| 433 | 1.04 | 0.95 | 1.00 | 1.02 | 1.03 | 1.00 | 1.00 | 0.99 | 1.00 | Normal |
| 434 | 1.00 | 1.03 | 1.00 | 1.00 | 1.04 | 1.00 | 0.95 | 0.98 | 1.00 | Normal |
| 435 | 1.05 | 0.99 | 1.00 | 1.00 | 1.07 | 1.00 | 1.05 | 0.99 | 1.00 | Normal |
| 435 | 0.98 | 0.97 | 1.00 | 1.03 | 0.94 | 1.00 | 1.02 | 0.98 | 1.00 | Normal |
| 437 | 0.99 | 1.07 | 1.00 | 0.95 | 0.99 | 1.00 | 0.76 | 0.73 | 1.00 | aneuploid (+C7) |
| 438 | 1.07 | 1.01 | 1.00 | 1.03 | 1.02 | 1.00 | 0.95 | 1.00 | 1.00 | Normal |
| 439 | 1.06 | 1.01 | 1.00 | 1.02 | 0.88 | 1.00 | 1.00 | 1.05 | 1.00 | Normal |
| 440 | 0.93 | 0.96 | 1.00 | 0.97 | 0.97 | 1.00 | 0.68 | 0.93 | 1.00 | aneuploid (others) |
| 441 | 1.03 | 1.01 | 1.00 | 0.92 | 0.92 | 1.00 | 1.11 | 1.06 | 1.00 | Normal |
| 442 | 1.03 | 1.08 | 1.00 | 0.95 | 1.00 | 1.00 | 0.93 | 0.96 | 1.00 | Normal |
| 443 | 0.95 | 0.92 | 1.00 | 0.95 | 1.03 | 1.00 | 1.02 | 1.11 | 1.00 | Normal |
| 444 | 0.93 | 0.91 | 1.00 | 1.00 | 0.96 | 1.00 | 0.99 | 0.99 | 1.00 | Normal |
| 445 | 0.99 | 1.01 | 1.00 | 1.01 | 0.97 | 1.00 | 1.04 | 0.98 | 1.00 | Normal |
| 446 | 0.95 | 0.96 | 1.00 | 1.01 | 0.97 | 1.00 | 1.09 | 0.98 | 1.00 | Normal |
| 447 | 1.00 | 0.99 | 1.00 | 1.13 | 1.05 | 1.00 | 1.10 | 1.03 | 1.00 | Normal |
| 448 | 0.99 | 1.00 | 1.00 | 0.99 | 0.93 | 1.00 | 0.97 | 1.04 | 1.00 | Normal |
| 449 | 1.04 | 0.94 | 1.00 | 1.07 | 1.04 | 1.00 | 1.08 | 1.02 | 1.00 | Normal |
| 450 | 1.02 | 1.01 | 1.00 | 1.02 | 1.02 | 1.00 | 0.92 | 0.98 | 1.00 | Normal |
| 451 | 1.00 | 1.06 | 1.00 | 1.02 | 1.00 | 1.00 | 0.99 | 0.906 | 1.00 | Normal |
| 452 | 1.08 | 1.01 | 1.00 | 1.01 | 1.02 | 1.00 | 0.95 | 0.95 | 1.00 | Normal |
| 453 | 1.09 | 1.05 | 1.00 | 1.07 | 1.10 | 1.00 | 0.98 | 0.96 | 1.00 | Normal |
| 454 | 0.97 | 1.01 | 1.00 | 0.94 | 0.90 | 1.00 | 0.97 | 1.00 | 1.00 | Normal |
| 455 | 1.04 | 0.98 | 1.00 | 1.07 | 1.09 | 1.00 | 1.01 | 0.98 | 1.00 | Normal |
| 456 | 0.96 | 0.91 | 1.00 | 1.03 | 1.06 | 1.00 | 1.04 | 0.94 | 1.00 | Normal |
| 457 | 1.02 | 1.01 | 1.00 | 1.02 | 1.01 | 1.00 | 1.08 | 1.04 | 1.00 | Normal |
| 458 | 0.99 | 1.04 | 1.00 | 0.94 | 0.94 | 1.00 | 0.98 | 0.97 | 1.00 | Normal |
| 459 | 0.92 | 0.96 | 1.00 | 1.01 | 0.99 | 1.00 | 0.96 | 0.96 | 1.00 | Normal |
| 460 | 0.97 | 0.98 | 1.00 | 0.99 | 0.95 | 1.00 | 1.04 | 1.00 | 1.00 | Normal |
| 461 | 0.96 | 0.93 | 1.00 | 1.00 | 1.00 | 1.00 | 0.97 | 0.91 | 1.00 | Normal |
| 462 | 1.00 | 0.97 | 1.00 | 0.93 | 1.04 | 1.00 | 0.94 | 1.00 | 1.00 | Normal |
| 463 | 0.99 | 1.02 | 1.00 | 1.03 | 1.01 | 1.00 | 1.01 | 0.95 | 1.00 | Normal |
| 464 | 1.01 | 1.04 | 1.00 | 0.99 | 0.95 | 1.00 | 1.02 | 0.97 | 1.00 | Normal |
| 465 | 0.99 | 1.01 | 1.00 | 1.01 | 1.00 | 1.00 | 0.90 | 0.98 | 1.00 | Normal |
| 466 | 0.88 | 0.94 | 1.00 | 1.02 | 1.08 | 1.00 | 0.99 | 1.05 | 1.00 | Normal |
| 467 | 0.97 | 0.94 | 1.00 | 1.01 | 1.09 | 1.00 | 1.03 | 1.05 | 1.00 | Normal |
| 468 | 1.04 | 1.01 | 1.00 | 1.02 | 1.00 | 1.00 | 0.98 | 1.04 | 1.00 | Normal |
| 469 | 1.04 | 1.07 | 1.00 | 1.02 | 1.10 | 1.00 | 1.03 | 1.11 | 1.00 | Normal |
| 470 | 0.95 | 0.96 | 1.00 | 1.02 | 1.02 | 1.00 | 0.97 | 1.02 | 1.00 | Normal |
| 471 | 0.98 | 0.94 | 1.00 | 0.99 | 1.04 | 1.00 | 1.01 | 1.01 | 1.00 | Normal |
| 472 | 0.97 | 0.98 | 1.00 | 1.04 | 1.01 | 1.00 | 1.05 | 1.02 | 1.00 | Normal |
| 473 | 1.07 | 1.03 | 1.00 | 1.02 | 1.05 | 1.00 | 1.08 | 1.11 | 1.00 | Normal |
| 474 | 0.93 | 0.96 | 1.00 | 0.95 | 1.03 | 1.00 | 1.05 | 1.00 | 1.00 | Normal |
| 475 | 0.97 | 0.94 | 1.00 | 1.07 | 1.02 | 1.00 | 1.01 | 1.00 | 1.00 | Normal |
| 476 | 0.99 | 0.98 | 1.00 | 0.89 | 0.93 | 1.00 | 0.99 | 1.02 | 1.00 | Normal |
| 477 | 0.95 | 0.98 | 1.00 | 1.04 | 1.04 | 1.00 | 0.93 | 0.94 | 1.00 | Normal |
| 478 | 1.07 | 1.05 | 1.00 | 1.04 | 1.09 | 1.00 | 1.06 | 1.08 | 1.00 | Normal |

TABLE 5-continued

Result of testing aneuploid in the F1 variety of cauliflower (raw data obtained by multiplex PCR based on the fluorescent probe method (value calculated by the ΔΔCt method))

| | C6C4C2 triplex PCR | | | C9C3C8 triplex PCR | | | C1C5C7 triplex PCR | | | |
|---|---|---|---|---|---|---|---|---|---|---|
| individual No. | C6 C6/C2 ΔΔCt | C4 C4/C2 ΔΔCt | C2 C2/C2 ΔΔCt | C9 C9/C8 ΔΔCt | C3 C3/C8 ΔΔCt | C8 C8/C8 ΔΔCt | C1 C1/C7 ΔΔCt | C5 C5/C7 ΔΔCt | C7 C7/C7 ΔΔCt | results |
| 479 | 0.94 | 0.99 | 1.00 | 0.97 | 1.09 | 1.00 | 0.96 | 0.98 | 1.00 | Normal |
| 480 | 1.11 | 1.03 | 1.00 | 0.96 | 1.00 | 1.00 | 0.97 | 1.02 | 1.00 | Normal |
| 481 | 1.01 | 1.02 | 1.00 | 1.03 | 1.04 | 1.00 | 1.01 | 0.98 | 1.00 | Normal |
| 482 | 0.99 | 1.05 | 1.00 | 1.05 | 1.05 | 1.00 | 0.98 | 1.00 | 1.00 | Normal |
| 483 | 0.98 | 0.94 | 1.00 | 1.02 | 1.10 | 1.00 | 0.99 | 0.93 | 1.00 | Normal |
| 484 | 0.97 | 1.01 | 1.00 | 0.95 | 0.92 | 1.00 | 0.92 | 0.88 | 1.00 | Normal |
| 485 | 0.97 | 1.00 | 1.00 | 1.06 | 1.02 | 1.00 | 1.03 | 0.97 | 1.00 | Normal |
| 486 | 0.99 | 1.03 | 1.00 | 1.02 | 1.11 | 1.00 | 1.04 | 1.00 | 1.00 | Normal |
| 487 | 1.05 | 1.06 | 1.00 | 0.97 | 1.04 | 1.00 | 1.08 | 1.14 | 1.00 | Normal |
| 488 | 1.04 | 1.01 | 1.00 | 0.95 | 0.96 | 1.00 | 1.07 | 1.01 | 1.00 | Normal |
| 489 | 0.95 | 0.98 | 1.00 | 0.99 | 1.02 | 1.00 | 1.02 | 0.84 | 1.00 | Normal |
| 490 | 0.99 | 0.98 | 1.00 | 0.98 | 1.12 | 1.00 | 1.09 | 1.06 | 1.00 | Normal |
| 491 | 1.01 | 0.99 | 1.00 | 0.96 | 1.02 | 1.00 | 0.98 | 1.00 | 1.00 | Normal |
| 492 | 0.96 | 1.04 | 1.00 | 1.01 | 0.97 | 1.00 | 0.98 | 1.03 | 1.00 | Normal |
| 493 | 1.06 | 1.08 | 1.00 | 0.99 | 1.10 | 1.00 | 1.06 | 1.05 | 1.00 | Normal |
| 494 | 1.04 | 1.04 | 1.00 | 0.95 | 1.01 | 1.00 | 1.01 | 1.05 | 1.00 | Normal |
| 495 | 1.04 | 1.01 | 1.00 | 1.02 | 1.05 | 1.00 | 1.09 | 1.06 | 1.00 | Normal |
| 496 | 0.91 | 0.89 | 1.00 | 1.01 | 1.01 | 1.00 | 0.94 | 0.94 | 1.00 | Normal |
| 497 | 1.11 | 1.10 | 1.00 | 1.06 | 1.03 | 1.00 | 0.94 | 0.97 | 1.00 | Normal |
| 498 | 0.95 | 0.96 | 1.00 | 1.06 | 1.08 | 1.00 | 0.97 | 1.00 | 1.00 | Normal |
| 499 | 1.02 | 0.98 | 1.00 | 1.04 | 1.03 | 1.00 | 0.99 | 0.98 | 1.00 | Normal |
| 500 | 1.09 | 1.06 | 1.00 | 1.00 | 1.04 | 1.00 | 0.95 | 1.02 | 1.00 | Normal |
| 501 | 1.08 | 1.05 | 1.00 | 0.96 | 1.01 | 1.00 | 0.98 | 1.00 | 1.00 | Normal |
| 502 | 0.98 | 0.96 | 1.00 | 0.95 | 1.00 | 1.00 | 1.06 | 1.11 | 1.00 | Normal |
| 503 | 0.90 | 0.95 | 1.00 | 0.98 | 1.04 | 1.00 | 0.95 | 0.99 | 1.00 | Normal |
| 504 | 0.97 | 0.98 | 1.00 | 0.99 | 1.09 | 1.00 | 0.90 | 0.96 | 1.00 | Normal |
| 505 | 0.98 | 0.96 | 1.00 | 0.99 | 1.10 | 1.00 | 0.93 | 1.05 | 1.00 | Normal |
| 506 | 0.95 | 0.91 | 1.00 | 0.96 | 0.99 | 1.00 | 0.98 | 0.92 | 1.00 | Normal |
| 507 | 1.02 | 0.98 | 1.00 | 1.03 | 1.07 | 1.00 | 1.04 | 0.96 | 1.00 | Normal |
| 508 | 1.00 | 0.94 | 1.00 | 0.94 | 0.99 | 1.00 | 0.99 | 1.02 | 1.00 | Normal |
| 509 | 0.99 | 1.03 | 1.00 | 0.97 | 1.05 | 1.00 | 0.98 | 0.66 | 1.00 | aneuploid (others) |
| 510 | 0.68 | 0.71 | 1.00 | 1.02 | 1.04 | 1.00 | 0.98 | 1.00 | 1.00 | aneuploid (+C2) |
| 511 | 0.99 | 0.95 | 1.00 | 0.95 | 0.97 | 1.00 | 0.95 | 1.02 | 1.00 | Normal |
| 512 | 1.04 | 1.03 | 1.00 | 1.00 | 1.13 | 1.00 | 1.03 | 1.08 | 1.00 | Normal |
| 513 | 1.00 | 1.04 | 1.00 | 0.95 | 0.98 | 1.00 | 0.96 | 1.00 | 1.00 | Normal |
| 514 | 0.96 | 0.96 | 1.00 | 0.95 | 0.94 | 1.00 | 0.92 | 0.96 | 1.00 | Normal |
| 515 | 1.08 | 1.03 | 1.00 | 1.04 | 1.03 | 1.00 | 0.95 | 1.05 | 1.00 | Normal |
| 516 | 1.02 | 1.08 | 1.00 | 0.90 | 1.05 | 1.00 | 1.00 | 1.01 | 1.00 | Normal |
| 517 | 1.05 | 0.96 | 1.00 | 1.01 | 0.90 | 1.00 | 0.97 | 0.96 | 1.00 | Normal |
| 518 | 0.94 | 0.97 | 1.00 | 0.95 | 0.92 | 1.00 | 0.90 | 0.93 | 1.00 | Normal |
| 519 | 1.02 | 1.07 | 1.00 | 1.01 | 0.92 | 1.00 | 0.97 | 0.95 | 1.00 | Normal |
| 520 | 1.04 | 1.03 | 1.00 | 1.14 | 1.07 | 1.00 | 0.99 | 1.05 | 1.00 | Normal |
| 521 | 1.01 | 1.03 | 1.00 | 1.00 | 0.95 | 1.00 | 0.99 | 1.05 | 1.00 | Normal |
| 522 | 1.09 | 1.01 | 1.00 | 0.99 | 0.92 | 1.00 | 0.95 | 0.98 | 1.00 | Normal |
| 523 | 0.99 | 1.01 | 1.00 | 1.04 | 1.05 | 1.00 | 1.03 | 0.98 | 1.00 | Normal |
| 524 | 1.07 | 1.09 | 1.00 | 1.02 | 0.95 | 1.00 | 1.04 | 1.02 | 1.00 | Normal |
| 525 | 1.07 | 1.08 | 1.00 | 1.03 | 0.96 | 1.00 | 1.03 | 1.01 | 1.00 | Normal |
| 526 | 1.04 | 0.98 | 1.00 | 0.99 | 1.01 | 1.00 | 1.04 | 1.02 | 1.00 | Normal |
| 527 | 0.99 | 1.02 | 1.00 | 0.93 | 0.95 | 1.00 | 0.91 | 0.99 | 1.00 | Normal |
| 528 | 1.02 | 0.98 | 1.00 | 0.87 | 0.95 | 1.00 | 1.03 | 1.05 | 1.00 | Normal |
| 529 | 0.96 | 0.95 | 1.00 | 0.96 | 0.91 | 1.00 | 0.98 | 0.89 | 1.00 | Normal |
| 530 | 1.07 | 1.06 | 1.00 | 1.02 | 1.00 | 1.00 | 1.06 | 1.09 | 1.00 | Normal |
| 531 | 0.97 | 0.95 | 1.00 | 1.01 | 0.93 | 1.00 | 0.94 | 0.98 | 1.00 | Normal |
| 532 | 1.05 | 1.06 | 1.00 | 1.02 | 0.97 | 1.00 | 0.98 | 1.03 | 1.00 | Normal |
| 533 | 0.97 | 1.04 | 1.00 | 0.96 | 0.95 | 1.00 | 1.02 | 0.98 | 1.00 | Normal |
| 534 | 1.01 | 1.01 | 1.00 | 1.07 | 0.95 | 1.00 | 0.97 | 0.99 | 1.00 | Normal |
| 535 | 0.93 | 0.94 | 1.00 | 1.07 | 1.00 | 1.00 | 0.90 | 0.96 | 1.00 | Normal |
| 536 | 0.97 | 1.01 | 1.00 | 1.01 | 1.01 | 1.00 | 1.00 | 1.00 | 1.00 | Normal |
| 537 | 0.95 | 0.93 | 1.00 | 1.06 | 1.03 | 1.00 | 0.97 | 0.96 | 1.00 | Normal |
| 538 | 1.04 | 1.02 | 1.00 | 0.97 | 1.00 | 1.00 | 0.90 | 0.92 | 1.00 | Normal |
| 539 | 1.00 | 1.03 | 1.00 | 1.01 | 0.89 | 1.00 | 1.04 | 1.09 | 1.00 | Normal |
| 540 | 0.99 | 1.01 | 1.00 | 0.95 | 0.96 | 1.00 | 0.91 | 1.00 | 1.00 | Normal |
| 541 | 1.03 | 1.01 | 1.00 | 0.99 | 0.99 | 1.00 | 1.04 | 1.04 | 1.00 | Normal |
| 542 | 1.02 | 0.97 | 1.00 | 1.03 | 1.01 | 1.00 | 1.00 | 1.03 | 1.00 | Normal |
| 543 | 1.08 | 1.04 | 1.00 | 0.97 | 1.00 | 1.00 | 0.93 | 0.95 | 1.00 | Normal |
| 544 | 0.91 | 0.92 | 1.00 | 0.97 | 0.95 | 1.00 | 1.01 | 1.03 | 1.00 | Normal |
| 545 | 1.02 | 0.96 | 1.00 | 1.02 | 1.14 | 1.00 | 0.93 | 0.94 | 1.00 | Normal |
| 546 | 1.02 | 0.98 | 1.00 | 0.95 | 0.94 | 1.00 | 1.04 | 1.05 | 1.00 | Normal |
| 547 | 0.94 | 1.01 | 1.00 | 0.93 | 0.98 | 1.00 | 0.99 | 1.05 | 1.00 | Normal |
| 548 | 0.99 | 1.01 | 1.00 | 0.94 | 1.02 | 1.00 | 0.94 | 0.99 | 1.00 | Normal |
| 549 | 0.95 | 0.98 | 1.00 | 0.97 | 0.99 | 1.00 | 0.99 | 0.96 | 1.00 | Normal |

TABLE 5-continued

Result of testing aneuploid in the F1 variety of cauliflower (raw data obtained by multiplex PCR based on the fluorescent probe method (value calculated by the ΔΔCt method))

| | C6C4C2 triplex PCR | | | C9C3C8 triplex PCR | | | C1C5C7 triplex PCR | | | |
|---|---|---|---|---|---|---|---|---|---|---|
| individual No. | C6 C6/C2 ΔΔCt | C4 C4/C2 ΔΔCt | C2 C2/C2 ΔΔCt | C9 C9/C8 ΔΔCt | C3 C3/C8 ΔΔCt | C8 C8/C8 ΔΔCt | C1 C1/C7 ΔΔCt | C5 C5/C7 ΔΔCt | C7 C7/C7 ΔΔCt | results |
| 550 | 0.99 | 1.00 | 1.00 | 0.98 | 0.97 | 1.00 | 0.98 | 0.97 | 1.00 | Normal |
| 551 | 1.10 | 1.03 | 1.00 | 1.02 | 1.00 | 1.00 | 0.97 | 0.97 | 1.00 | Normal |
| 552 | 1.04 | 1.01 | 1.00 | 0.99 | 1.12 | 1.00 | 1.01 | 1.02 | 1.00 | Normal |
| 553 | 1.41 | 1.10 | 1.00 | 1.01 | 1.00 | 1.00 | 1.03 | 1.10 | 1.00 | aneuploid (+C6) |
| 554 | 1.04 | 1.03 | 1.00 | 0.93 | 1.01 | 1.00 | 0.95 | 0.99 | 1.00 | Normal |
| 555 | 1.02 | 1.00 | 1.00 | 1.04 | 1.05 | 1.00 | 0.98 | 0.99 | 1.00 | Normal |
| 556 | 1.03 | 1.01 | 1.00 | 0.99 | 1.04 | 1.00 | 0.99 | 1.00 | 1.00 | Normal |
| 557 | 0.99 | 1.02 | 1.00 | 1.02 | 1.07 | 1.00 | 0.95 | 0.94 | 1.00 | Normal |
| 558 | 0.93 | 0.96 | 1.00 | 1.02 | 1.01 | 1.00 | 0.93 | 0.95 | 1.00 | Normal |
| 559 | 1.02 | 1.05 | 1.00 | 1.05 | 1.05 | 1.00 | 1.03 | 0.98 | 1.00 | Normal |
| 560 | 1.02 | 1.05 | 1.00 | 1.05 | 1.10 | 1.00 | 1.03 | 1.01 | 1.00 | Normal |
| 561 | 1.07 | 1.03 | 1.00 | 0.99 | 1.01 | 1.00 | 0.98 | 0.98 | 1.00 | Normal |
| 562 | 0.96 | 0.93 | 1.00 | 0.97 | 1.03 | 1.00 | 0.98 | 0.94 | 1.00 | Normal |
| 563 | 0.93 | 0.96 | 1.00 | 1.04 | 1.14 | 1.00 | 0.93 | 0.98 | 1.00 | Normal |
| 564 | 1.13 | 1.09 | 1.00 | 1.04 | 1.03 | 1.00 | 1.04 | 1.08 | 1.00 | Normal |

TABLE 6

Result of testing aneuploid in the F1 variety of cauliflower by the TaqMan method (summary)

| | Number of plants | ratio (%) |
|---|---|---|
| Normal | 542 | 96.1% |
| aneuploid (+C1) | 4 | 0.7% |
| aneuploid (+C2) | 5 | 0.9% |
| aneuploid (+C3) | 0 | 0.0% |
| aneuploid (+C4) | 1 | 0.2% |
| aneuploid (+C5) | 0 | 0.0% |
| aneuploid (+C6) | 7 | 1.2% |
| aneuploid (+C7) | 2 | 0.4% |
| aneuploid (+C8) | 0 | 0.0% |
| aneuploid (+C9) | 1 | 0.2% |
| other aneuploid | 2 | 0.4% |

Example 5 Example of Detection of Off-Types in Cabbage

Individuals showing morphology differing from the normal appearance at harvest stage were selected from the cultivation field of the F1 variety of cabbage "SCB-81" under development by SAKATA SEED CORPORATION. DNA was extracted from mature leaves of each plant and the analysis of aneuploids was performed in the same manner as in Example 4 above.

The results were as shown in Table 7.

As a result, all the trisomic plants, other than chromosome 3, were detected, and it was revealed that the aneuploidy of chromosomes also caused the majority of off-type individuals in cabbage.

These facts demonstrate that the method of the present invention is effective to analyze off-type individuals of not only broccoli and cauliflower but also cabbage.

Figure 6:
FIG. 6 shows phenotypes of aneuploids from a cabbage variety, where in the figure, (A) represents a normal individual (Normal), (B) represents chromosome 1 trisomy (+C1), (C) represents chromosome 2 trisomy (+C2), (D) represents chromosome 4 trisomy (+C4), (E) represents chromosome 5 trisomy (+C5), (F) represents chromosome 6 trisomy (+C6), (G) represents chromosome 7 trisomy (+C7), (H) represents chromosome 8 trisomy (+C8), and (I) represents chromosome 9 trisomy (+C9), and (3) represents an individual with aneuploidy on chromosome 1 and chromosome 2 (+C1, +C2), (K) represents an individual with aneuploidy on chromosome 1 and chromosome 8 (+C1, +C8), and (L) represents an individual with aneuploidy on chromosome 5 and chromosome 8 (+C5, +C8)
Figure 6:

FIG. 6 shows the appearance of various aneuploids (phenotypic characteristics of chromosome trisomies were as shown in FIG. 7). As shown in FIG. 6 and Table 7, in addition to typical trisomies, there were also individuals in which aneuploidy occurred in a plurality of chromosomes.

TABLE 7

Result of testing aneuploid in the F1 variety of cabbage (raw data obtained by multiplex PCR based on the fluorescent probe method (value calculated by the ΔΔCt method))

| | C6C4C2 triplex PCR | | | C9C3C8 triplex PCR | | | C1C5C7 triplex PCR | | | |
|---|---|---|---|---|---|---|---|---|---|---|
| individual No. | C6 C6/C2 ΔΔCt | C4 C4/C2 ΔΔCt | C2 C2/C2 ΔΔCt | C9 C9/C8 ΔΔCt | C3 C3/C8 ΔΔCt | C8 C8/C8 ΔΔCt | C1 C1/C7 ΔΔCt | C5 C5/C7 ΔΔCt | C7 C7/C7 ΔΔCt | results |
| 1 | 1.03 | 1.03 | 1.00 | 0.95 | 0.95 | 1.00 | 1.04 | 1.03 | 1.00 | Normal |
| 2 | 0.96 | 0.98 | 1.00 | 0.99 | 1.03 | 1.00 | 1.02 | 0.95 | 1.00 | Normal |
| 3 | 1.04 | 1.03 | 1.00 | 0.97 | 1.02 | 1.00 | 1.00 | 1.05 | 1.00 | Normal |
| 4 | 0.96 | 0.96 | 1.00 | 1.04 | 0.94 | 1.00 | 0.94 | 0.97 | 1.00 | Normal |
| 5 | 1.07 | 1.03 | 1.00 | 1.02 | 1.03 | 1.00 | 1.02 | 1.01 | 1.00 | Normal |
| 6 | 0.94 | 0.97 | 1.00 | 1.04 | 1.02 | 1.00 | 0.99 | 1.00 | 1.00 | Normal |
| 7 | 1.32 | 0.99 | 1.00 | 0.99 | 0.96 | 1.00 | 1.07 | 1.03 | 1.00 | aneuploid (+C6) |
| 8 | 1.05 | 1.01 | 1.00 | 1.04 | 0.95 | 1.00 | 0.75 | 0.76 | 1.00 | aneuploid (+C7) |
| 9 | 1.34 | 0.97 | 1.00 | 1.05 | 1.03 | 1.00 | 1.04 | 1.05 | 1.00 | aneuploid (+C6) |
| 10 | 1.02 | 1.38 | 1.00 | 1.01 | 1.03 | 1.00 | 1.05 | 0.99 | 1.00 | aneuploid (+C4) |
| 11 | 0.99 | 0.98 | 1.00 | 1.03 | 1.05 | 1.00 | 1.32 | 1.07 | 1.00 | aneuploid (+C1) |
| 12 | 0.71 | 0.72 | 1.00 | 1.01 | 0.96 | 1.00 | 0.98 | 0.99 | 1.00 | aneuploid (+C2) |
| 13 | 0.74 | 0.75 | 1.00 | 0.95 | 1.04 | 1.00 | 1.30 | 1.03 | 1.00 | aneuploid (+C1, +C2) |

TABLE 7-continued

Result of testing aneuploid in the F1 variety of cabbage (raw data obtained by multiplex
PCR based on the fluorescent probe method (value calculated by the ΔΔCt method))

| | C6C4C2 triplex PCR | | | C9C3C8 triplex PCR | | | C1C5C7 triplex PCR | | | |
|---|---|---|---|---|---|---|---|---|---|---|
| individual No. | C6 C6/C2 ΔΔCt | C4 C4/C2 ΔΔCt | C2 C2/C2 ΔΔCt | C9 C9/C8 ΔΔCt | C3 C3/C8 ΔΔCt | C8 C8/C8 ΔΔCt | C1 C1/C7 ΔΔCt | C5 C5/C7 ΔΔCt | C7 C7/C7 ΔΔCt | results |
| 14 | 0.93 | 0.97 | 1.00 | 1.00 | 0.89 | 1.00 | 1.04 | 1.30 | 1.00 | aneuploid (+C5) |
| 15 | 0.72 | 0.72 | 1.00 | 1.00 | 0.95 | 1.00 | 1.00 | 0.99 | 1.00 | aneuploid (+C2) |
| 16 | 1.35 | 0.95 | 1.00 | 1.00 | 1.09 | 1.00 | 1.02 | 1.02 | 1.00 | aneuploid (+C6) |
| 17 | 0.96 | 0.98 | 1.00 | 0.74 | 0.79 | 1.00 | 1.03 | 1.02 | 1.00 | aneuploid (+C8) |
| 18 | 1.02 | 0.98 | 1.00 | 1.28 | 1.02 | 1.00 | 1.00 | 1.03 | 1.00 | aneuploid (+C9) |
| 19 | 0.75 | 0.74 | 1.00 | 1.00 | 0.96 | 1.00 | 1.04 | 1.03 | 1.00 | aneuploid (+C2) |
| 20 | 0.93 | 1.05 | 1.00 | 0.97 | 0.91 | 1.00 | 0.79 | 0.79 | 1.00 | aneuploid (+C7) |
| 21 | 0.97 | 1.00 | 1.00 | 1.01 | 1.07 | 1.00 | 1.30 | 1.05 | 1.00 | aneuploid (+C1) |
| 22 | 0.76 | 0.78 | 1.00 | 1.02 | 0.96 | 1.00 | 1.04 | 0.99 | 1.00 | aneuploid (+C2) |
| 23 | 1.31 | 1.05 | 1.00 | 0.97 | 0.92 | 1.00 | 1.07 | 1.06 | 1.00 | aneuploid (+C6) |
| 24 | 1.10 | 1.04 | 1.00 | 1.01 | 1.00 | 1.00 | 0.76 | 0.77 | 1.00 | aneuploid (+C7) |
| 25 | 1.02 | 0.97 | 1.00 | 0.76 | 0.80 | 1.00 | 1.24 | 0.99 | 1.00 | aneuploid(+C1, +C8) |
| 26 | 1.39 | 1.08 | 1.00 | 1.02 | 1.02 | 1.00 | 1.04 | 0.99 | 1.00 | aneuploid (+C6) |
| 27 | 0.98 | 0.96 | 1.00 | 1.02 | 1.06 | 1.00 | 1.31 | 1.06 | 1.00 | aneuploid (+C1) |
| 28 | 0.76 | 0.72 | 1.00 | 1.00 | 0.92 | 1.00 | 1.01 | 0.99 | 1.00 | aneuploid (+C2) |
| 29 | 0.98 | 1.01 | 1.00 | 0.78 | 0.81 | 1.00 | 1.04 | 1.07 | 1.00 | aneuploid (+C8) |
| 30 | 0.77 | 0.73 | 1.00 | 1.04 | 0.98 | 1.00 | 1.01 | 0.99 | 1.00 | aneuploid (+C2) |
| 31 | 0.95 | 0.98 | 1.00 | 1.02 | 0.95 | 1.00 | 1.38 | 1.01 | 1.00 | aneuploid (+C1) |
| 32 | 0.93 | 1.04 | 1.00 | 0.96 | 0.88 | 1.00 | 1.07 | 1.31 | 1.00 | aneuploid (+C5) |
| 33 | 0.97 | 1.03 | 1.00 | 0.75 | 0.73 | 1.00 | 1.04 | 1.30 | 1.00 | aneuploid(+C5, +C8) |
| 34 | 0.99 | 0.92 | 1.00 | 0.73 | 0.82 | 1.00 | 1.28 | 1.04 | 1.00 | aneuploid(+C1, +C8) |
| 35 | 0.93 | 0.91 | 1.00 | 1.26 | 1.08 | 1.00 | 1.04 | 0.96 | 1.00 | aneuploid (+C9) |
| 36 | 1.04 | 1.35 | 1.00 | 1.03 | 0.95 | 1.00 | 1.02 | 1.01 | 1.00 | aneuploid (+C4) |
| 37 | 1.09 | 1.37 | 1.00 | 0.95 | 0.97 | 1.00 | 0.98 | 0.95 | 1.00 | aneuploid (+C4) |

The invention claimed is:

1. A method for detecting an aneuploid of a *Brassica oleracea* plant, comprising:
providing two or more DNA primer pairs wherein each primer pair is specific to distinct chromosomes selected from 1 to 9 of the *Brassica oleracea* plant, performing real-time PCR using DNA extracted from a sample derived from the *Brassica oleracea* plant to be tested as a template and the two or more DNA primer pairs; and detecting chromosomal aneuploidy from a relative difference between the amplification values obtained by the two or more DNA primer pairs primers.

2. The method according to claim 1, further comprising determining whether the plant tested is an aneuploid for one of its chromosomes using the two or more DNA primer pairs specific to each of the chromosomes 1 to 9 of *Brassica oleracea* plant.

3. The method according to claim 1, wherein (i) each DNA primer pair is specific to one of chromosomal DNAs of the *Brassica oleracea* plant and produces an amplification product by the real-time PCR reaction when the chromosomal DNA is present; and (ii) further comprising a probe specific to the chromosomal DNA identical to any one of chromosomal DNAs described in (i) and can detect an amplification product by the real-time PCR reaction based on the primer pair described in (i).

4. The method according to claim 1, wherein the method uses an intercalator that binds to a double-stranded DNA synthesized by a PCR reaction and emits fluorescence, or uses a probe modified with a fluorescent dye so as to emit fluorescence by a PCR elongation reaction.

5. The method according to claim 1, wherein the method uses an increase in fluorescence signal obtained by real-time PCR as an index for detecting the aneuploid of chromosome.

6. The method according to claim 1, wherein the two or more DNA primer pairs comprise a nucleotide sequence selected from the group consisting of SEQ ID NOs: 1 to 18.

7. The method according to claim 1, wherein the two or more DNA primer pairs comprise a nucleotide sequence selected from the group consisting of SEQ ID NOs: 1 to 18 and one or more probes comprising a nucleotide sequence selected from the group consisting of SEQ ID NOs: 19 to 27.

8. The method according to claim 3, wherein the probe is modified with a fluorescent dye so as to emit fluorescence by a PCR elongation reaction.

9. The method according to claim 1, wherein the two or more DNA primer pairs comprises at least three DNA primer pairs which are specific to at least three distinct chromosomes of the chromosomes 1 to 9 of the *Brassica oleracea* plant.

\* \* \* \* \*

SEQUENCE LISTING

```
<160> NUMBER OF SEQ ID NOS: 27

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
ctggcaaatg taagcccttt ct                                          22

<210> SEQ ID NO 2
<211> LENGTH: 26
<212> TYPE: DNA
<213> ORGANISM: Artificial Sequence
<220> FEATURE:
<223> OTHER INFORMATION: primer

<400> SEQUENCE: 2
cttgtcttat tacagcagat gcattc                                      26

<210> SEQ ID NO 3
<211> LENGTH: 23
<212> TYPE: DNA
<213> ORGANISM: Artificial Sequence
<220> FEATURE:
<223> OTHER INFORMATION: primer

<400> SEQUENCE: 3
cgccattgct ttctctctac tct                                         23

<210> SEQ ID NO 4
```

```
<211> LENGTH: 22
<212> TYPE: DNA
<213> ORGANISM: Artificial Sequence
<220> FEATURE:
<223> OTHER INFORMATION: primer

<400> SEQUENCE: 4
gaagaggaag gactcgagga ag                                        22

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
cttaggattc gggttcgttt g                                         21

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
gccgtaagat ttcaaagaga cttc                                      24

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
cgtctcttgt ggtggttgaa g                                         21

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
tcaacttcat ctgcttggta atg                                       23

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
agcacatcat cccccatact t                                         21

<210> SEQ ID NO 10
<211> LENGTH: 23
<212> TYPE: DNA
<213> ORGANISM: Artificial Sequence
<220> FEATURE:
<223> OTHER INFORMATION: primer

<400> SEQUENCE: 10
```
cagtctctct ctccttgatg acg                                              23

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
aggaagagga aattgtcatt cg                                               22

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
gtgaccgttg cagcagataa                                                  20

<210> SEQ ID NO 13
<211> LENGTH: 26
<212> TYPE: DNA
<213> ORGANISM: Artificial Sequence
<220> FEATURE:
<223> OTHER INFORMATION: primer

<400> SEQUENCE: 13
aagaaattag ccacaagtcg taaata                                           26

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
acgtgaatga tggatatttg atctc                                            25

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
aaagctcgtg aagcaaatac tacc                                             24

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16
gaagcatacc aggagggaaa taa                                              23

<210> SEQ ID NO 17
<211> LENGTH: 20
<212> TYPE: DNA

```
<213> ORGANISM: Artificial Sequence
<220> FEATURE:
<223> OTHER INFORMATION: primer

<400> SEQUENCE: 17
gccatcgcga atcaaagata                                                    20

<210> SEQ ID NO 18
<211> LENGTH: 23
<212> TYPE: DNA
<213> ORGANISM: Artificial Sequence
<220> FEATURE:
<223> OTHER INFORMATION: primer

<400> SEQUENCE: 18
atttggtatt ttgcaggcta cag                                                23

<210> SEQ ID NO 19
<211> LENGTH: 30
<212> TYPE: DNA
<213> ORGANISM: Artificial Sequence
<220> FEATURE:
<223> OTHER INFORMATION: probe

<400> SEQUENCE: 19
cacttgtaaa acatgggttt gatcaaaaga                                         30

<210> SEQ ID NO 20
<211> LENGTH: 24
<212> TYPE: DNA
<213> ORGANISM: Artificial Sequence
<220> FEATURE:
<223> OTHER INFORMATION: probe

<400> SEQUENCE: 20
tcctctactt ccaccccatc tgcc                                               24

<210> SEQ ID NO 21
<211> LENGTH: 25
<212> TYPE: DNA
<213> ORGANISM: Artificial Sequence
<220> FEATURE:
<223> OTHER INFORMATION: probe

<400> SEQUENCE: 21
ccgatctgaa aagggagcta acgac                                              25

<210> SEQ ID NO 22
<211> LENGTH: 25
<212> TYPE: DNA
<213> ORGANISM: Artificial Sequence
<220> FEATURE:
<223> OTHER INFORMATION: probe

<400> SEQUENCE: 22
ttgcagcaag gagcttagac cacag                                              25

<210> SEQ ID NO 23
<211> LENGTH: 25
<212> TYPE: DNA
<213> ORGANISM: Artificial Sequence
<220> FEATURE:
<223> OTHER INFORMATION: probe

<400> SEQUENCE: 23
tctcgagaaa tctcatcgct gcttg                                              25
```

```
<210> SEQ ID NO 24
<211> LENGTH: 25
<212> TYPE: DNA
<213> ORGANISM: Artificial Sequence
<220> FEATURE:
<223> OTHER INFORMATION: probe

<400> SEQUENCE: 24
ttctcagagc tgttccctcc tccac                                          25

<210> SEQ ID NO 25
<211> LENGTH: 27
<212> TYPE: DNA
<213> ORGANISM: Artificial Sequence
<220> FEATURE:
<223> OTHER INFORMATION: probe

<400> SEQUENCE: 25
ttgcaccacc gttacctttt aacacaa                                        27

<210> SEQ ID NO 26
<211> LENGTH: 26
<212> TYPE: DNA
<213> ORGANISM: Artificial Sequence
<220> FEATURE:
<223> OTHER INFORMATION: probe

<400> SEQUENCE: 26
tgttttgttt ggtgggcaaa tctctt                                         26

<210> SEQ ID NO 27
<211> LENGTH: 25
<212> TYPE: DNA
<213> ORGANISM: Artificial Sequence
<220> FEATURE:
<223> OTHER INFORMATION: probe

<400> SEQUENCE: 27
tggagatctt ccacctcatc ttgga                                          25
```